(12) United States Patent
Schäfer et al.

(10) Patent No.: US 7,968,872 B2
(45) Date of Patent: Jun. 28, 2011

(54) POLYMERS

(75) Inventors: Thomas Schäfer, Liestal (CH); Klaus Müllen, Köln (DE); Mathieu G. R. Turbiez, Rixheim (FR); Martin Baumgarten, Mainz (DE)

(73) Assignee: BASF SE, Ludwigshafen (DE)

( * ) Notice: Subject to any disclaimer, the term of this patent is extended or adjusted under 35 U.S.C. 154(b) by 206 days.

(21) Appl. No.: 12/309,379

(22) PCT Filed: Jul. 18, 2007

(86) PCT No.: PCT/EP2007/057408
§ 371 (c)(1),
(2), (4) Date: Jan. 15, 2009

(87) PCT Pub. No.: WO2008/012250
PCT Pub. Date: Jan. 31, 2008

(65) Prior Publication Data
US 2009/0203866 A1  Aug. 13, 2009

(30) Foreign Application Priority Data
Jul. 28, 2006  (EP) .................... 06118100

(51) Int. Cl.
*H01L 51/00* (2006.01)
(52) U.S. Cl. ........... 257/40; 257/E51.027; 257/E51.028; 428/917; 313/504; 585/19; 585/26
(58) Field of Classification Search .......... 257/40, 257/E51.027, E51.028; 428/917; 313/504
See application file for complete search history.

(56) References Cited

U.S. PATENT DOCUMENTS

| | | | |
|---|---|---|---|
| 3,711,567 A | 1/1973 | Innes | 260/668 |
| 2002/0040805 A1 | 4/2002 | Swager | 174/110 |
| 2004/0076852 A1 | 4/2004 | Cheng et al. | 428/690 |
| 2006/0120917 A1 | 6/2006 | Swager | 422/56 |
| 2006/0280965 A1* | 12/2006 | Kwong et al. | 428/690 |
| 2008/0265750 A1 | 10/2008 | Matsumoto et al. | 313/504 |
| 2009/0134780 A1* | 5/2009 | Ono et al. | 313/504 |

FOREIGN PATENT DOCUMENTS

| | | |
|---|---|---|
| JP | 1-192420 | 8/1989 |
| JP | 2006-143845 | 6/2006 |
| WO | 2006/038709 | 4/2006 |
| WO | 2006/130598 | 12/2006 |
| WO | 2007/017066 | 2/2007 |

OTHER PUBLICATIONS

Cammidge et al., J. Mater. Chem., 2001, 11, 2773-2783.*
Bacher A et al: "Photo-Cross-Linked Triphenylenes As Novel Insoluble Hole Transport Materials in Organic LEDS" Macromolecules, ACS, Washington, DC, US, vol. 32, No. 14, Jul. 13, 1999, pp. 4551-4557, XP000833930 ISSN: 0024-9297.
Yatabe T et al: "Extended Triphenylenes: Synthesis, Mesomorphic Properties and Molecularly Resolved Scanning Tunneling Microscopy Images of Hexakis(Dialkoxyphenyl)Triphenylenes and Dodeca(Alkoxy)Tris(Triphenyl Enylene)S" Journal of Materials Chemistry, The Royal Society of Chemistry, Cambridge, GB, vol. 10, No. 7, 2000, pp. 1519-1525, XP001001117 ISSN: 0959-9428.
K. Rosmarion et al., Appl. Spectr. 59 (2005) 376.
R. Tokhunts et al., Spectr. Lett. 37 (2004) 533.
English Language abstract of JP 2006-143845 from the esp@cenet web site printed on Mar. 6, 2009.
English Language abstract of JP 1-192420 from the esp@cenet web site printed on Mar. 6, 2009.
English Language abstract of JP 1-192420from the esp@cenet web site printed on Mar. 6, 2009.
English Language abstract of WO 2207/017066 from the esp@cenet web site printed on Mar. 6, 2009.

* cited by examiner

*Primary Examiner* — David Wu
*Assistant Examiner* — Vu A Nguyen
(74) *Attorney, Agent, or Firm* — Shiela A. Loggins; Qi Zhuo

(57) ABSTRACT

The present invention relates to polymers comprising repeating unit(s) of the formula (I), and their use in electronic devices. The polymers according to the invention have excellent solubility in organic solvents and excellent film-forming properties. In addition, high charge carrier mobilities and high temperature stability of the emission color are observed, if the polymers according to the invention are used in polymer light emitting diodes (PLEDs).

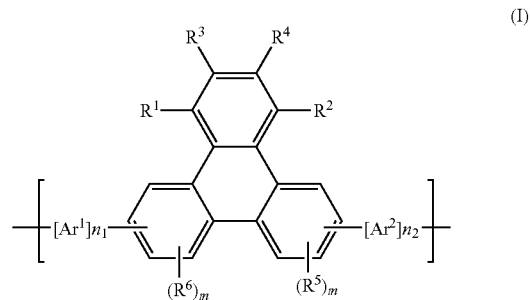

18 Claims, No Drawings

POLYMERS

The present invention relates to novel polymers comprising repeating unit(s) of the formula I and their use in electronic devices. The polymers according to the invention have excellent solubility in organic solvents and excellent film-forming properties. In addition, high charge carrier mobilities and high temperature stability of the emission color can be observed, if the polymers according to the invention are used in polymer light emitting diodes (PLEDs).

JP11092420 relates to triphenylene derivatives of the formula

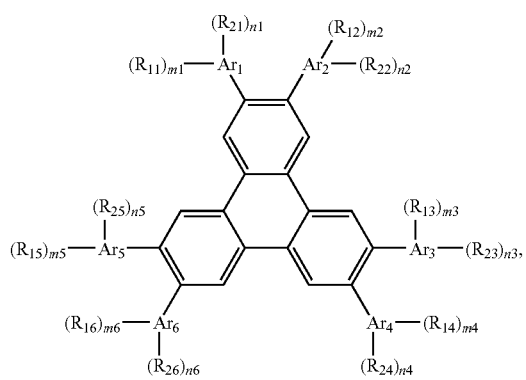

wherein $Ar_1$ to $Ar_6$ are each an aryl or the like; $R_{11}$ to $R_{16}$ are each formula

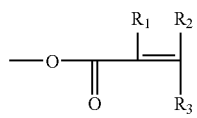

($R_1$ to $R_3$ are each, for example, H); $R_{21}$ to $R_{26}$ are each, for example, an alkyl; m1-m6 are each 0 or 1; n1-n6 are each 0, 1, or 2, which are useful as a liquid crystalline material. The following compounds are explicitly disclosed:

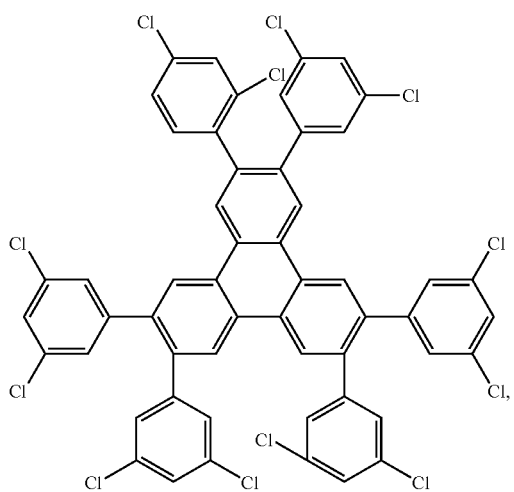

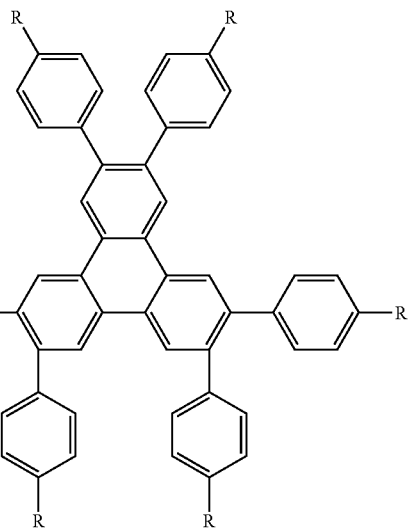

R=Cl, Br, or F.

JP2006143845 relates to compounds of formula

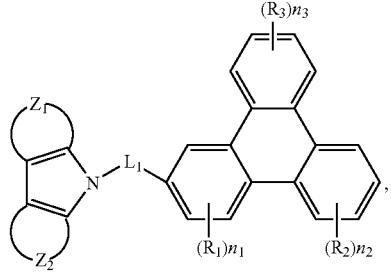

wherein $Z_1$, $Z_2$ are an aromatic hydrocarbon ring, aromatic heterocyclic ring; $R_1$ to $R_3$ are H, substituent; n1=0 to 3; n2, n3=0 to 4; L1=linkage group, single bond). The compounds show high luminescence efficiency and long service life. The following compound

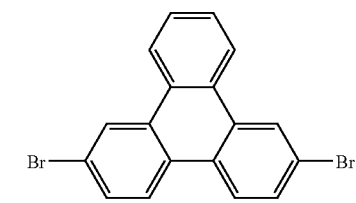

is used as starting material for the preparation of the above compounds.

WO2006038709 compounds represented by the general formula

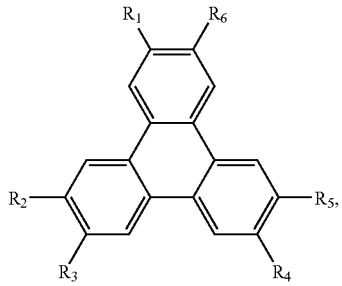

wherein $R_1$ to $R_6$ are each independently hydrogen or substituent represented by the general formula —C≡CSiRaRbRc, with the proviso that at least one of $R_1$ to $R_6$ is a substituent represented by the general formula —C≡CSiRaRbRc, wherein Ra, Rb, Rc are each independently an $C_1$-$C_{10}$ aliphatic hydrocarbon group or aromatic hydrocarbon group. The compounds are prepared by coupling of halogenated triphenylene compounds.

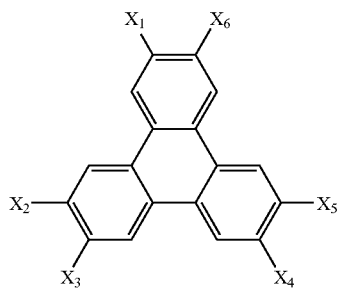

($X_1$ to $X_6$ are each independently H, Br, or iodo, with the proviso that at least one of X1-X6 is Br or iodo) with a silylacetylene of general formula HC≡C SiRaRbRc (Ra, Rb, Rc=same as above). An organic electroluminescent device comprising a luminescent layer containing at least one of compounds of formula

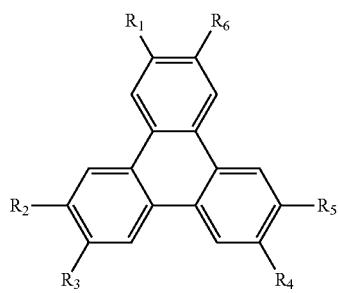

and a phosphorescent dopant is also disclosed. A compound of formula

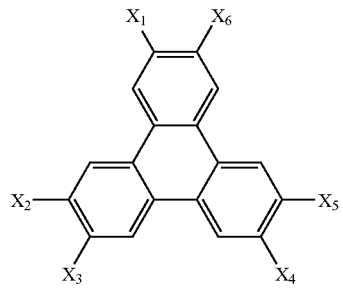

is explicitly disclosed, wherein $X_1$ to $X_6$ are each Br.

US2005025993 relates to ectroluminescent devices which comprise an anode; a cathode; a first organic layer disposed between the anode and the cathode, where the first organic layer comprises a material that produces phosphorescent emission when a voltage is applied between the anode and the cathode; and a second organic layer disposed between the first organic layer and the cathode, where the second organic layer is in direct contact with the first organic layer, and where the second organic layer comprises a nonheterocyclic aromatic hydrocarbon material, such as, for example,

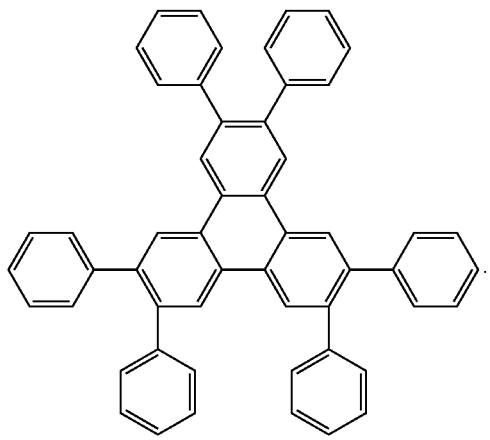

US2004209117 relates to an EL device, comprising an azole compound of the formula

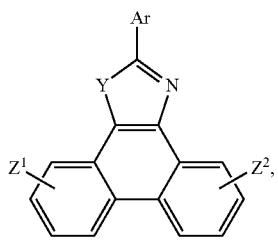

wherein Y is an atom or a group selected from the group consisting of O, S, and —N(R)—, wherein R is a hydrocarbyl group of from 1 to about 30 carbons; $Z^1$ and $Z^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and Ar is an aromatic component. JP2004161892, JP2002050473 and JP2001023777 disclose phenanthroimidazol compounds and their use in EL devices.

WO04/030029 relates to a photovoltaic EL cell, comprising polymers containing groups:

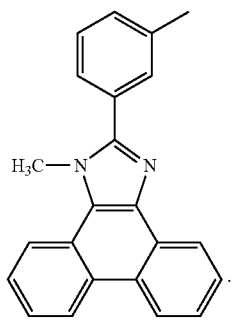

WO03/020790 relates to conjugated polymers comprising spirobifluorene units. The polymers can comprise repeating units derived from the following compound

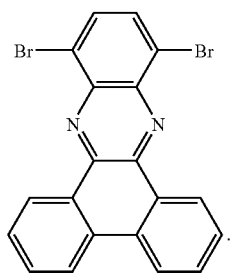

EP0757035A1 relates to phenanthrylenediamine derivatives represented by the general formula

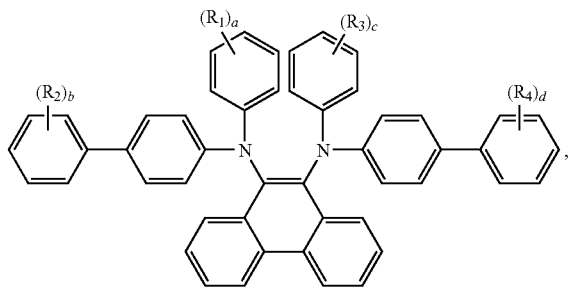

which are excellent in the electric charge transferring capability, the compatibility with a binding resin and the stability, thereby providing a photosensitive material which is highly sensitive and excellent in the durability.

US2001008711 relates to an organic light-emitting device comprising a light-emitting layer or a plurality of organic compound thin layers including a light-emitting layer formed between a pair of electrodes, wherein at least one layer comprises at least one kind of compound represented by the following formula $NR_{11}R_{12}R_{13}$: wherein $R_{11}$, $R_{12}$ and $R_{13}$ each represents a group having a cyclocondensed polycyclic hydrocarbon structure in which three or more rings are cyclocondensed; and a novel cyclocondensed polycyclic hydrocarbon compound.

US2004/0028944 relates to organic electroluminescent devices comprising a triarylamine derivative represented by the general formula $N(Ar_1)(Ar_2)(Ar_3)$, wherein $Ar_1$ to $Ar_3$ are substituted or unsubstituted aryl groups and at least one of $Ar_1$ to $Ar_3$ is a 9-phenanthryl group.

EP1440959A1 relates to a novel soluble compound of formula

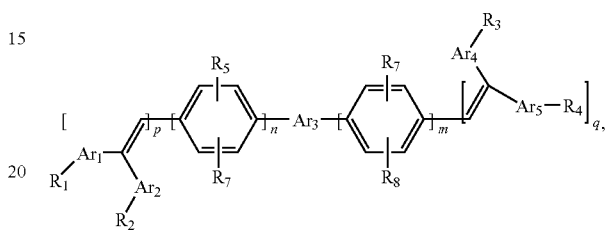

wherein $Ar_3$ represents a substituted or unsubstituted anthracendiyl group, or a substituted or unsubstituted fluorendiyl group and to its use in an electroluminescent device.

WO03/064373 relates to triarylamine derivatives and the use thereof as hole transport material in organic electroluminescent and electrophotographic devices.

WO04/005288 relates to charge transport compositions comprising a phenanthroline derivative having formula

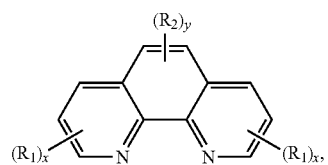

wherein: $R_1$ and $R_2$ are the same or different at each occurrence and are selected from H, F, Cl, Br, alkyl, heteroalkyl, alkenyl, alkynyl, aryl, heteroaryl, $C_nH_aF_b$, $OC_nH_aF_b$, $C_6H_cF_d$, and $OC_6H_cF_d$; a, b, c, and d are 0 or an integer such that $a+b=2n+1$, and $c+d=5$, n is an integer; x is 0 or an integer from 1 through 3; y is 0, 1 or 2; with the proviso that there is at least one substituent on an aromatic group selected from F, $C_nH_aF_b$, $OC_nH_aF_b$, $C_gH_cF_d$, and $OC_6H_cF_d$.

WO05/014689 relates to conjugated polymers containing dihydrophenanthrene units of formula

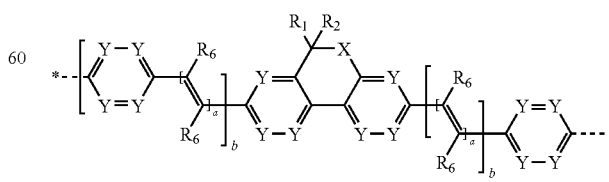

and their use in polymer organic light emitting diodes.

WO05/104264 relates to polymers comprising structural units of formula

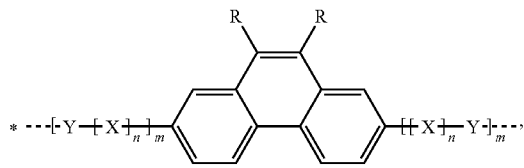

wherein both groups R among others can form together a mono- or polycyclic, aliphatic ring system.

WO07/017,066, which enjoys an earlier priority date than the present, but has been published after the priority date of the present invention relates to polymers comprising structural units of formula

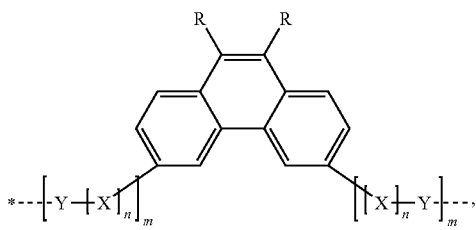

wherein both groups R among others can form together a mono- or polycyclic, aromatic aliphatic ring system.

WO2005030828 relates to polymers comprising repeating units of formula

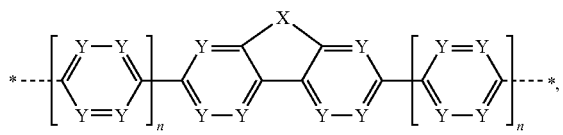

wherein X is $CR_2$, $N(R^1)$, $-CR_2-CR_2-$, or $-N(R^1)-CR_2-$ and Z is CR, or N. The polymers have high solubility, exhibit an excellent air-stability and a low voltage rise during longer operation when used in a polymer organic light-emitting diode (PLED).

There are a number of challenges faced with the introduction of organic EL displays when their performance is compared with existing technologies. Obtaining the exact color coordinates required by specific guidelines (i.e. NTSC) has been problematic. The operational lifetime of the EL device is still lower when contrasted to the existing inorganic technology for cathode ray tubes (CRTs) and liquid crystal displays (LCDs). In addition, producing a material with a pure blue color and a long lifetime is one of the greatest problems for this industry.

Accordingly, it is the object of the present invention to provide novel materials, which show significant advantages in color purity, device efficiency and/or operational lifetime, when incorporated in electro-optical devices.

Said object is solved by the polymers of the present invention comprising repeating units of formula I. Organic light emitting devices (OLEDs), comprising the polymers of the present invention, can show significant advantages in color purity, device efficiency and/or operational lifetime. In addition, the polymers can have good solubility characteristics and relatively high glass transition temperatures, which facilitates their fabrication into coatings and thin films, that are thermally and mechanically stable and relatively free of defects. If the polymers contain end groups which are capable of being crosslinked, the crosslinking of such groups after the films or coating is formed increases the solvent resistance thereof, which is beneficial in applications wherein one or more solvent-based layers of material are deposited thereon.

Hence, the present invention relates to polymers comprising repeating unit(s) of the formula

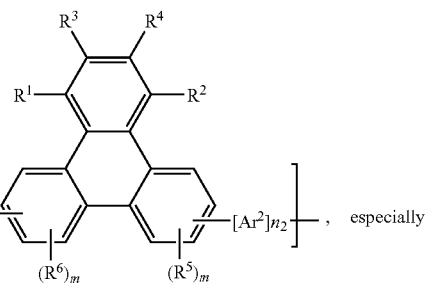

(I)

especially

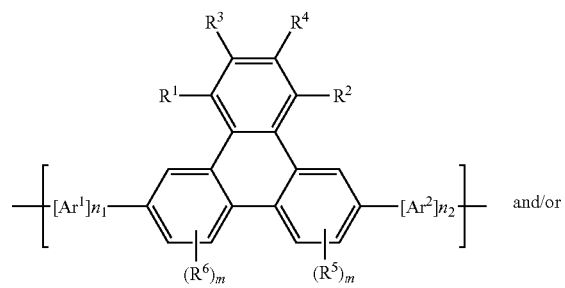

(II)

and/or

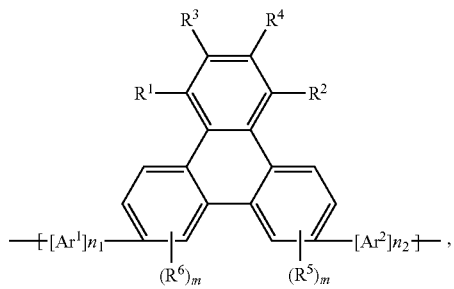

(III)

wherein
$R^1$, $R^2$, $R^3$, $R^4$, $R^5$, $R^6$ and are independently of each other hydrogen, F, $SiR^{100}R^{101}R^{102}$, or an organic substituent, or $R^1$ and $R^3$, $R^4$ and $R^2$, $R^3$ and $R^4$, and/or any of the substituents $R^5$ and/or $R^6$, which are adjacent to each other, together form an aromatic, or heteroaromatic ring, or ring system, which can optionally be substituted, m is 0, or an integer of 1 to 3,
n1 and n2 are 0, or an integer 1, or 2,
$R^{100}$, $R^{101}$ and $R^{102}$ are independently of each other $C_1$-$C_{18}$alkyl, substituted or unsubstituted $C_6$-$C_{18}$aryl, and $Ar^1$ and $Ar^2$ are each independently of each other a substituted or unsubstituted arylen, or heteroarylen group, such as a substituted or unsubstituted phenylene group, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group.

The polymers of the present invention should have a glass transition temperature above 100° C., especially a glass transition temperature above 150° C.

$R^1$ and $R^2$ as well as $R^3$ and $R^4$ can be different from each other, but are preferably the same. $R^1$, $R^2$, $R^3$ and $R^4$ are preferably selected from $C_1$-$C_{18}$alkyl, $C_1$-$C_{18}$alkyl which is substituted by E and/or interrupted by D, $C_1$-$C_{18}$perfluoroalkyl and are most preferred an optionally substituted $C_6$-$C_{24}$aryl, or $C_2$-$C_{20}$heteroaryl group.

In a preferred embodiment of the present invention at least one, very especially at least two of $R^1$, $R^2$, $R^3$ and $R^4$ are different from H. Most preferred all of the substituents $R^1$, $R^2$, $R^3$ and $R^4$ are different from H. In another preferred embodiment of the present invention at least one, preferably two of the substituents $R^1$, $R^2$, $R^3$ and $R^4$ are an optionally substituted $C_6$-$C_{24}$aryl, or $C_2$-$C_{20}$heteroaryl group. Most preferred all of the substituents $R^1$, $R^2$, $R^3$ and $R^4$ are an optionally substituted $C_6$-$C_{24}$aryl, or $C_2$-$C_{20}$heteroaryl group.

Preferably, the polymer of the present invention comprises repeating unit(s) of formula I, wherein $R^1$ and $R^2$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G;

$R^3$ and $R^4$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G; wherein especially at least one, very especially at least two of $R^1$, $R^2$, $R^3$ and $R^4$ are different from H; wherein especially at least one, very especially at least two of $R^1$, $R^2$, $R^3$ and $R^4$ are different from H, each group $R^5$ and $R^6$ is independently of each other in each occurrence H, halogen, especially F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, m is 0, or an integer 1 to 3, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen, especially F;

G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{27}$ is H; $C_6$-$C_{18}$aryl; $C_6$-$C_{18}$aryl which is substituted by $C_1$-$C_{18}$alkyl, or $C_1$-$C_{18}$alkoxy; especially $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl.

In an especially preferred embodiment the polymers contain repeating units of formula

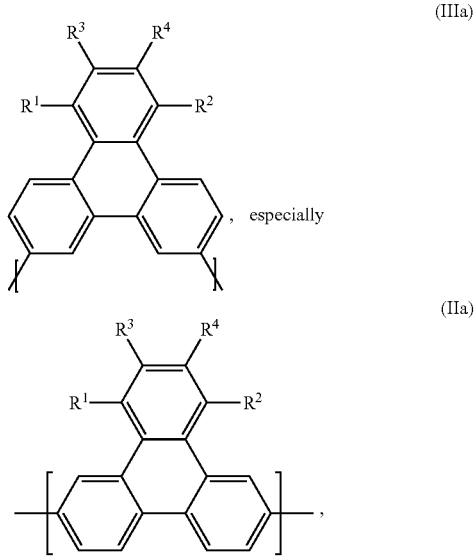

, especially wherein $R^1$, $R^2$ and $R^3$ are independently of each other $C_6$-$C_{12}$aryl, or $C_2$-$C_{11}$heteroaryl, which may optionally be substituted by one or more groups G, wherein G is as defined above, and $R^4$ has the meaning of $R^3$, or is $C_1$-$C_{18}$alkyl, especially $C_4$-$C_{18}$alkyl. Polymers are even more preferred, which contain repeating units of formula (IIa), wherein $R^1$, $R^2$ and $R^3$ are independently of each other

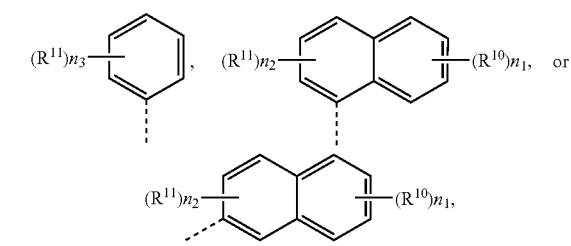

wherein $n_1$ is 0, or an integer 1, 2, 3, or 4, especially 0, 1, or 2; $n_2$ is 0, or an integer 1, 2, or 3, especially 0, 1, or 2; $n_3$ is 0, or an integer 1, 2, 3, 4, or 5, especially 0, 1, 2, or 3; and $R^{10}$ and $R^{11}$ are independently of each other $C_1$-$C_{25}$alkyl, or $C_1$-$C_{25}$alkoxy, and $R^4$ has the meaning of $R^3$, or is $C_1$-$C_{18}$alkyl, especially $C_4$-$C_{18}$alkyl.

Preferably, $R^5$ and $R^6$ are independently of each other H, $C_1$-$C_{18}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl; $C_1$-$C_{18}$alkyl which is substituted by E and/or interrupted by D, such as —CH$_2$OCH$_3$, —CH$_2$OCH$_2$CH$_3$, —CH$_2$OCH$_2$CH$_2$OCH$_3$, or —CH$_2$OCH$_2$CH$_2$OCH$_2$CH$_3$; $C_1$-$C_{18}$alkoxy, such as methoxy, ethoxy, n-propoxy, iso-propoxy, n-butoxy, isobutoxy, sec-butoxy, t-butoxy, 2-methylbutoxy, n-pentyloxy, isopentyloxy, n-hexyloxy, 2-ethylhexyloxy, or n-heptyloxy;

$C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as —$C_6H_4OCH_3$, —$C_6H_4OCH_2CH_3$, —$C_6H_3(OCH_3)_2$, or —$C_6H_3(OCH_2CH_3)_2$, —$C_6H_4CH_3$, —$C_6H_3(CH_3)_2$, —$C_6H_2(CH_3)_3$, —$C_6H_4OtBu$, or —$C_6H_4tBu$. Most preferred $R^5$ and $R^6$ are H.

m is preferably 0, 1 or 2. If more than one group $R^5$, or $R^6$ is present within one molecule, they can have different meanings.

D is preferably —CO—, —COO—, —S—, —SO—, —$SO_2$—, —O—, —$NR^{25}$—, wherein $R^{25}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, naphthyl, or biphenylyl.

E is preferably —$OR^{29}$; —$SR^{29}$; —$NR^{25}R^{25}$; —$COR^{28}$; —$COOR^{27}$; —$CONR^{25}R^{25}$; or —CN; wherein $R^{25}$, $R^{27}$, $R^23$ and $R2^{69}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, naphthyl, or biphenylyl.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, 1-(2-hexyl)-decane, or 2-ethyl-hexyl.

Examples of especially preferred polymers, comprising repeating unit(s) of formula (IIa) are shown below:

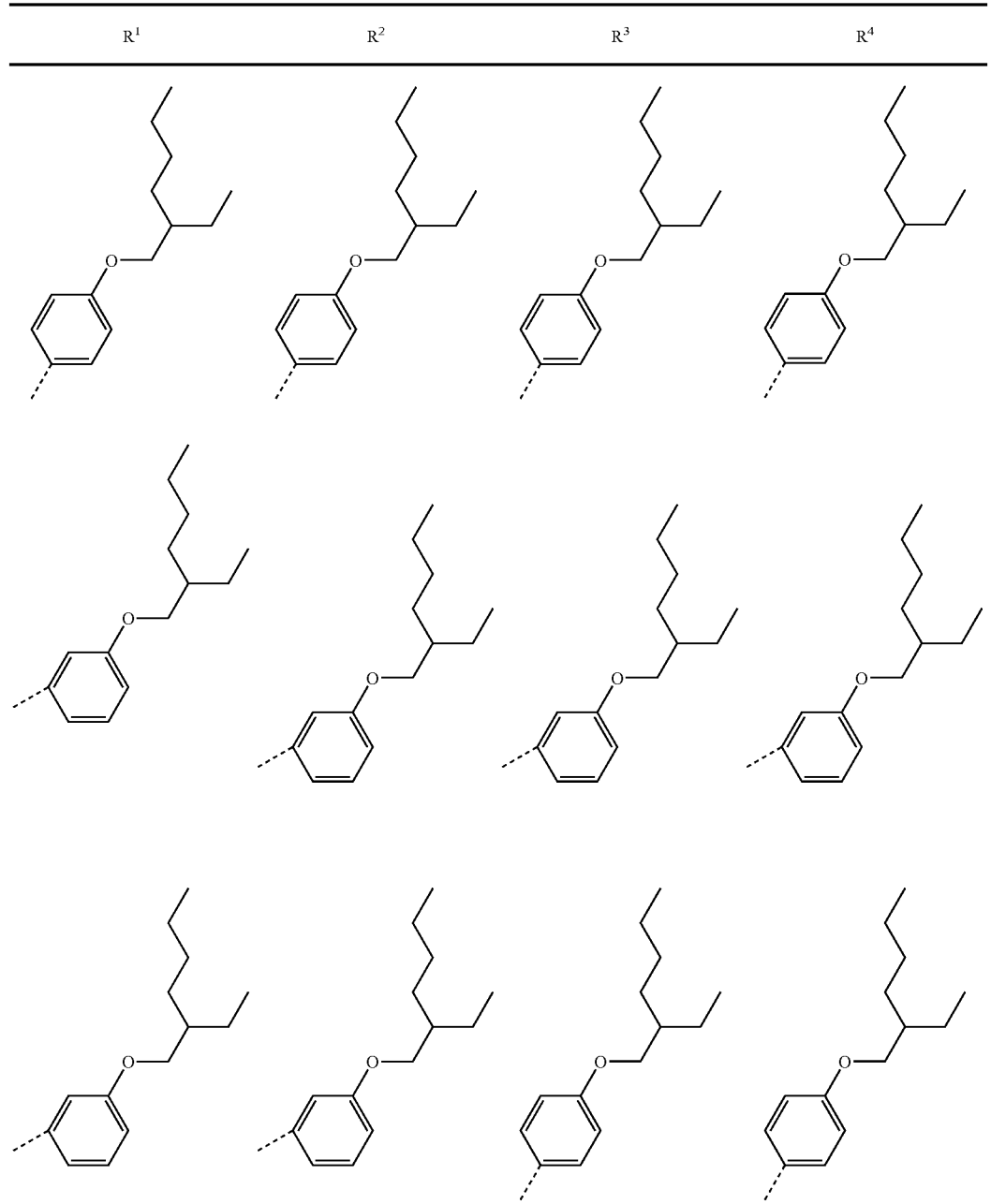

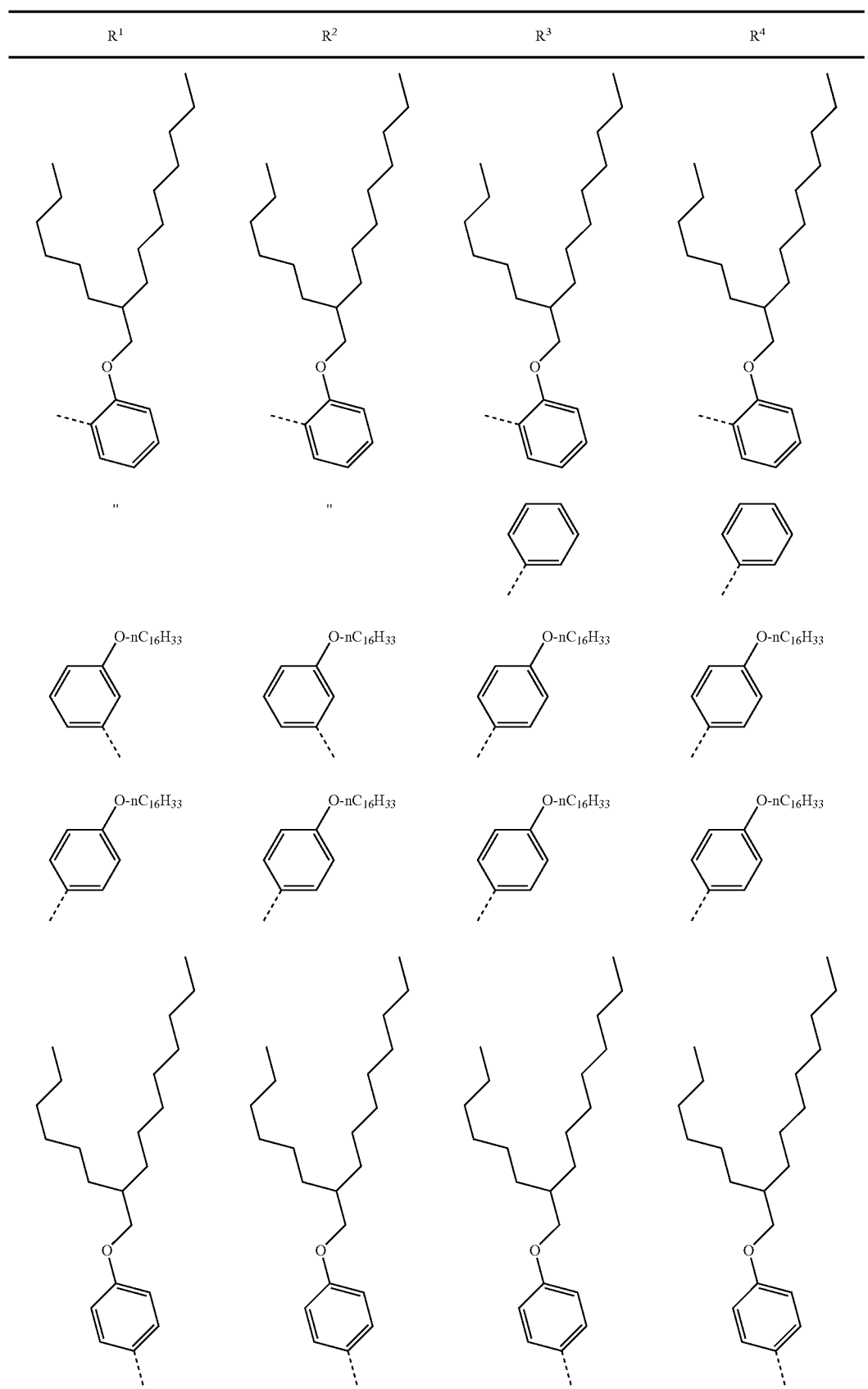

-continued
| R¹ | R² | R³ | R⁴ |
|---|---|---|---|
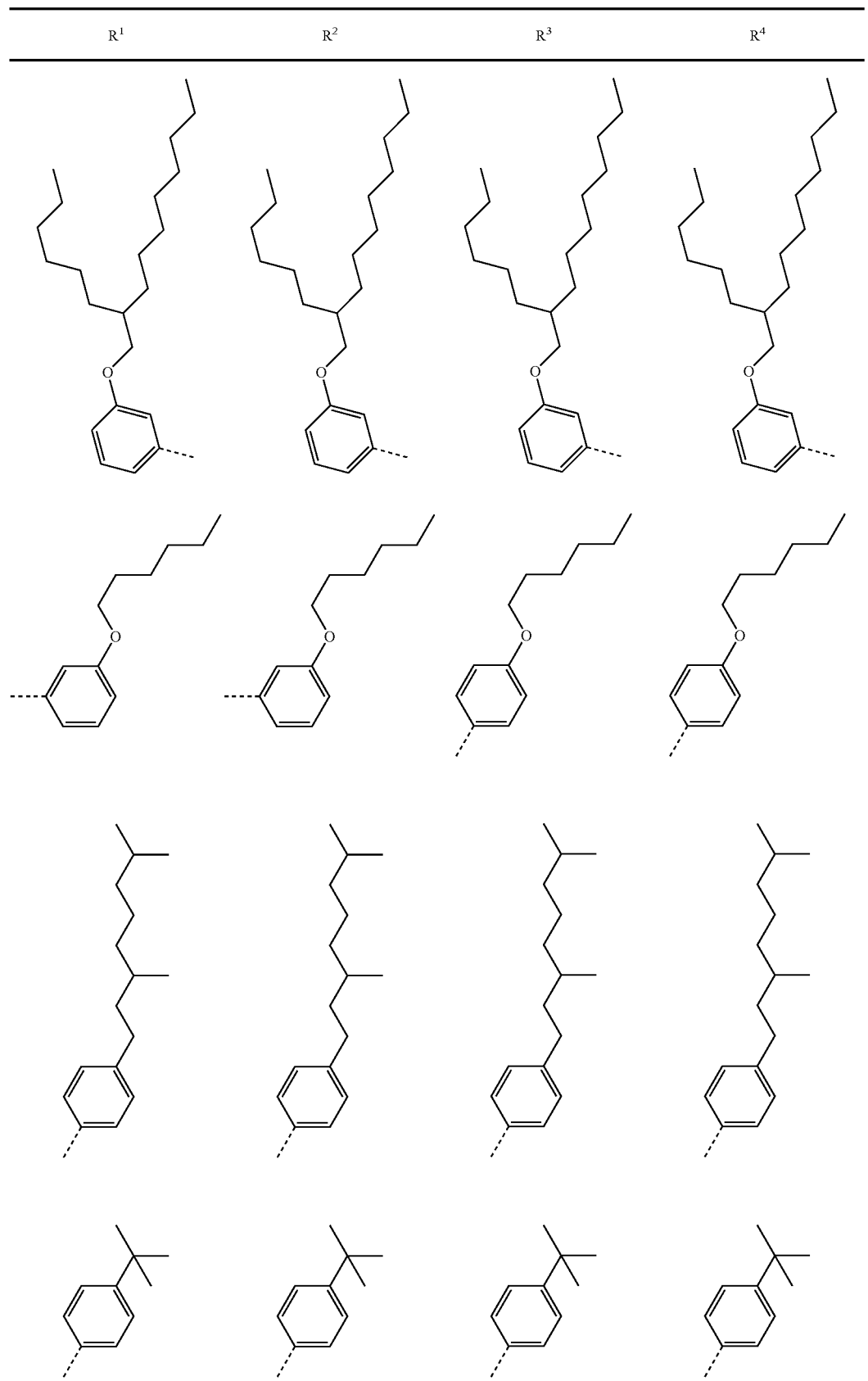

-continued
| R¹ | R² | R³ | R⁴ |
|---|---|---|---|
| 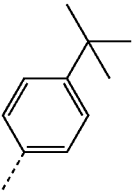 | 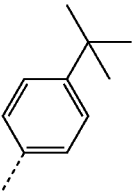 | 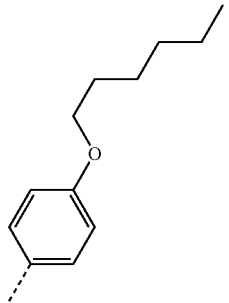 | 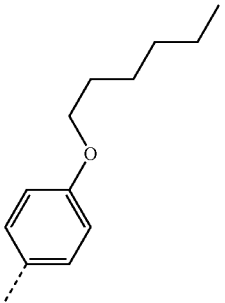 |
| 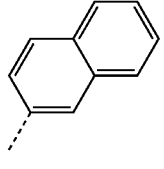 | 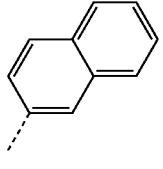 | 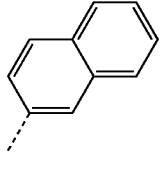 | 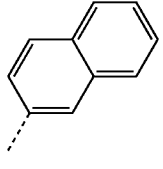 |
| 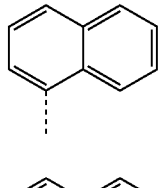 | 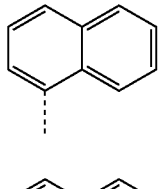 | 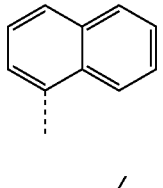 | 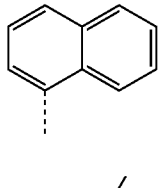 |
| 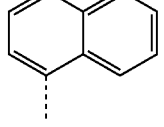 | 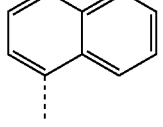 | 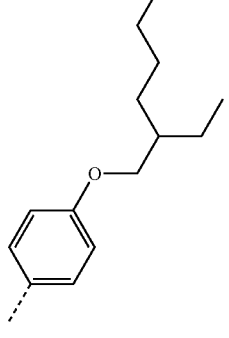 | 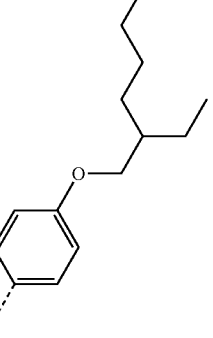 |
| 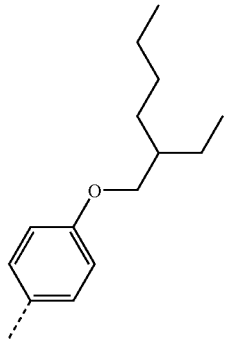 | 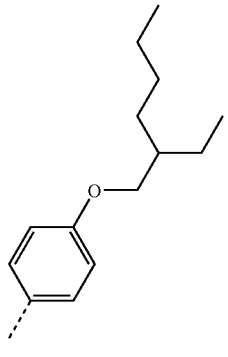 | 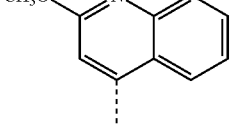 | 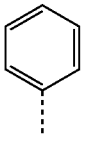 |
| " | " | tBu | 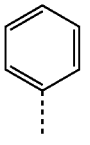 |

-continued

| R¹ | R² | R³ | R⁴ |
|---|---|---|---|
| " | " | phenyl | 3-(trifluoromethyl)phenyl |
| " | " | pyridin-3-yl | tBu |
| 4-(2-ethylhexyloxy)phenyl | 4-(2-ethylhexyloxy)phenyl | pyridin-2-yl | pyridin-2-yl |
| 4-(2-ethylhexyloxy)phenyl | 4-(2-ethylhexyloxy)phenyl | pyridin-4-yl | pyridin-4-yl |
| 4-(2-ethylhexyloxy)phenyl | 4-(2-ethylhexyloxy)phenyl | thiophen-2-yl | thiophen-2-yl |
| 4-(2-ethylhexyloxy)phenyl | 4-(2-ethylhexyloxy)phenyl | furan-2-yl | furan-2-yl |

-continued
| R¹ | R² | R³ | R⁴ |
|---|---|---|---|
|  |  |  |  |
| 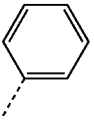 | 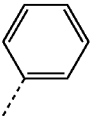 | 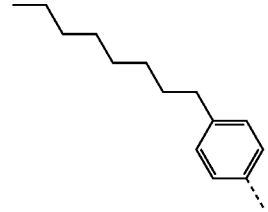 |  |
| 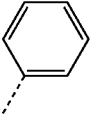 | 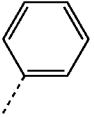 | 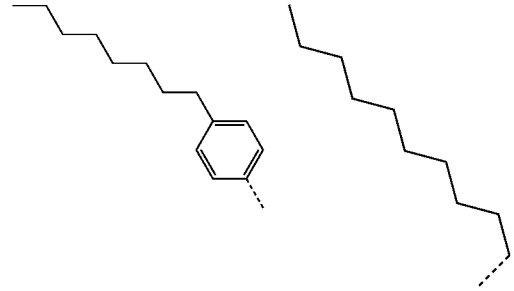 | 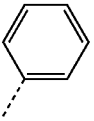 |
| 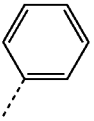 | 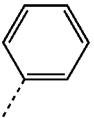 | 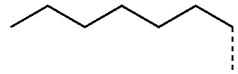 | 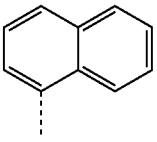 |
| 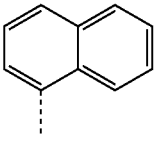 | 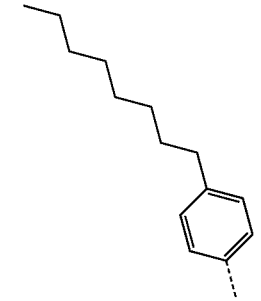 |  | 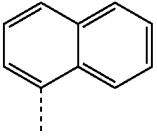 |
| 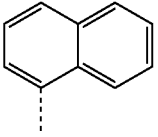 | 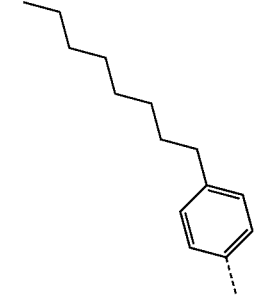 |  | |

The monomers for the preparation of the polymers of the present invention are new and form a further embodiment of the present invention. Accordingly, the present invention is also directed to monomers of the formula

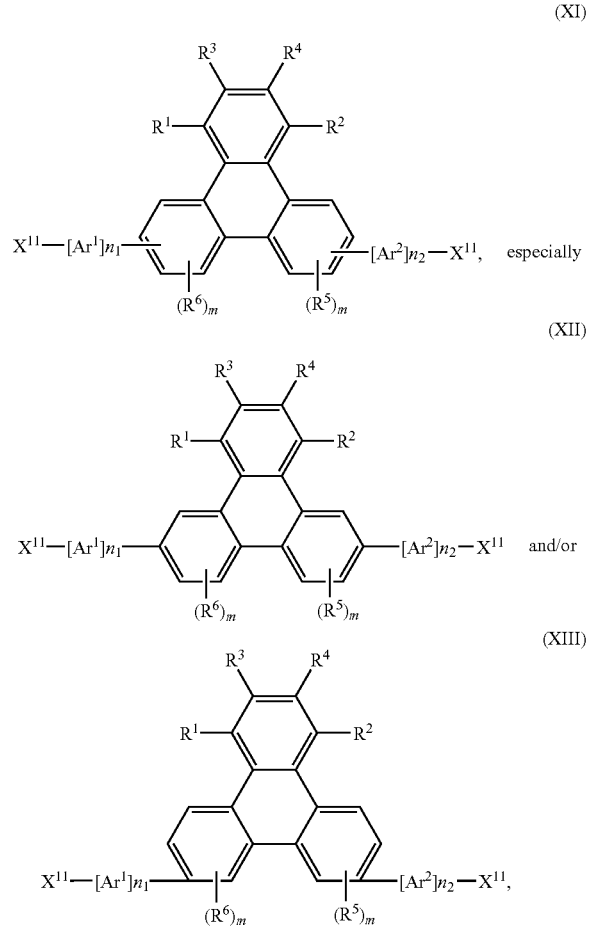

wherein $Ar^1$, $Ar^2$, $n_1$, $n_2$, $R^1$, $R^2$, $R^3$, $R^4$, $R^5$, $R^6$ and m are as defined above. $X^{11}$ is independently in each occurrence a halogen atom, especially I, Cl, or Br; —$ZnX^{12}$, —$SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, very especially I, or Br; or —$OS(O)_2CF_3$, —$OS(O)_2$-aryl, especially

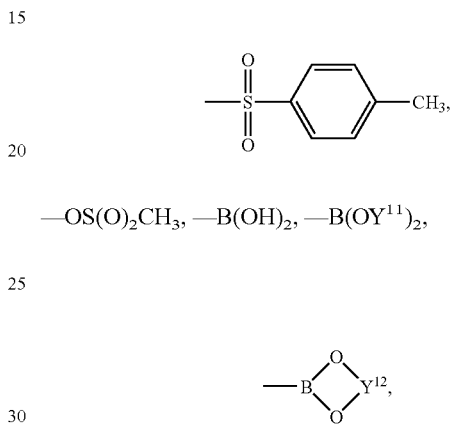

—$OS(O)_2CH_3$, —$B(OH)_2$, —$B(OY^{11})_2$,

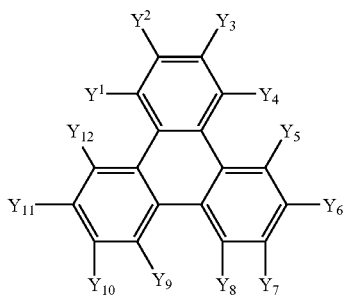

—$BF_4Na$, or —$BF_4K$, wherein $Y^{11}$ is independently in each occurrence a $C_1$-$C_{10}$alkyl group and $Y^{12}$ is independently in each occurrence a $C_2$-$C_{10}$alkylene group, such as —$CY^{13}Y^{14}$—$CY^{15}Y^{16}$—, or —$CY^{17}Y^{18}$—$CY^{19}Y^{20}$—$CY^{21}Y^{22}$—, wherein $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ are independently of each other hydrogen, or a $C_1$-$C_{10}$alkyl group, especially —$C(CH_3)_2C(CH_3)_2$—, or —$C(CH_3)_2CH_2C(CH_3)_2$—, with the proviso that the following compounds are excluded:

| $Y^2$ | $Y^3$ | $Y^5$ | $Y^6$ | $Y^7$ | $Y^8$ | $Y^9$ | $Y^{10}$ | $Y^{11}$ | $Y^{12}$ |
|---|---|---|---|---|---|---|---|---|---|
| $(CH_2)_5Me$ | $(CH_2)_5Me$ | H | H | Br | H | H | Br | H | H |
| OMe | OMe | OAc | H | Cl | OAc | OAc | Cl | H | OAc |
| 1) | 1) | H | 1) | Br | H | H | Br | 1) | H |
| 1) | 1) | H | Br | 1) | H | H | 1) | Br | H |
| 1) | 1) | H | H | Cl | H | H | Cl | H | H |
| H | H | H | H | Cl | H | H | Cl | H | H |
| 1) | 1) | H | H | Br | H | H | Br | H | H |
| H | H | H | Br | H | H | H | H | Br | H |

-continued
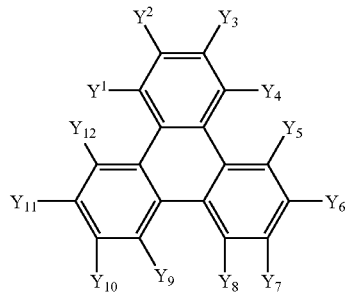
| $Y^2$ | $Y^3$ | $Y^5$ | $Y^6$ | $Y^7$ | $Y^8$ | $Y^9$ | $Y^{10}$ | $Y^{11}$ | $Y^{12}$ |
|---|---|---|---|---|---|---|---|---|---|
| OMe | OMe | OAc | H | Cl | OAc | OAc | H | Cl | OAc |
| H | H | H | Br | H | H | H | H | Br | |
1)$O(CH_2)_5Me$,
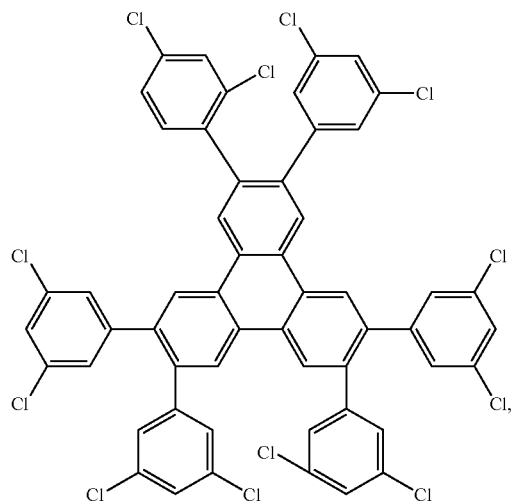
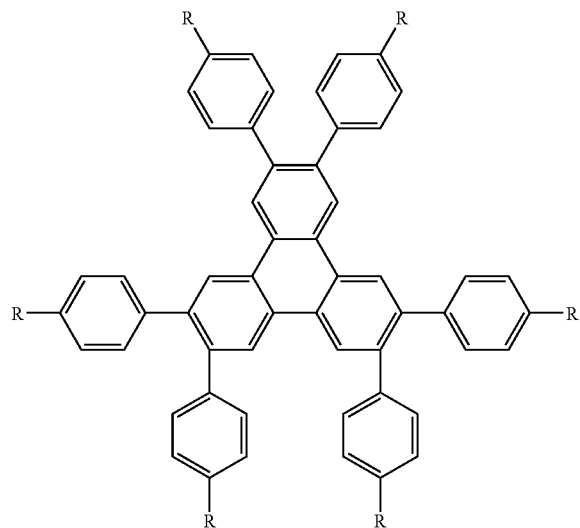
R = Cl, Br, or F.

The compounds of the formula XI are obtained by reacting a compound of the formula XIV with an alkine of formula $R^3 \equiv\!\!\!= R^4$:

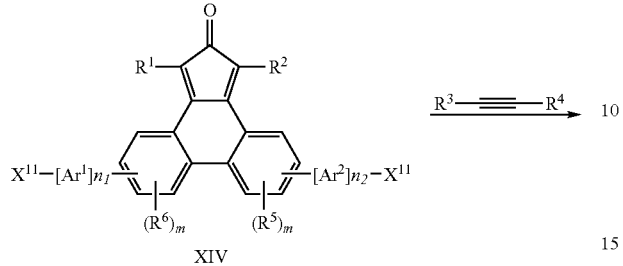

XIV

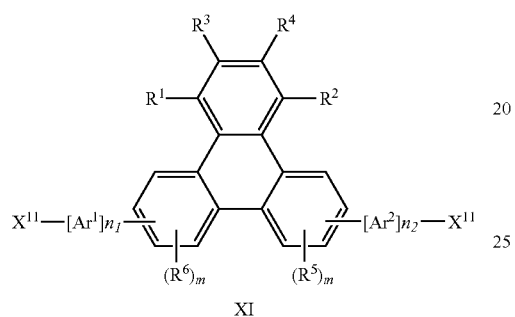

XI

The Diels-Alder reaction can be performed according to, or in analogy to methods described in Klaus Müllen et al., J. Am. Chem. Soc 2004, 126, 7794-7795 and Klaus Müllen et al., J. Am. Chem. Soc 2006, 128, 1334-1339.

The compounds of formula XIV are new and form a further embodiment of the present invention. Accordingly, the present invention is also directed compounds of the formula (XIV)

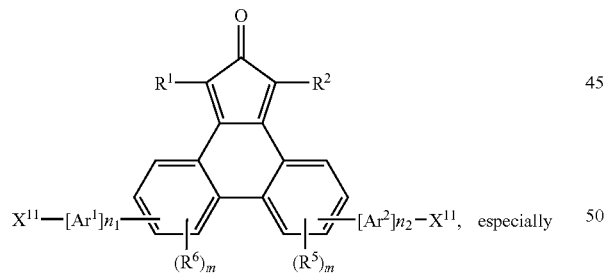

especially

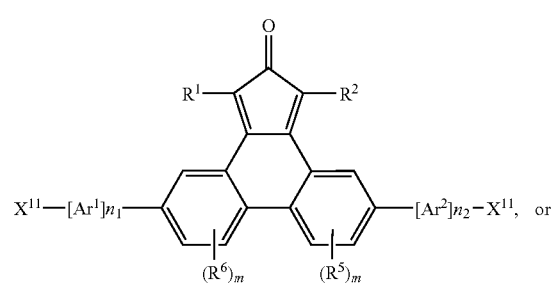

or

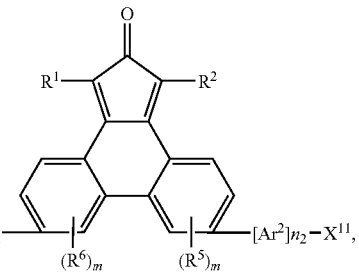

(XVI)

wherein $X^{11}$, $Ar^1$, $Ar^2$, $n_1$, $n_2$, $R^1$, $R^2$, $R^5$, $R^6$ and m are as defined above, with the proviso that the following compound is excluded:

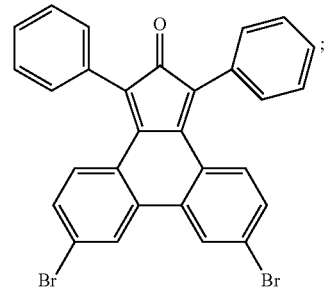

and with the further proviso that compounds of formula XIV are excluded, wherein $R^1$ and $R^2$ are a group of formula

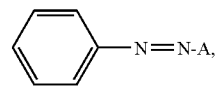

wherein A is a coupling residue having phenolic OH, $X^{11}$ is halogen, $n_1$, $n_2$ and m are 0.

The compounds of the formula XIV can be synthesized via a "Knoevennagel" condensation:

XIV (see, for example, Klaus Müllen et al., J. Am. Chem. Soc 2006, 128, 1334-1339 and literature cited therein).

The alkines can be prepared via Sonogashira coupling (see, for example, Jason M. Nolan and Daniel L. Comins, J. Org. Chem. 2003, 68, 3736-3738; Zhaoguo Zhang et al., J. Org. Chem. 2004, 69, 5428-5432; Dmitri Gelman, Stephen L. Buchwald, Angew. Chem. Int. Ed. 2003, 42, 5993-5996; Rik R. Tykwinski, Angew. Chem. 2003, 115, 1604-1606).

In one embodiment, the polymers according to the invention consist only of one or more type of repeating units of formula I. In a preferred embodiment, the polymers according to the invention consist of precisely one type of repeating unit of formula I (homopolymers).

According to the present invention the term "polymer" comprises polymers as well as oligomers, wherein a polymer is a molecule of high relative molecular mass, the structure of which essentially comprises the repetition of units derived, actually or conceptually, from molecules of low relative molecular mass and an oligomer is a molecule of intermediate molecular mass, the structure of which essentially comprises a small plurality of units derived, actually or conceptually, from molecules of lower relative molecular mass. A molecule is regarded as having a high relative molecular mass if it has properties which do not vary significantly with the removal of one or a few of the units. A molecule is regarded as having an intermediate molecular mass if it has properties which do vary significantly with the removal of one or a few of the units.

According to the present invention a homopolymer is a polymer derived from one species of (real, implicit, or hypothetical) monomer. Many polymers are made by the mutual reaction of complementary monomers. These monomers can readily be visualized as reacting to give an "implicit monomer", the homopolymerisation of which would give the actual product, which can be regarded as a homopolymer. Some polymers are obtained by chemical modification of other polymers, such that the structure of the macromolecules that constitute the resulting polymer can be thought of having been formed by the homopolymerisation of a hypothetical monomer.

Accordingly a copolymer is a polymer derived from more than one species of monomer, e.g. bipolymer, terpolymer, quaterpolymer, etc.

The oligomers of this invention have a weight average molecular weight of <2,000 Daltons. The polymers of this invention preferably have a weight average molecular weight of 2,000 Daltons or greater, especially 2,000 to 2,000,000 Daltons, more preferably 10,000 to 1,000,000 and most preferably 20,000 to 500,000 Daltons. Molecular weights are determined according to gel permeation chromatography using polystyrene standards.

The present invention is illustrated in more detail on the basis of an especially preferred embodiment below, but should not be limited thereto. In said embodiment the polymer is a polymer of formula

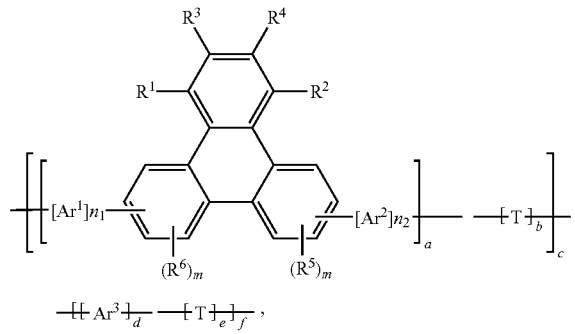

(VII)

wherein
$Ar^1$, $n_1$, $Ar^2$, $n_2$, $R^1$, $R^2$, $R^3$, $R^4$, $R^5$, $R^6$ and m are as defined above, T and $Ar^3$ are as defined in WO06/097419, wherein $Ar^3$ can also be a repeating unit of formula

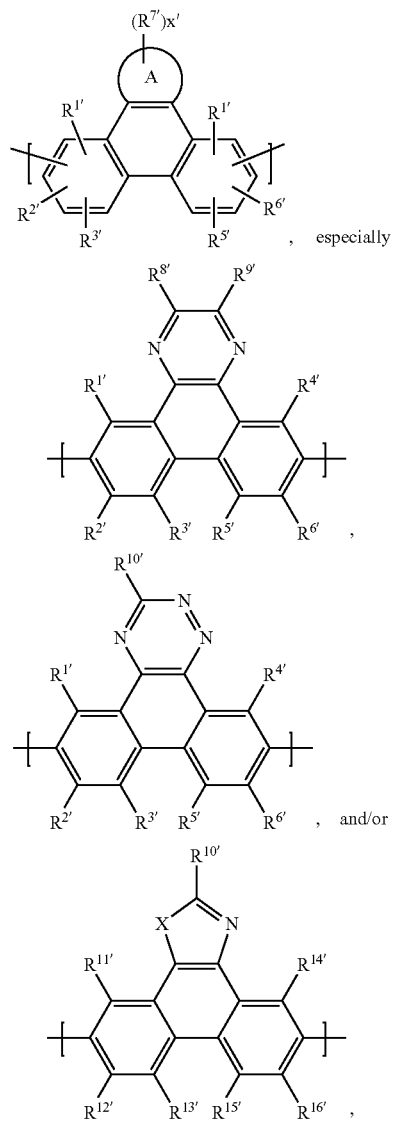

, especially

, and/or

,

-continued

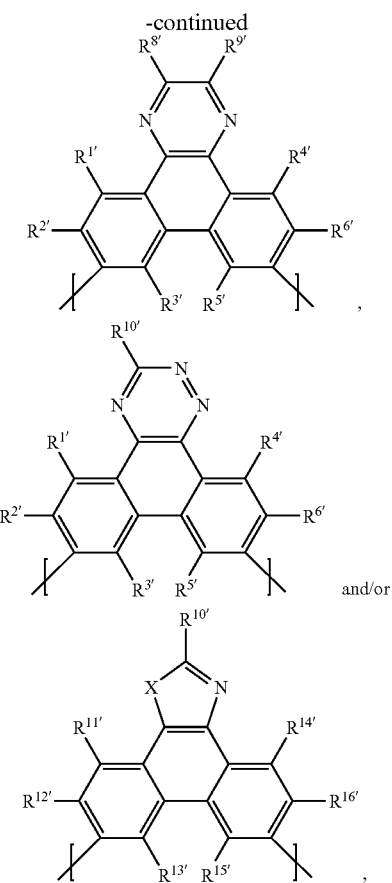

and/or as described in WO06/097419, wherein

R$^{7'}$ is an organic substituent, wherein two or more substituents R$^{7'}$ in the same molecule may have different meanings, or can form together an aromatic, or heteroaromatic ring, or ring system, and X' is 0, or an integer of 1 to 5.

A is a 5-, 6-, or 7-membered heteroaromatic ring, containing one heteroatom selected from nitrogen, oxygen and sulphur, which can be substituted and/or can be part of a fused aromatic or heteroaromatic ring system, R$^{1'}$ and R$^{4'}$ are hydrogen, R$^{2'}$, R$^{3'}$ R$^{5'}$ and R$^{6'}$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, $C_7$-$C_{25}$aralkyl, or a group —X$^2$—R$^{18'}$, R$^{8'}$ and R$^{9'}$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or a group —X$^2$—R$^{18'}$, or two substituents R$^{2'}$ and R$^{3'}$ and/or R$^{5'}$ and R$^{6'}$, which are adjacent to each other, together form a group

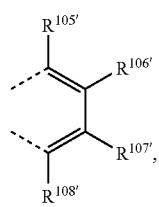

or two substituents R$^{5'}$ and R$^{3'}$, which are adjacent to each other, together form a group

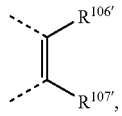

or

R$^8$ and R$^9$ together form a group

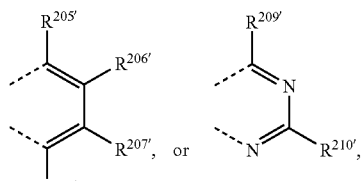

wherein R$^{205'}$, R$^{206'}$, R$^{207'}$, R$^{208'}$ R$^{209'}$ and R$^{210'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, R$^{10'}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —X$^2$—R$^{18'}$, wherein X$^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and R$^{18'}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —NR$^{25'}$R$^{26'}$;

X' is O, S, or NR$^{17'}$,

R$^{11'}$ and R$^{14'}$ are hydrogen,

R$^{12'}$, R$^{13'}$, R$^{15'}$ and R$^{16'}$ are hydrogen,

R$^{17'}$ is $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—; or two substituents R$^{11'}$ and R$^{12'}$, and/or R$^{14'}$ and R$^{16'}$, R$^{12'}$ and R$^{13'}$ and/or R$^{15'}$ and R$^{16'}$, which are adjacent to each other, together form a group

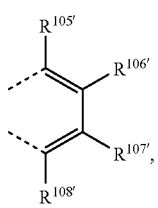

or two substituents R$^{15'}$ and R$^{13'}$, which are adjacent to each other, together form a group

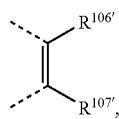

wherein $R^{105'}$ $R^{106'}$, $R^{107'}$ and $R^{108'}$ are independently of each other H, or $C_1$-$C_8$alkyl, D, E and G are as defined above;

a is 1,
b is 0, or 1,
c is 0.005 to 1,
d is 0, or 1,
e is 0, or 1, wherein e is not 1, if d is 0,
f is 0.995 to 0, wherein the sum of c and f is 1.

$Ar^3$ is preferably selected from repeating units of formula:

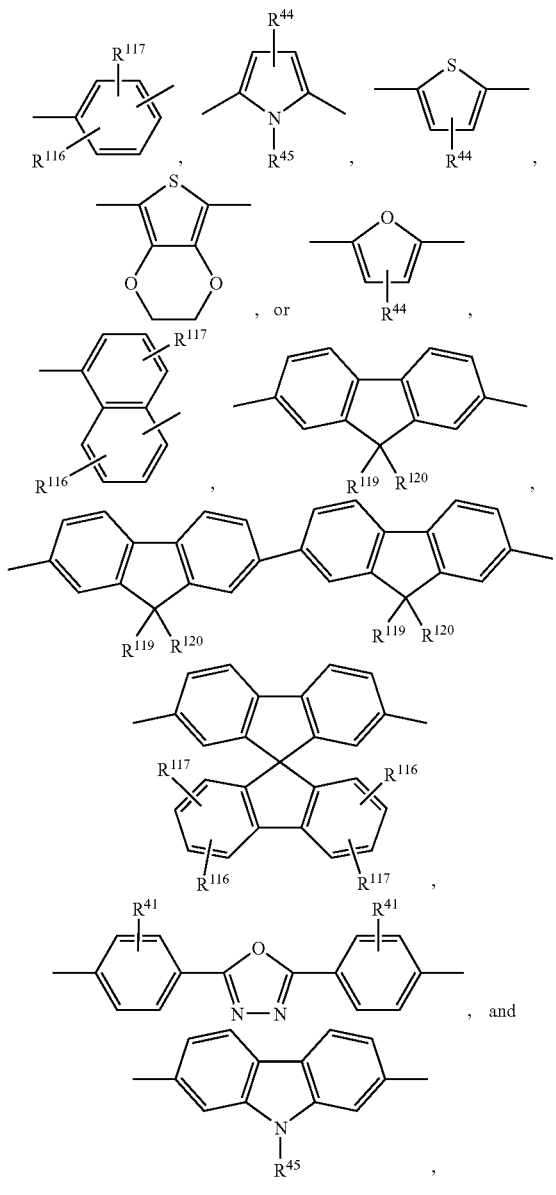

wherein
$R^{44}$ and $R^{41}$ are hydrogen, $C_1$-$C_{18}$alkyl, or $C_1$-$C_{18}$alkoxy, and
$R^{45}$ is H, $C_1$-$C_{18}$alkyl, or $C_1$-$C_{18}$alkyl which is substituted by E and/or interrupted by D, especially $C_1$-$C_{18}$alkyl which is interrupted by —O—,
$R^{116}$ and $R^{117}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$,
$R^{119}$ and $R^{120}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein
$R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or
$R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and
$R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, wherein G, D and E are as defined above.

The repeating units T are in particular selected from the following group VI:

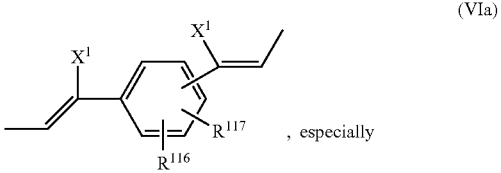, especially (VIa)

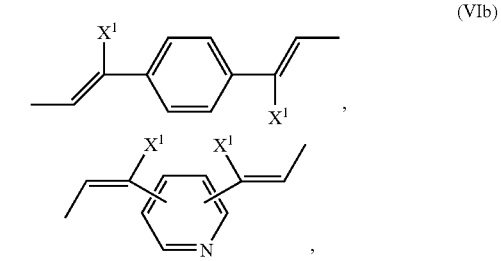 (VIb)

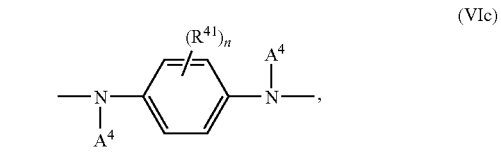 (VIc)

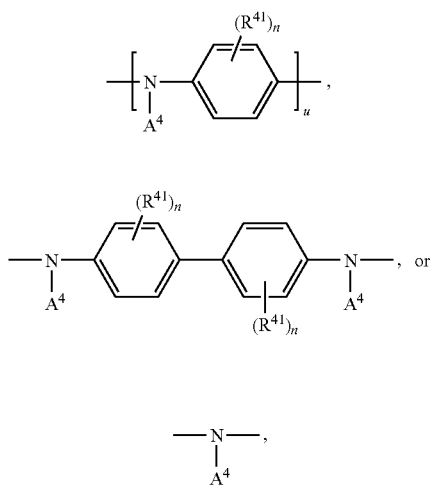

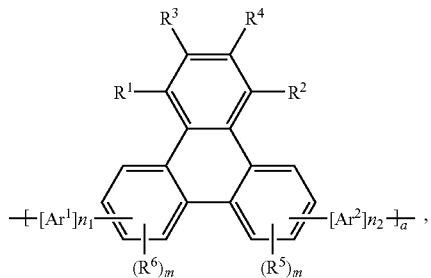

wherein $Ar^1$, $n_1$, $Ar^2$, $n_2$, $R^1$, $R^2$, $R^3$, $R^4$, $R^5$, $R^6$ and m are as defined above. In said aspect homopolymers consisting of repeating units of formula IIIa are preferred and homopolymers consisting of repeating units of formula IIa are most preferred.

Copolymers of formula VII, involving repeating units of formula I and —$Ar^3$— (a=1, c=0.995 to 0.005, b=0, d=1, e=0, f=0.005 to 0.995), can be obtained by nickel coupling reactions:

wherein $X^{10}$ is a repeating unit of formula I, especially II and III, very especially IIa and IIIa, c, f and $Ar^3$ are as defined above.

Polymerization processes involving only dihalo-functional reactants may be carried out using nickel coupling reactions. One such coupling reaction was described by Colon et al. in J. Pol. Sci., Part A, Polymer Chemistry Edition 28 (1990) 367, and by Colon et al. in J. Org. Chem. 51 (1986) 2627. The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in Bull. Chem. Soc. Jpn, 63 (1990) 80 wherein an organosoluble iodide was used as an accelerator.

Another nickel-coupling reaction was disclosed by Yamamoto in Progress in Polymer Science 17 (1992) 1153 wherein a mixture of dihaloaromatic compounds was treated with an excess amount of nickel (1,5-cyclooctadiene) complex in an inert solvent. All nickel-coupling reactions when applied to reactant mixtures of two or more aromatic dihalides yield essentially random copolymers. Such polymerization reactions may be terminated by the addition of small amounts of water to the polymerization reaction mixture, which will replace the terminal halogen groups with hydrogen groups. Alternatively, a monofunctional aryl halide may be used as a chain-terminator in such reactions, which will result in the formation of a terminal aryl group.

Nickel-coupling polymerizations yield essentially homopolymers or random copolymers comprising units of formula I and units derived from other co-monomers.

Homopolymers of formula VII, wherein a=1, c=1, b=0, d=1, e=0, f=1, can be obtained, for example, by the Suzuki reaction:

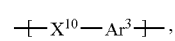

wherein $X^{10}$ and $Ar^3$ are as defined above.

wherein $X^1$ is a hydrogen atom, or a cyano group, $R^{116}$ and $R^{117}$ are as defined above, $R^{41}$ can be the same or different at each occurrence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, —C(=O)—O—, or —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not in neighbourhood to each other could be replaced by —$NR^{45'}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, $R^{45'}$ is H, a $C_1$-$C_{25}$alkyl group, or a $C_4$-$C_{18}$cycloalkyl group, n can be the same or different at each occurrence and is 0, 1, 2, or 3, especially 0, 1, or 2, very especially 0 or 1, and u is 1, 2, 3, or 4;

$A^4$ is a $C_6$-$C_{24}$aryl group, a $C_2$-$C_{30}$heteroaryl group, especially phenyl, naphthyl, anthryl, biphenylyl, 2-fluorenyl, phenanthryl, or perylenyl, which can be substituted by one or more non-aromatic groups $R^{41}$, wherein T is preferably a repeating unit of formula VIa, VIb or VIf. Homopolymers of formula VII, wherein a=1, b=0, c=1, d=0, e=0, f=0, are, for example, obtained by nickel coupling reactions, especially the Yamamoto reaction:

The condensation reaction of an aromatic boronate and a halogenide, especially a bromide, commonly referred to as the "Suzuki reaction", is tolerant of the presence of a variety of organic functional groups as reported by N. Miyaua and A. Suzuki in Chemical Reviews, Vol. 95, pp. 457-2483 (1995). This reaction can be applied to preparing high molecular weight polymers and copolymers. Preferred catalysts are 2-dicyclohexylphosphino-2',6'-di-alkoxybiphenyl/palladium (II) acetates. An especially preferred catalyst is 2-dicyclohexylphosphino-2',6'-di-methoxybiphenyl (sPhos)/palladium(II)acetate.

To prepare polymers corresponding to formula VIIc, a dihalogenide, such as a dibromide or dichloride, especially a dibromide corresponding to formula Br—$X^{10}$—Br is reacted with an equimolar amount of a diboronic acid or diboronate corresponding to formula

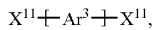

wherein $X^{11}$ is independently in each occurrence —$B(OH)_2$, —$B(OY^{11})_2$ or

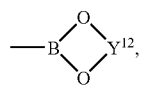

wherein $Y^{11}$ is independently in each occurrence a $C_1$-$C_{10}$alkyl group and $Y^{12}$ is independently in each occurrence a $C_2$-$C_{10}$alkylene group, such as —$CY^{13}Y^{14}$—$CY^{15}Y^{16}$—, or —$CY^{17}Y^{18}$—$CY^{19}Y^{20}$—$CY^{21}Y^{22}$—, wherein $Y^{13}, Y^{14}, Y^{15}, Y^{16}, Y^{17}, Y^{18}, Y^{19}, Y^{20}, Y^{21}$ and $Y^{22}$ are independently of each other hydrogen, or a $C_1$-$C_{10}$alkyl group, especially —$C(CH_3)_2C(CH_3)_2$—, or —$C(CH_3)_2CH_2C(CH_3)_2$—, under the catalytic action of Pd and a phosphine ligand, especially triphenylphosphine. The reaction is typically conducted at about 70° C. to 180° C. in an aromatic hydrocarbon solvent such as toluene. Other solvents such as dimethylformamide and tetrahydrofuran can also be used alone, or in mixtures with an aromatic hydrocarbon. An aqueous base, preferably sodium carbonate, potassium carbonate, $K_3PO_4$, or bicarbonate, is used as the HBr scavenger. Depending on the reactivities of the reactants, a polymerization reaction may take 2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

If desired, a monofunctional aryl halide or aryl boronate may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

Homopolymers of formula VII, wherein a=1, c=1, b=1, d=0, e=0, f=0, can be obtained, for example by the Heck reaction:

wherein $X^{10}$ and T are as defined above.

Polyphenylenethenylene derivatives and polyphenylenethynylene derivatives can be obtained by polymerization of divinyl or diethinyl compounds with dihalogen compounds by the Heck reaction (R. F. Heck, Palladium Reagents in Organic Synthesis, Academic Press, New York 1985, pp. 179; L. S. Hegedus, Organometalics in Synthesis, Ed. M. Schlosser, Wiley, Chichester, UK 1994, pp. 383; Z. Bao, Y. Chen, R. Cai, L. Yu, Macromolecules 26 (1993) pp. 5281; W.-K. Chan, L. Yu, Macromolecules 28 (1995) pp. 6410; A. Hilberer, H.-J. Brouwer, B.-J. van der Scheer, J. Wildeman, G. Hadziioannou, Macromolecules 1995, 28, 4525) and the Sonogaschira reaction (Dmitri Gelman and Stephen L. Buchwald, Angew. Chem. Int. Ed. 42 (2003) 5993-5996; Rik R. Tykwinski, Angew. Chem. 115 (2003) 1604-1606; Jason M. Nolan and Daniel L. Comins, J. Org. Chem. 68 (2003) 3736-3738; Jiang Cheng et al., J. Org. Chem. 69 (2004) 5428-5432; Zolta'n Nova'k et al., Tetrahedron 59 (2003) 7509-7513):

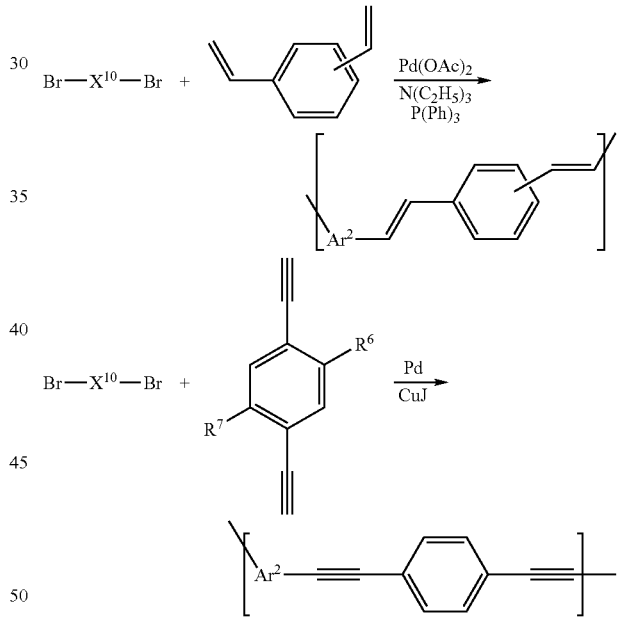

(Random) copolymers of formula VII, wherein a is 1, b is 1, c is 0.005 to 0.995, d is 1, e is 1, f is 0.995 to 0.005, wherein the sum of c and f is 1, can also be obtained by the Heck reaction:

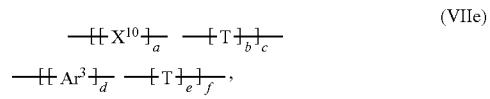

wherein a, b, c, d, e, f, $X^{10}$, $Ar^3$ and T are as defined above.

The polymers containing groups of formulas (I) may be prepared by any suitable process, but are preferably prepared by the processes described above.

The polymers of the present invention can optionally comprise end moieties $E^1$, wherein $E^1$ is an aryl moiety which may optionally be substituted with a reactive group capable of undergoing chain extension or crosslinking, or a tri($C_1$-$C_{18}$) alkylsiloxy group. As used herein, a reactive group capable of undergoing chain extension or crosslinking refers to any group which is capable of reacting with another of the same group or another group so as to form a link to prepare polymers. Preferably, such reactive group is a hydroxy, glycidyl ether, acrylate ester, methacrylate ester, ethenyl, ethynyl, maleimide, naphthimide, oxetane, trifluorovinyl ether moiety or a cyclobutene moiety fused to the aromatic ring of $E^1$.

The polymers of the present invention, where $E^1$ are reactive groups as defined above, are capable of crosslinking to form solvent resistant, heat-resistant films at 100° C. or more, more preferably at 150° C. or more. Preferably, such crosslinking occurs at 350° C. or less, more preferably 300° C. or less and most preferably 250° C. or less. The crosslinkable polymers of the invention are stable at 100° C. or more and more preferably 150° C. or more. "Stable" as used herein means that such polymers do not undergo crosslinking or polymerization reactions at or below the stated temperatures. If a crosslinkable material is desired, $E^1$ is preferably a vinylphenyl, an ethynylphenyl, or 4-(or 3-)benzocyclobutenyl radical. In another embodiment, $E^1$ is selected from a group of phenolic derivatives of the formula —$C_6H_4$—O—Y, wherein Y is —H, —CN,

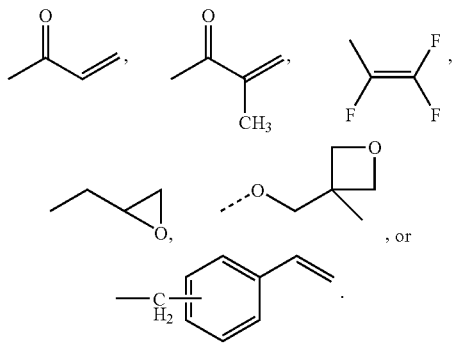

If desired, the cross-linkable groups can be present in other parts of the polymer chain. For example, one of the substituents of the co-monomer T may be a crosslinkable group $E^1$.

The end-capping agent $E^1$-$X^{12}$ ($E^1$ is as defined above and $X^{12}$ is either Cl or Br) is incorporated into the polymers of the present invention under the condition in which the resulting polymers are substantially capped by the reactive group $E^1$. The reactions useful for this purpose are the nickel-coupling, Heck reactions and Suzuki reactions described above. The average degree of polymerization is controlled by the mole ratio of monomers to end-capping agent.

The polymers according to the invention can be worked up by known methods which are familiar to the person skilled in the art, as described, for example, in D. Braun, H. Cherdron, H. Ritter, Praktikum der makromolekularen Stoffe, $1^{st}$ Edn., Wiley VCH, Weinheim 1999, p. 68-79 or R. J. Young, P. A. Lovell, Introduction to Polymers, Chapman & Hall, London 1991. For example, the reaction mixture can be filtered, diluted with aqueous acid, extracted and the crude product obtained after drying and stripping-off of the solvent can be further purified by reprecipitation from suitable solvents with addition of precipitants. Residual palladium can be removed by using activated carbon, chromatography etc. Advantageously, the residual palladium could be reduced to <3 ppm by washing the crude organic solvent layer containing the polymer with an aqueous solution of L-cysteine at room temperature to the boiling point of the organic solvent, especially by washing a toluene layer containing the polymer with an aqueous solution of L-cysteine at 85 to 90° C., optionally followed by washing with a solution of L-cysteine and sodium thiosulfate at 78 to 82° C. (Mahavir Prashad, Yugang Liu, Oljan Repicoe, Adv. Synth. Catal. 2003, 345, 533-536; Christine E. Garrett, Kapa Prasad, Adv. Synth. Catal. 2004, 346, 889-900). Additionally the Pd can be removed by washing the polymer with an aqueous NaCN solution as described in U.S. Pat. No. 6,956,095. Polymer-analogous reactions can subsequently be carried out for further functionalization of the polymer. Thus, for example, terminal halogen atoms can be removed reductively by reduction with, for example, $LiAlH_4$ (see, for example, J. March, Advanced Organic Chemistry, $3^{rd}$ Edn. McGraw-Hill, p. 510).

Another aspect of this invention is related to polymer blends containing 1 to 99 percent of at least one containing polymers comprising a unit of formula I. The remainder 1 to 99 percent of the blend is composed of one or more polymeric materials selected from among chain growth polymers such as polystyrene, polybutadiene, poly(methyl methacrylate), and poly(ethylene oxide); step-growth polymers such as phenoxy resins, polycarbonates, polyamides, polyesters, polyurethanes, and polyimides; and crosslinked polymers such as crosslinked epoxy resins, crosslinked phenolic resins, crosslinked acrylate resins, and crosslinked urethane resins. Examples of these polymers may be found in Preparative Methods of Polymer Chemistry, W. R. Sorenson and T. W. Campbell, Second Edition, Interscience Publishers (1968). Also may be used in the blends are conjugated polymers such as poly(phenylene vinylene), substituted poly(phenylene vinylene)s, substituted polyphenylenes and polythiophenes. Examples of these conjugated polymers are given by Greenham and Friend in Solid State Physics, Vol. 49, pp. 1-149 (1995).

In a preferred embodiment the present invention is directed to polymers of formula

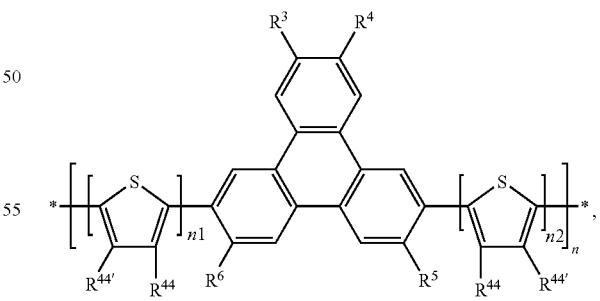

wherein $R^3$, $R^4$, $R^5$ and $R^6$ are independently of each other H, $C_1$-$C_{25}$alkyl, which can optionally be interrupted by O, or $C_1$-$C_{25}$alkoxy, which can optionally be interrupted by O, $R^{44}$ and $R^{44'}$ are independently of each other H, $C_1$-$C_{25}$alkyl, which can optionally be interrupted by O, or $C_1$-$C_{25}$alkoxy, which can optionally be interrupted by O, and n1 and n2 are independently of each other 1, 2, or 3.

In an especially preferred embodiment the present invention is directed to polymers of formula

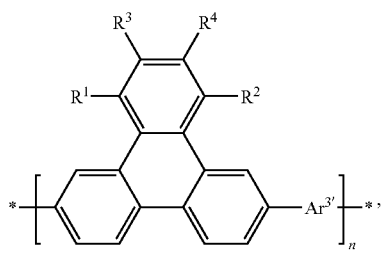

wherein $R^1$, $R^2$, $R^3$ and $R^4$ are independently of each other

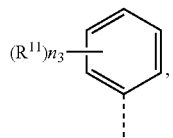

wherein $n_3$ is 0, or an integer 1, 2, or 3, especially 0, or 1; and $R^{11}$ can be the same or different and is H, $C_1$-$C_{25}$alkyl, which can be optionally interrupted by O, or $C_1$-$C_{25}$alkoxy, which can be optionally interrupted by O, and

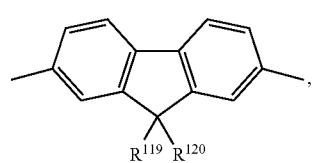

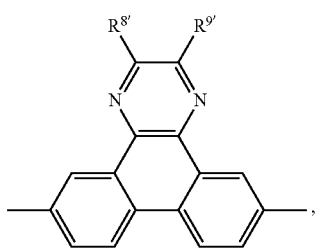

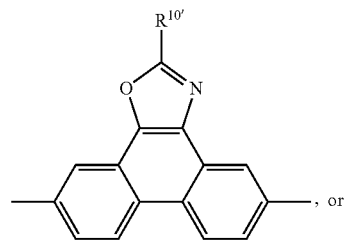

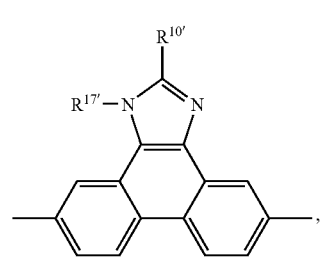

Ar$^{3'}$ is
wherein
$R^{44}$, $R^{116}$, $R^{117}$, $R^{119}$ and $R^{120}$ are as defined above,
$R^{8'}$ and $R^{9'}$ are independently of each other

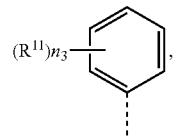

wherein $n_3$ and $R^{11}$ are as defined above, $R^{17'}$ is $C_1$-$C_{25}$alkyl, which can be optionally interrupted by O, and $R^{10'}$ is $R^{8'}$, or

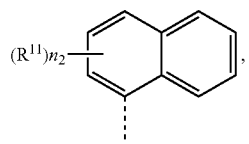

wherein n2 is 0, 1, or 2.
The following polymers are especially preferred:

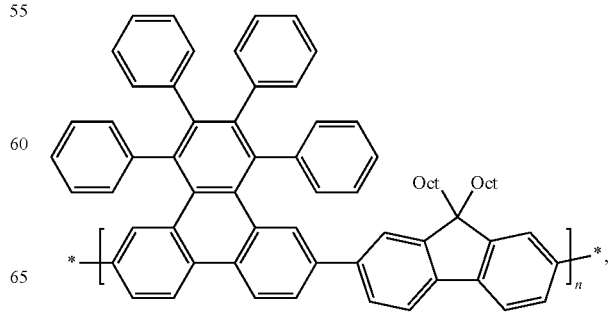

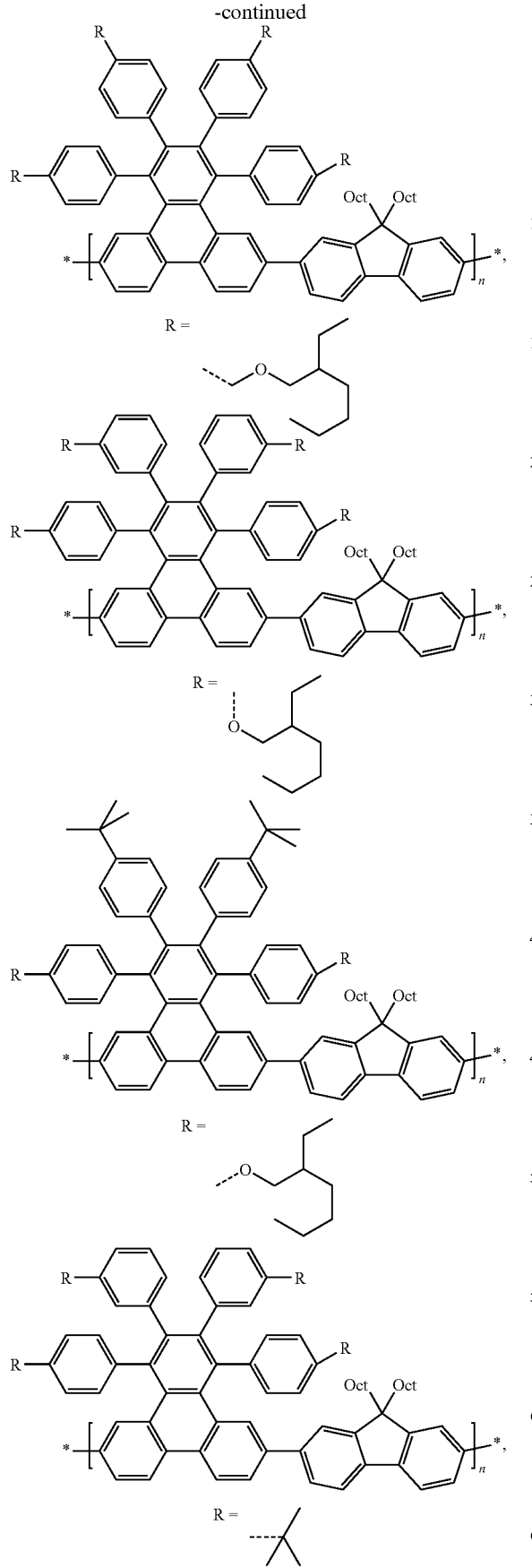
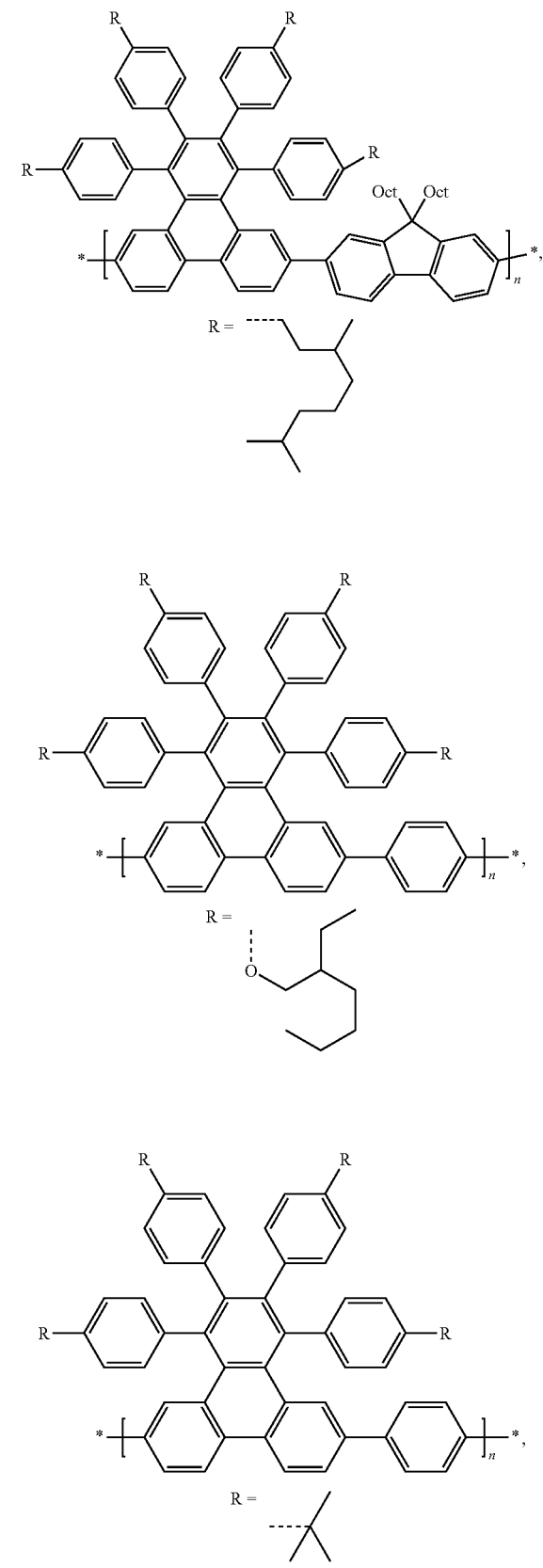

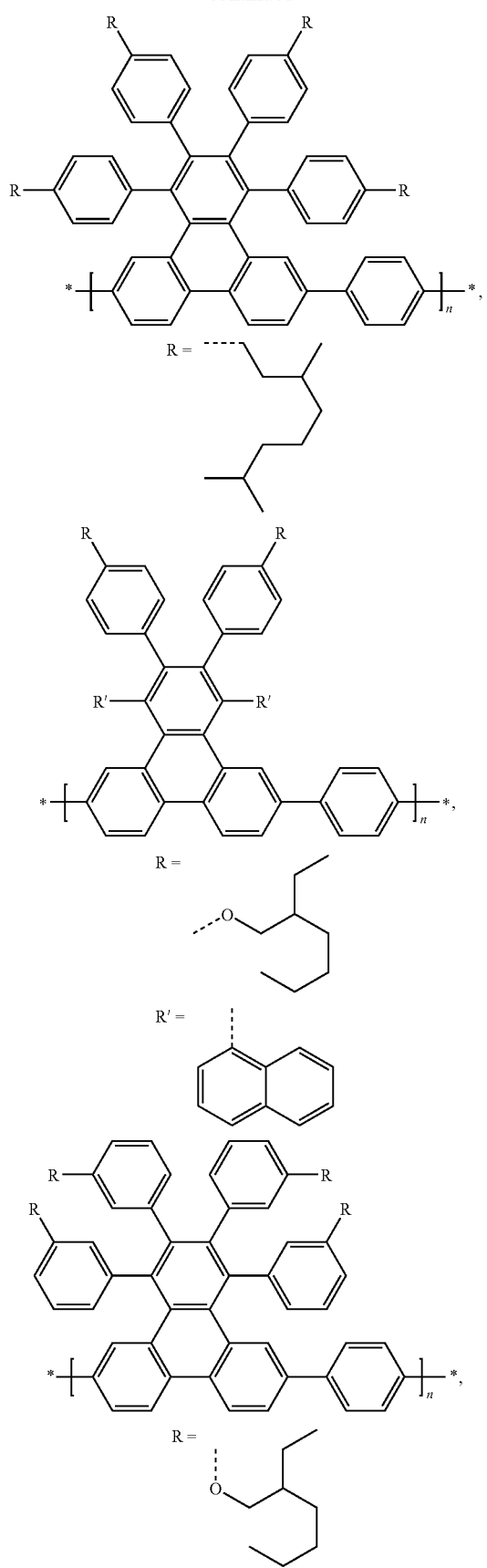
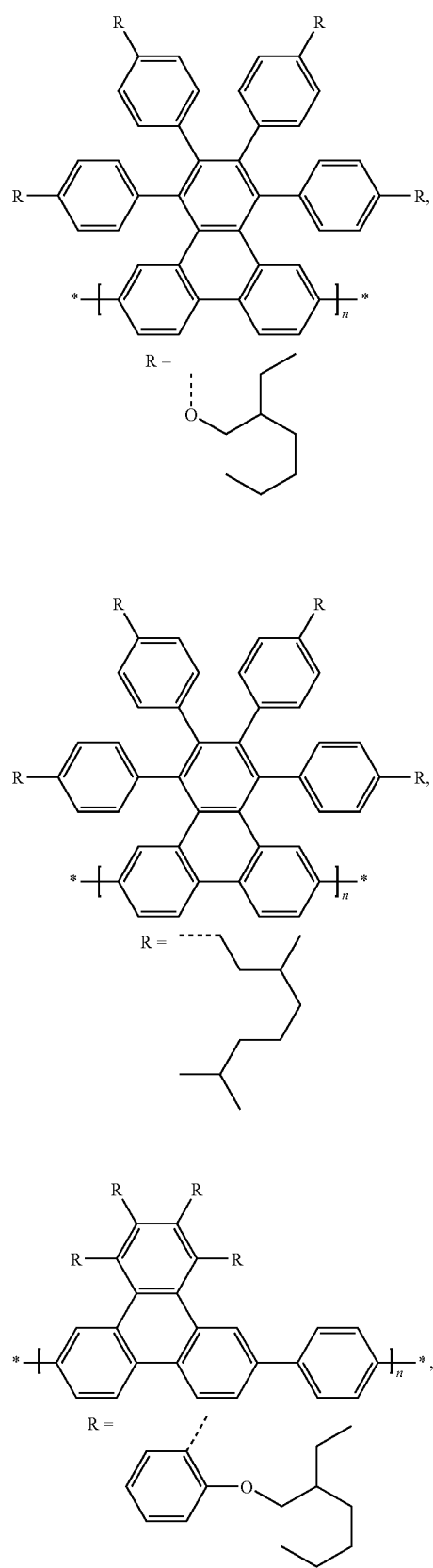

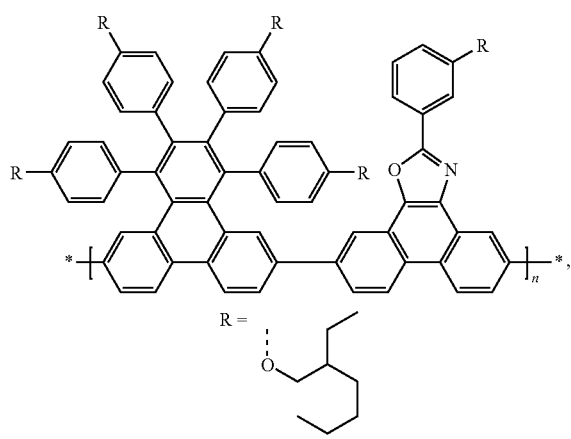
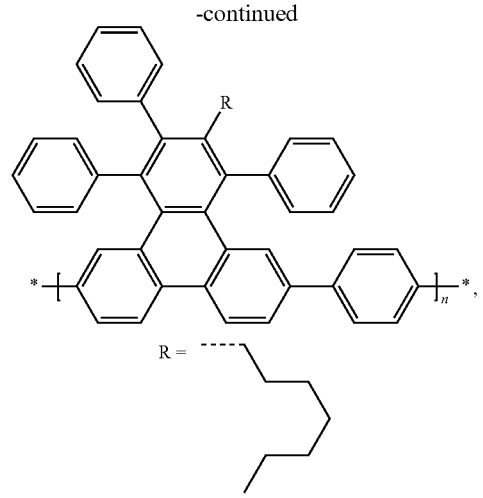
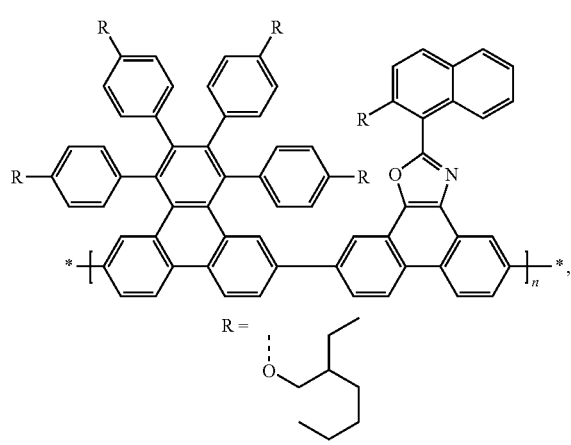
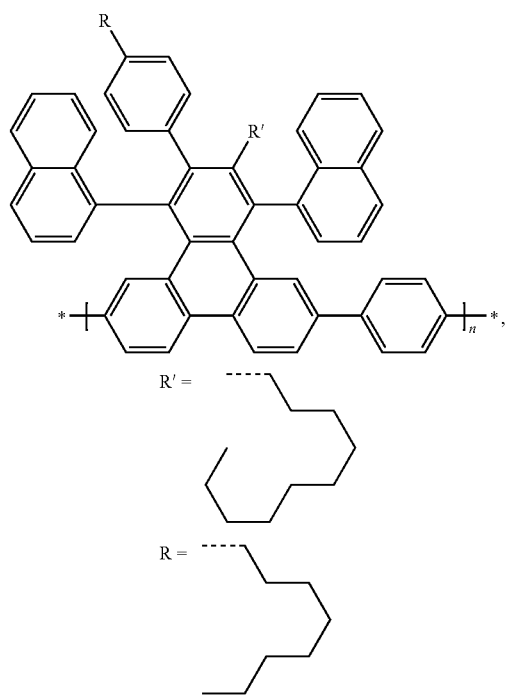
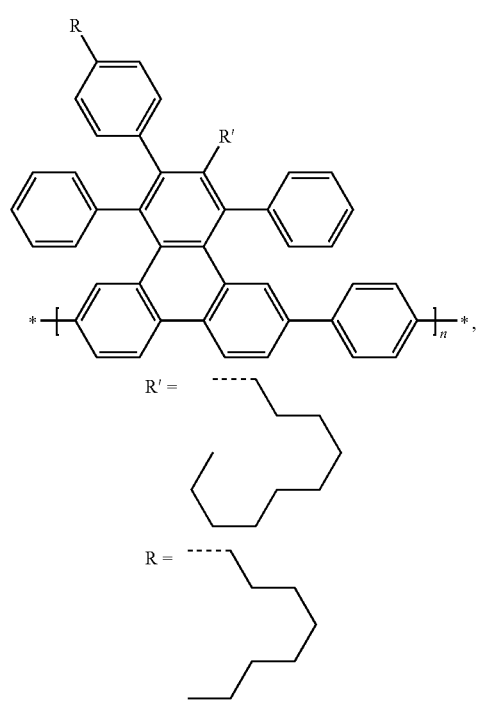
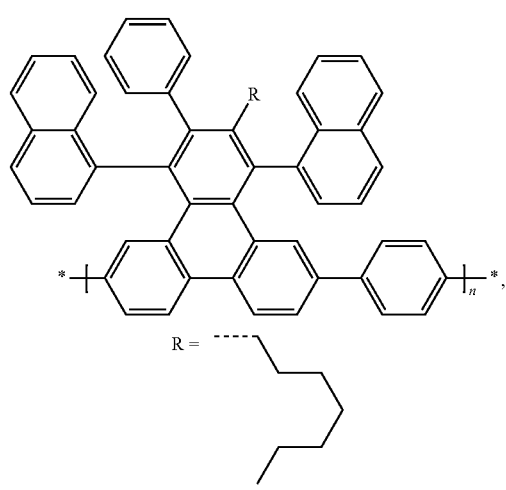

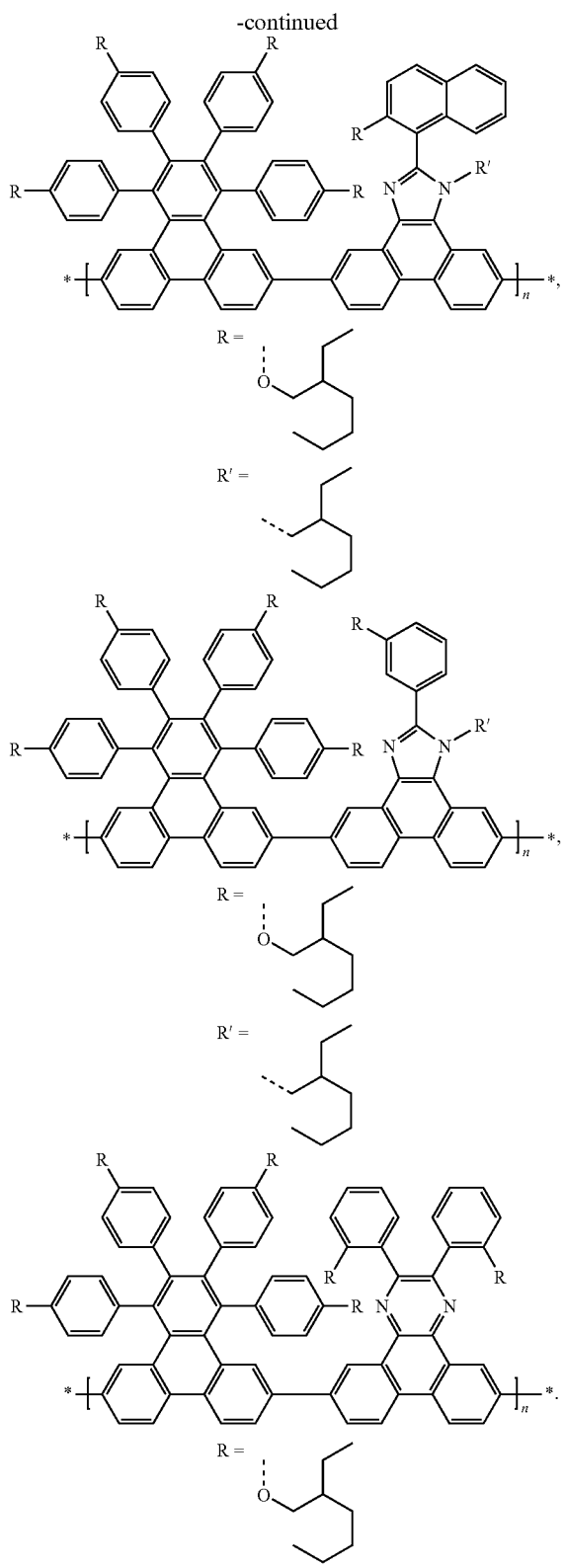

The polymers of the present invention can show high photoluminescence and/or electroluminescence.

Halogen is fluorine, chlorine, bromine and iodine.

$C_1$-$C_{25}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The terms "haloalkyl, haloalkenyl and haloalkynyl" mean groups given by partially or wholly substituting the above-mentioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

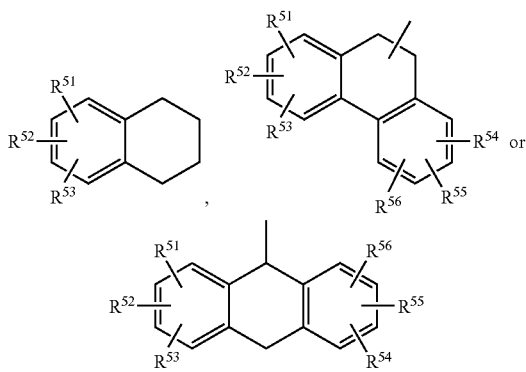

in particular

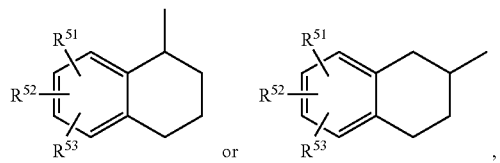

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ωdimethyl-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$carbamoyl radical, preferably $C_{18}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diarylgroups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

If a substituent, such as, for example $R^7$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(OR$^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;
$C_1$-$C_8$alkylene-COO—$R^z$, e.g. $CH_2COOR^z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—C($CH_3$)=$CH_2$.

Preferred arylene radicals are 1,4-phenylene, 2,5-tolylene, 1,4-naphthylene, 1,9 antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

Another aspect of the invention is the films formed from the polymers of the invention. Such films can be used in polymeric light-emitting diodes (PLEDs). Preferably, such films are used as emitting layers. These films may also be used as protective coatings for electronic devices and as fluorescent coatings. The thickness of the coating or film is dependent upon the ultimate use. Generally, such thickness can be from 0.01 to 200 microns. In that embodiment wherein the coating is used as a fluorescent coating, the coating or film thickness is from 10 to 200 microns. In that embodiment where the coatings are used as electronic protective layers, the thickness of the coating can be from 5 to 20 microns. In that embodiment where the coatings are used in a polymeric light-emitting diode, the thickness of the layer formed is 0.01 to 0.5 microns. The polymers of the invention form good pinhole- and defect-free films. Such films can be prepared by means well known in the art including spin-coating, spray-coating, dip-coating and roller-coating. Such coatings are prepared by a process comprising applying a composition to a substrate and exposing the applied composition to conditions such that a film is formed. The conditions which form a film depend upon the application technique. Preferably, the solution contains from 0.1 to 10 weight percent of the polymers. This composition is applied to the appropriate substrate by the desired method and the solvent is allowed to evaporate. Residual solvent may be removed by vacuum and/or by heat-drying. The films are preferably substantially uniform in thickness and substantially free of pinholes. In another embodiment, the polymers may be partially cured. This is known as B-staging.

A further embodiment of the present invention is directed to an electronic device or a component therefore, comprising a substrate and a polymer according to the present invention.

In such a device the polymers according to the present invention are used as electroluminescent material. For the purposes of the present invention, the term "electroluminescent material" is taken to mean materials which can be used as or in an active layer in an electroluminescent device. The term "active layer" means that the layer is capable of emitting light (light-emitting layer) on application of an electric field and/or that it improves the injection and/or transport of the positive and/or negative charges (charge injection or charge transport layer). The invention therefore also relates to the use of the polymers according to the invention as electroluminescent material. The invention furthermore relates to an electroluminescent material which comprises the polymers according to the invention. Electroluminescent devices are used, for example, as self-illuminating display elements, such as control lamps, alphanumeric displays, signs and in opto-electronic couplers.

A device according to the present invention may be prepared in accordance with the disclosure of WO99/48160, the contents of which are incorporated by reference. Polymers according to the present invention may be present in the device as the sole light emitting polymer or as a component in a blend further comprising hole and/or electron transporting polymers. Alternatively, the device may comprise distinct layers of a polymer of the present invention, a hole transporting polymer and/or an electron transporting polymer.

In one embodiment the electronic device comprises an electroluminescent device, which comprises
(a) a charge injecting layer for injecting positive charge carriers,
(b) a charge injecting layer for injecting negative charge carriers,
(c) a light-emissive layer located between the layers (a) and (b) comprising a polymer according to the present invention.

The layer (a) may be a positive charge carrier transport layer which is located between the light emissive layer (c) and an anode electrode layer, or may be an anode electrode layer. The layer (b) may be a negative charge carrier transport layer which is located between the light emissive layer (c) and an cathode electrode layer, or may be an cathode electrode layer. Optionally, an organic charge transport layer can be located between the light emissive layer (c) and one of the charge carrier injecting layers (a) and (b).

The EL device emits light in the visible electromagnetic spectrum between 400 nm and 780 nm, preferably between 430 nm and 470 nm for a blue color, preferably between 520 nm and 560 nm for a green color, preferably between 600 nm and 650 nm for a red color. By incorporating specific repeating units in the backbone of the polymer the emission can be even shifted to the near infrared (NIR, >780 nm).

It will be appreciated that the light emissive layer may be formed from a blend or mixture of materials including one or more polymers according to the present invention, and optionally further different polymers. The further different polymers may be so-called hole transport polymers (i.e. to improve the efficiency of hole transport to the light-emissive material) or electron-transport polymers (i.e. to improve the efficiency of electron transport to the light-emissive material). Preferably, the blend or mixture would comprise at least 0.1% by weight of a polymer according to the present invention, preferably at least 0.5% by weight, more preferably at least 1% by weight.

An organic EL device typically consists of an organic film sandwiched between an anode and a cathode such that when a positive bias is applied to the device, holes are injected into the organic film from the anode, and electrons are injected into the organic film from the cathode. The combination of a hole and an electron may give rise to an exciton, which may undergo radiative decay to the ground state by liberating a photon. In practice the anode is commonly an mixed oxide of tin and indium for its conductivity and transparency. The mixed oxide (ITO) is deposited on a transparent substrate such as glass or plastic so that the light emitted by the organic film may be observed. The organic film may be the composite of several individual layers each designed for a distinct function. Since holes are injected from the anode, the layer next to the anode needs to have the functionality of transporting holes. Similarly, the layer next to the cathode needs to have the functionality of transporting electrons. In many instances, the hole-(electron) transporting layer also acts as the emitting layer. In some instances one layer can perform the combined functions of hole and electron transport and light emission. The individual layers of the organic film may be all polymeric in nature or combinations of films of polymers and films of small molecules deposited by thermal evaporation. It is preferred that the total thickness of the organic film be less than 1000 nanometers (nm). It is more preferred that the total thickness be less than 500 nm. It is most preferred that the total thickness be less than 300 nm. It is preferred that the thickness of the active (light emitting) layer be less than 400 nanometers (nm). It is more preferred that the thickness is in the range of from 40 to 160 nm.

The ITO-glass, which serves as the substrate and the anode, may be used for coating after the usual cleaning with detergent, organic solvents and UV-ozone treatment. It may also be first coated with a thin layer of a conducting substance to facilitate hole injection. Such substances include copper phthalocyanine, polyaniline (PANI) and poly(3,4-ethylene-dioxy-thiophene) (PEDOT); the last two in their (doped) conductive forms, doped, for example, with $FeCl_3$ or $Na_2S_2O_8$. They contain poly(styrenesulfonic acid) (PSS) as counter-ion to ensure water solubility. It is preferred that the thickness of this layer be 200 nm or less; it is more preferred that the thickness be 100 nm or less.

In the cases where a hole-transporting layer is used, the polymeric arylamines described in U.S. Pat. No. 5,728,801, may be used. Other known hole-conducting polymers, such as polyvinylcarbazole, may also be used. The resistance of this layer to erosion by the solution of the copolymer film which is to be applied next is obviously critical to the successful fabrication of multi-layer devices. The thickness of this layer may be 500 nm or less, preferably 300 nm or less, most preferably 150 nm or less.

In the case where an electron-transporting layer is used, it may be applied either by thermal evaporation of low molecular weight materials or by solution coating of a polymer with a solvent that would not cause significant damage to the underlying film.

Examples of low molecular weight materials include the metal complexes of 8-hydroxyquinoline (as described by Burrows et al. in Appl. Phys. Lett. 64 (1994) 2718-2720), metallic complexes of 10-hydroxybenzoquinoline (as described by Hamada et al. in Chem. Lett. (1993) 906-906), 1,3,4-oxadiazoles (as described by Hamada et al. in Optoelectronics-Devices and Technologies 7 (1992) 83-93), 1,3,4-triazoles (as described by Kido et al. in Chem. Lett. (1996) 47-48), and dicarboximides of perylene (as described by Yoshida et al. in Appl. Phys. Lett. 69 (1996) 734-736).

Polymeric electron-transporting materials are exemplified by 1,3,4-oxadiazole-containing polymers (as described by Li et al. in J. Chem. Soc. (1995) 2211-2212, by Yang and Pei in J. Appl. Phys. 77 (1995) 4807-4809), 1,3,4-triazole-containing polymers (as described by Strukelj et al. in Science 267 (1995) 1969-1972), quinoxaline-containing polymers (as described by Yamamoto et al. in Jpn. J. Appl. Phys. 33 (1994) L250-L253, O'Brien et al. in Synth. Met. 76 (1996) 105-108), and cyano-PPV (as described by Weaver et al. in Thin Solid Films 273 (1996) 39-47). The thickness of this layer may be 500 nm or less, preferably 300 nm or less, most preferably 150 nm or less.

The cathode material may be deposited either by thermal evaporation or by sputtering. The thickness of the cathode may be from 1 nm to 10,000 nm, preferably 5 nm to 500 nm.

OLEDs made according to the present invention may include phosphorescent dopants dispersed in the device's emissive layer, capable of achieving internal quantum efficiencies approaching 100%. As used herein, the term "phosphorescence refers to emission from a triplet excited state of an organic or metal-organic molecule. High efficiency organic light emitting devices using phosphorescent dopants have been demonstrated using several different conducting host materials (M. A. Baldo et al., Nature, Vol 395, 151 (1998), C. Adachi et al., Appl. Phys. Lett., Vol. 77, 904 (2000)).

In a preferred embodiment, the electroluminescent device comprises at least one hole-transporting polymer film and a light-emitting polymer film comprised of the polymer of the invention, arranged between an anode material and a cathode material such that under an applied voltage, holes are injected from the anode material into the hole-transporting polymer film and electrons are injected from the cathode material into the light-emitting polymer films when the device is forward biased, resulting in light emission from the light-emitting layer.

In another preferred embodiment, layers of hole-transporting polymers are arranged so that the layer closest to the anode has the lower oxidation potential, with the adjacent layers having progressively higher oxidation potentials. By these methods, electroluminescent devices having relatively high light output per unit voltage may be prepared.

The term "hole-transporting polymer film" as used herein refers to a layer of a film of a polymer which when disposed between two electrodes to which a field is applied and holes are injected from the anode, permits adequate transport of holes into the emitting polymer. Hole-transporting polymers typically are comprised of triarylamine moieties. The term "light-emitting polymer film" as used herein refers to a layer of a film of a polymer whose excited states can relax to the ground state by emitting photons, preferably corresponding to wavelengths in the visible range. The term "anode material" as used herein refers to a semi-transparent, or transparent, conducting film with a work function between 4.5 electron volts (eV) and 5.5 eV. Examples are gold, silver, copper, aluminum, indium, iron, zinc, tin, chromium, titanium, vanadium, cobalt, nickel, lead, manganese, tungsten and the like, metallic alloys such as magnesium/copper, magnesium/silver, magnesium/aluminum, aluminum/indium and the like, semiconductors such as Si, Ge, GaAs and the like, metallic oxides such as indium-tin-oxide ("ITO"), ZnO and the like, metallic compounds such as CuI and the like, and furthermore, electroconducting polymers such polyacetylene, polyaniline, polythiophene, polypyrrole, polyparaphenylene and the like. Oxides and mixed oxides of indium and tin, and gold are preferred. Most preferred is ITO, especially ITO on glass, or on a plastics material, such as polyester, for example polyethylene terephthalate (PET), as substrate.

The term "cathode material" as used herein refers to a conducting film with a work function between 2.0 eV and 4.5 eV. Examples are alkali metals, earth alkaline metals, group 13 elements, silver, and copper as well as alloys or mixtures thereof such as sodium, lithium, potassium, calcium, lithium fluoride (LiF), sodium-potassium alloy, magnesium, barium, magnesium-silver alloy, magnesium-copper alloy, magnesium-aluminum alloy, magnesium-indium alloy, aluminum, aluminum-aluminum oxide alloy, aluminum-lithium alloy, indium, calcium, and materials exemplified in EP-A 499,011, such as electroconducting polymers e.g. polypyrrole, polythiophene, polyaniline, polyacetylene etc. Preferably lithium, barium, calcium, magnesium, indium, silver, aluminum, or blends and alloys of the above are used. In the case of using a metal or a metallic alloy as a material for an electrode, the electrode can be formed also by the vacuum deposition method. In the case of using a metal or a metallic alloy as a material forming an electrode, the electrode can be formed, furthermore, by the chemical plating method (see for example, Handbook of Electrochemistry, pp 383-387, Mazuren, 1985). In the case of using an electroconducting polymer, an electrode can be made by forming it into a film by means of anodic oxidation polymerization method onto a substrate, which is previously provided with an electroconducting coating.

As methods for forming said thin films, there are, for example, the vacuum deposition method, the spin-coating method, the casting method, the Langmuir-Blodgett ("LB") method, the ink jet printing method and the like. Among these methods, the vacuum deposition method, the spin-coating method, the ink jet printing method and the casting method are particularly preferred in view of ease of operation and cost.

In the case of forming the layers by using the spin-coating method, the casting method and ink jet printing method, the coating can be carried out using a solution prepared by dissolving the composition in a concentration of from 0.0001 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide and mixtures thereof.

Patterning of active matrix OLED (AMOLED) materials for large format, high resolution displays can be done using Laser Induced Thermal Imaging (LITI; Organic Light-Emitting Materials and Devices VII, edited by Zakya H. Kafafi, Paul A. Lane, Proceedings of SPIE Vol. 5519, 12-23).

The organic EL device of the present invention is seen as a future replacement technology for a flat panel display of an on-wall television set, a flat light-emitting device, such as a wall paper, a light source for a copying machine or a printer, a light source for a liquid crystal display or counter, a display signboard and a signal light and perhaps even to replace incandescent and fluorescent lamps. The polymers and compositions of the present invention can be used in the fields of an organic EL device, a photovoltaic device, an electrophotographic photoreceptor, a photoelectric converter, a solar cell, an image sensor, and the like.

Accordingly, the present invention relates also to PLEDs, organic integrated circuits (O—ICs), organic field effect transistors (OFETs), organic thin film transistors (OTFTs), organic solar cells (O—SCs), thermoelectric devices, or organic laser diodes comprising one or more of the polymers according to the present invention.

The following examples are included for illustrative purposes only and do not limit the scope of the claims. Unless otherwise stated, all parts and percentages are by weight. Weight-average molecular weight ($M_w$) and polydispersity ($M_w/M_n$=PD) are determined by Gel Permeation Chromatography (GPC) [Apparatus: $GPC_{max}$+TDA 302 from Viscotek (Houston, Tex., USA) yielding the responses form refractive index (RI), low angle light scattering (LALS), right angle light scattering (RALS) and differential viscosity (DP) measurements. Chromatographic conditions: Column: $PL_{gel}$ mixed C (300×7.5 mm, 5 μm particles) covering the molecular weight range from about $1×10^3$ to about $2.5×10^6$ Da from Polymer Laboratories (Church Stretton, UK); Mobile phase: tetrahydrofuran containing 5 g/l of sodium trifluoroacetate; Mobile phase flow: either 0.5 or 0.7 ml/min; Solute concentration: about 1-2 mg/ml; Injection volume: 100 μl; Detection: RI, LALS, RALS, DP. Procedure of molecular weight calibration: Relative calibration is done by use of a set of 10 polystyrene calibration standards obtained from Polymer Laboratories (Church Stretton, UK) spanning the molecular weight range from 1,930,000 Da-5,050 Da, i.e., PS 1,930,000, PS 1,460,000, PS 1,075,000, PS 560,000, PS 330,000, PS 96,000, PS 52,000, PS 30,300, PS 10,100, PS 5,050 Da. Absolute calibration is done on the base of the responses of LALS, RALS and DP. As experienced in a large number of investigations this combination provides optimum calculation of molecular weight data. Usually PS 96,000 is used as the molecular weight calibration standard, but in general every other PS standard lying in the molecular weight range to be determined can be chosen for this purpose.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

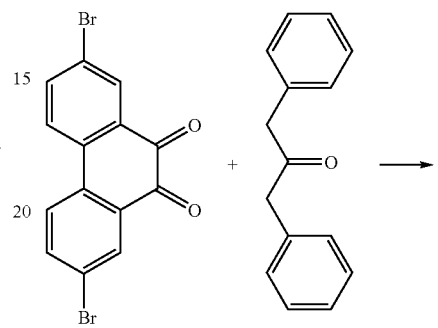

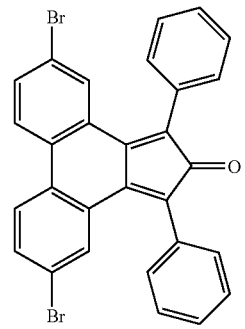

a) A solution of 1.40 g potassium hydroxide in 5.6 ml methanol is added to 9.15 g (25 mmol) of 2,7-dibromo-phenanthrene-9,10-dione and 5.78 g (27.5 mmol) of 1,3-diphenyl-propan-2-one in 300 ml methanol. The reaction mixture is refluxed for 30 min and cooled to 25° C. The product is filtered off, washed with methanol and dried (yield: 11.5 g (85%)).

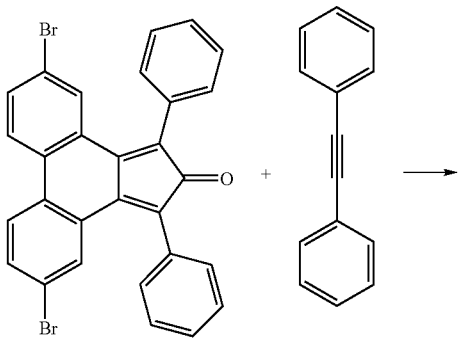

-continued
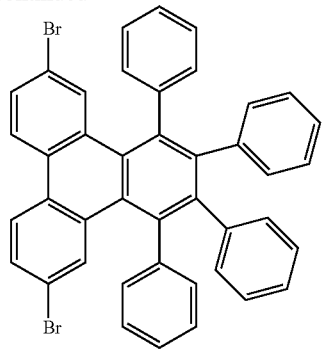
b) 1 ml biphenylether is added to 540 mg (1 mmol) of the product of example 1a and 200 mg (1.10 mmol) diphenylacetylene. The reaction mixture is heated under argon for 5 h at 250° C. The biphenyl ether is distilled off. The product is purified by chromatography on silica gel with toluene/cyclohexane (1/5) (yield: 310 mg (45%); melting point: 289-292° C.).
Example 2
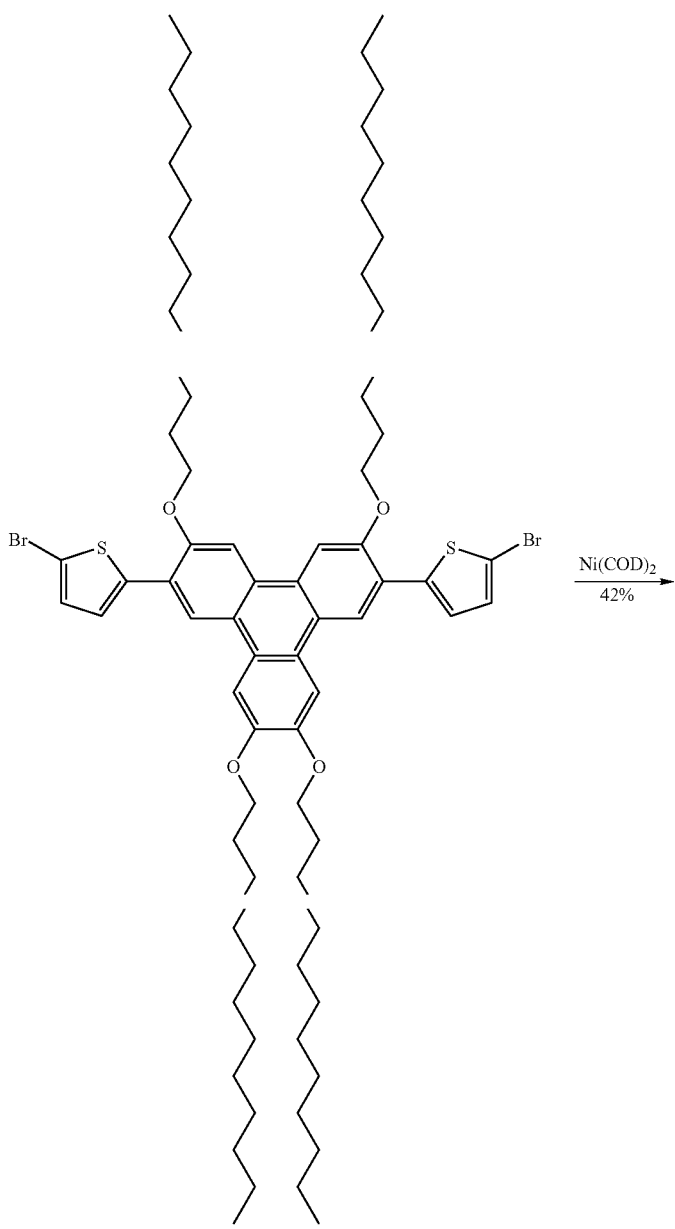

-continued

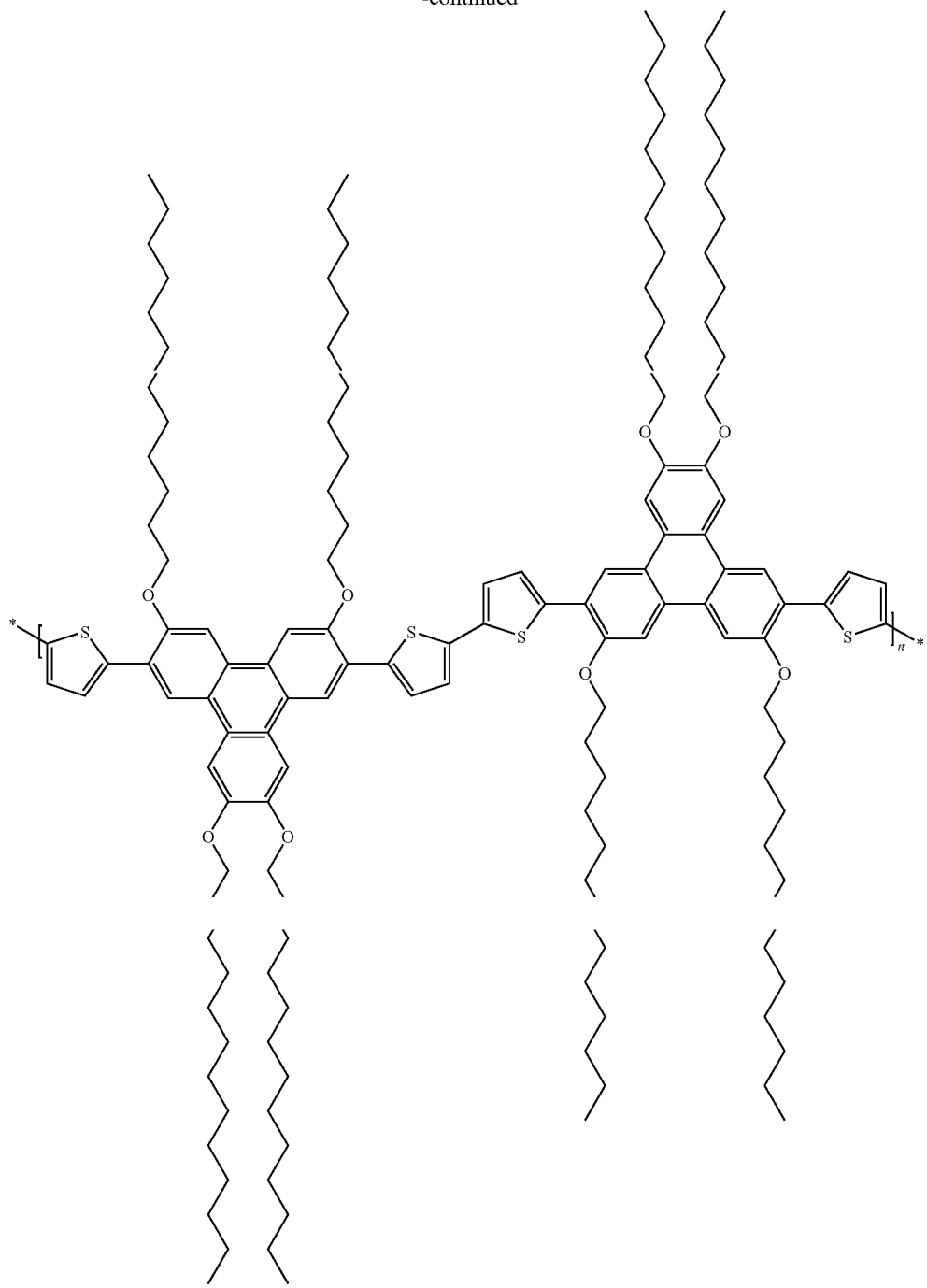

In a Schlenk tube, a solution of 83 mg of Ni(COD)$_2$ and 48 mg bipyridine in 5 ml of toluene is degassed for 15 min. 310 mg of the corresponding dibrominated monomer is added to this solution and then the mixture is heated to 80° C. and stirred vigorously overnight. The solution is poured on 100 ml of a 1/1/1 methanol/HCl/acetone mixture and stirred for 1 h. The precipitate is then filtrated, dissolved in CHCl$_3$ and stirred vigorously at 60° C. with an aqueous solution of ethylenediaminetetraacetic acid (EDTA) tetrasodium salt for one additional hour. The organic phase is washed with water, concentrated and precipitated in methanol. The residue is purified by soxhlet extraction using methanol and hexane and the polymer is then extracted with CHCl$_3$ to give 115 mg of red powder.

$M_w$=21000

Solubility ~1% by weight in chloroform

Photophysical Properties:

UV of chloroform solution at 2 different temperatures and spin coated film on glass substrate made from a chloroform solution:

| Annealing Conditions | UV/Vis-absorption |
|---|---|
| Solution at 50° C. | 460 nm |
| Solution at RT | 480 nm, 505 nm |
| film | 485 nm, 515 nm |

The bathochromic shift of the band at 460 nm shows the appearance of strong aggregation behaviour.

Application Example 1

Field-Effect Transistors a) Experimental:

Bottom-gate thin-film transistor (TFT) structures with p-Si gate were used for all experiments. A high-quality thermal $SiO_2$ layer served as gate-insulator of $C_i$=32.6 nF/cm$^2$ capacitance per unit area. Source and drain electrodes were patterned by photolithography directly on the gate-oxide (bottom-contact configuration). On each substrate 16 transistors are present with Au source/drain electrodes defining channels of different length. Prior to the deposition of the organic semiconductor the $SiO_2$ surface was derivatized with hexamethyldisilazane (HMDS) or octadecyltrichlorosilane (OTS). The films are prepared either by spin casting or drop casting the polymer obtained in example 1 in different solvents. The transistor behaviour is measured on an automated tester elaborated by CSEM, Transistor Prober TP-10.

b) Transistor Performance:

The thin-film transistors showed clear p-type transistor behavior. From a linear fit to the square root of the saturated transfer characteristics a field-effect mobility of $10^{-4}$ cm$^2$/Vs could be determined. The transistors showed a threshold voltage of about 0 V to 4 V. The transistors showed decent on/off current ratios of $10^4$.

Example 3

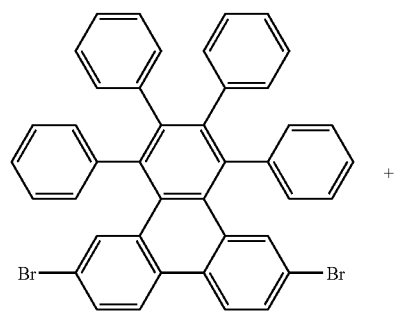

+

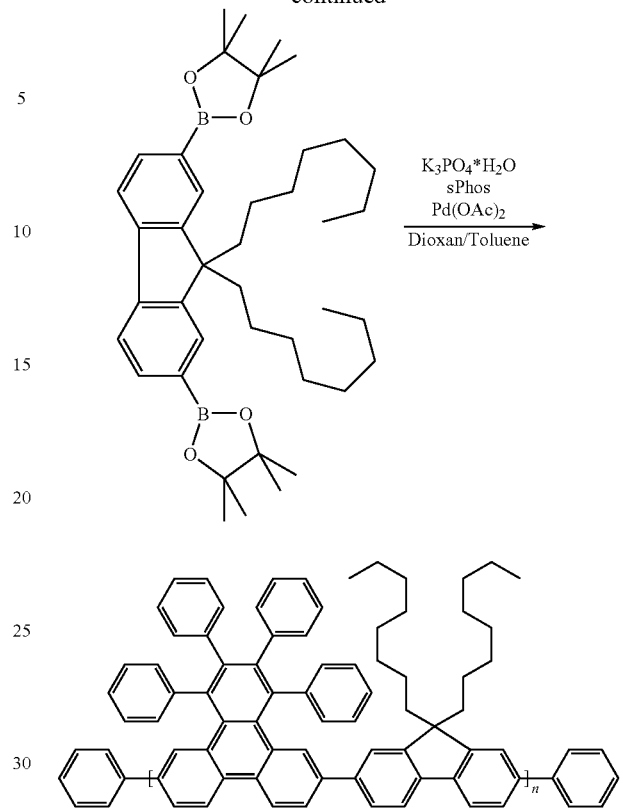

A solution of 752.2 mg (1.089 mmol) of the product of example 1b and 700.0 mg (1.089 mmol) 2,7-bis(4,4,5,5,-tetramethyl-1,3,2-dioxaborolan-2-yl)-9,9-dioctylfluorene in 5 ml 1,4-dioxane and 5 ml toluene is degassed. 2.4 mg (0.011 mmol) palladium acetate and 27 mg (0.065 mmol) 2-dicyclohexylphosphino-2',6'-di-methoxybiphenyl are added. The reaction mixture is degassed. A degassed solution of 1.32 g (5.45 mmol) potassium phosphate tribasic monohydrate in 3 ml water is added. The reaction mixture is refluxed after the addition of 5 and 10 ml toluene for 3 h and 3.5 h, respectively. The 30 ml degassed toluene and 260 mg (1.63 mmol) degassed bromobenzene are added. The reaction mixture is refluxed for 15 h. 20 ml degassed toluene and 560 mg (2.50 mmol) 4,4,5,5-tetramethyl-2-phenyl-1,3,2-dioxaborolane in 3 ml degassed toluene are added. The reaction mixture is stirred for 3 h. 30 ml toluene are added and the reaction mixture is washed with 100 ml 1% sodium cyanide solution. The toluene is partly distilled off and the remaining solution is poured into methanol. The polymer is filtered off and is washed with methanol, water acetone and methanol. The polymer is dissolved in toluene and is stirred at 90° C. with a 100 ml 1% sodium cyanide solution for 2 h. The organic phase is separated off and the toluene is partly distilled off. The remaining solution is poured into methanol and the polymer is filtered off. The polymer is washed with methanol (yield: 0.89 g (89%)).

GPC (polystyrene standard): $M_w$=130 00, PD=5.4.

Example 4

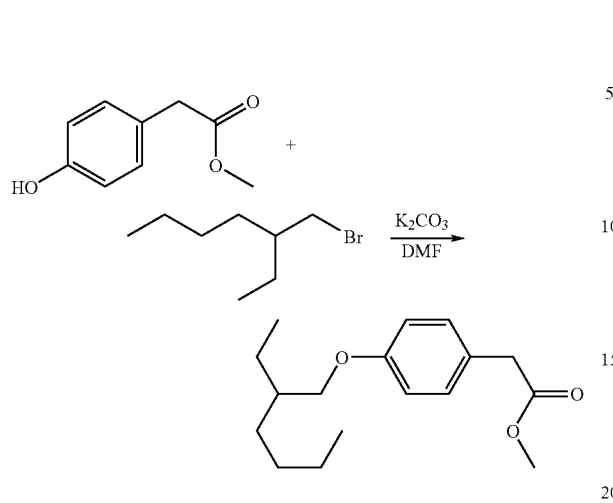

a) To 10.0 g (60.2 mmol) (4-hydroxy-phenyl)-acetic acid methyl ester and 12.8 g (66.2 mmol) 3-bromomethyl-heptane in 100 ml DMF 25.0 g (181 mmol) potassium carbonate is added under nitrogen. The reaction mixture is heated to 120° C. for 2 h. Additional 5.81 g (3.01 mmol) 3-bromomethyl-heptane and 12.5 g (9.03 mmol) potassium carbonate are added. The reaction mixture is heated to 120° C. for additional 5 h. The solids are filtered off, washed with diethyl ether, the organic phase is washed with water and dried with magnesium sulfate. The solvent is removed in vacuum (yield: 14.1 g (84%)).

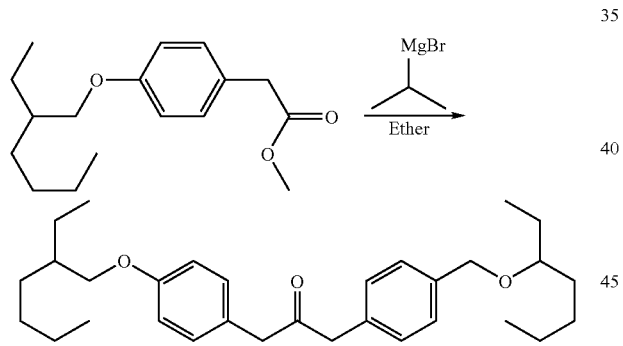

b) To 1.20 g (5.01 mmol) magnesium in 10 ml water free diethyl ether 6.68 g (5.43 mmol) 2-brom-propane in 10 ml diethyl ether are slowly added under nitrogen. After the 2-brom-propane has been added, the reaction mixture is refluxed for 30 min. To this reaction mixture 12.0 g (4.18 mmol) of the product of example 4a are added at 0° C. The reaction mixture is stirred for 3 h at 25° C., ice is added to the reaction mixture, the reaction mixture is acidified with sulfuric acid (96%) and stirred for 30 min. The reaction mixture is extracted with diethyl ether. The solvent is distilled off. 100 ml glacial acetic acid and 20 ml 20% hydrochloric acid are added. The reaction mixture is refluxed for 2.5 h. The formed oil is separated, diluted with diethyl ether and washed with water. The organic phase is dried with magnesium sulfate. The solvent is distilled off (yield: 8.86 g (91%)).

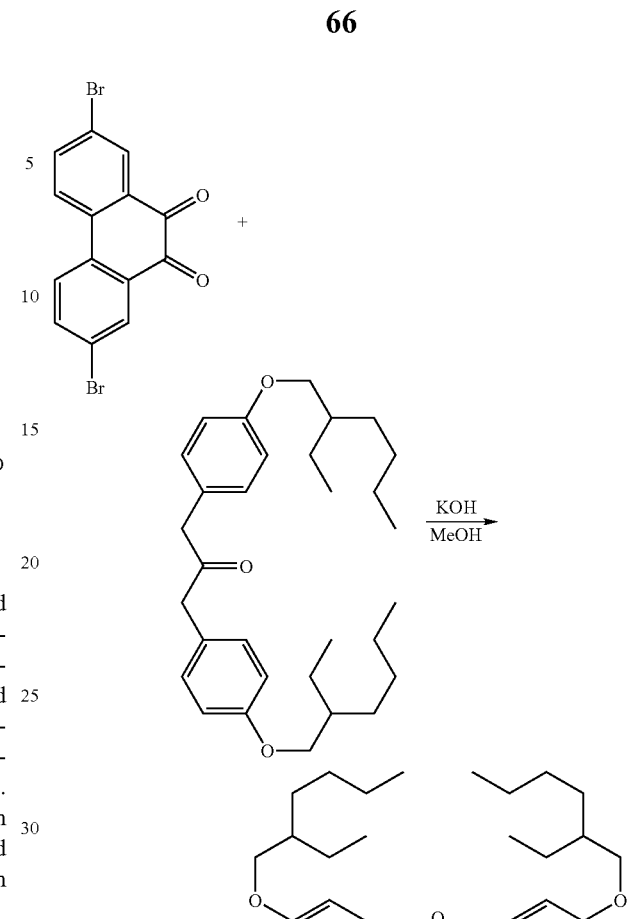

c) To 8.42 g (18.0 mmol) of the product of example 4b and 5.50 g (15.0 mmol) 2,7-dibromo-phenanthrene-9,10-dione in 200 ml methanol 840 mg (15.0 mmol) potassium hydroxide in 5 ml methanol are added under argon. The reaction mixture is refluxed for 3 h. The reaction mixture is cooled to 25° C. and the product is filtered off (yield: 8.26 g (70%)).

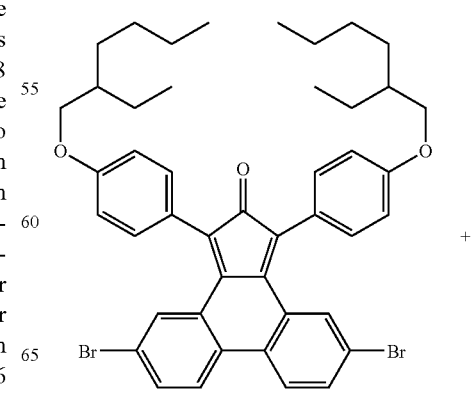

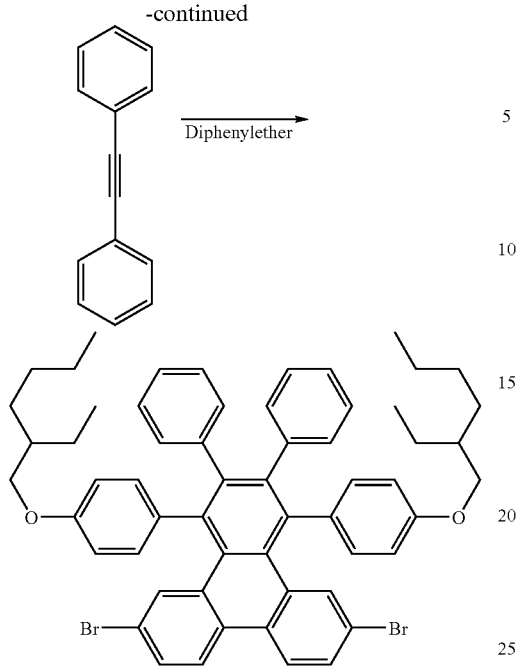

d) To 8.00 g (10.0 mmol) of the product of example 4c in 16 ml diphenyl ether 1.97 g (11.1 mmol) diphenyl-acetylene are added under argon. The reaction mixture is heated to 250° C. (outside temperature) for 2.5 h. The diphenyl ether is distilled off. The crude product is dissolved in cyclohexane and filtered on silica gel. The solvent is distilled off. A column chromatography on silica gel with cyclohexane/ethyl acetate (40/1) leads to the desired product (yield: 2.61 g (27%)).

e) Example 3 is repeated, except that instead of the product of example 3 the product of example 4d is used (GPC (polystyrene standard): $M_w$=39 000, PD=13.8).

Example 5

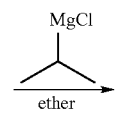

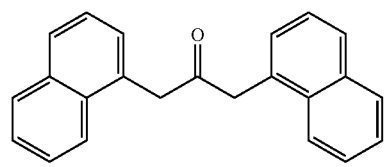

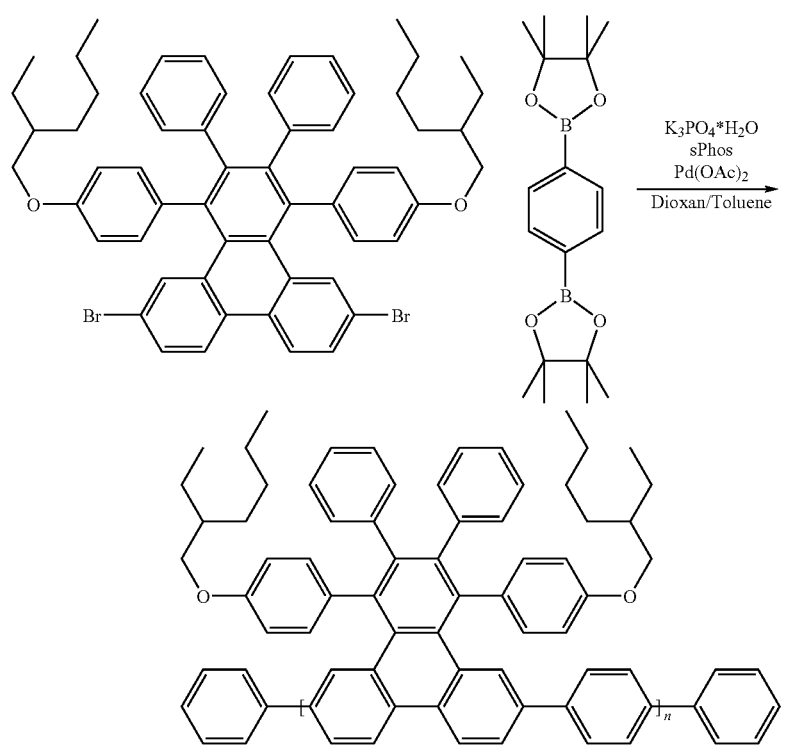

a) The product is prepared according to example 4b.

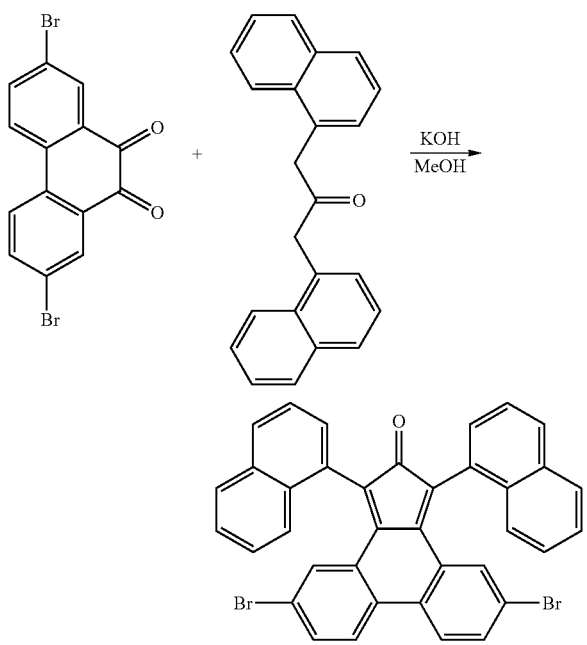

b) The product is prepared according to example 4c.

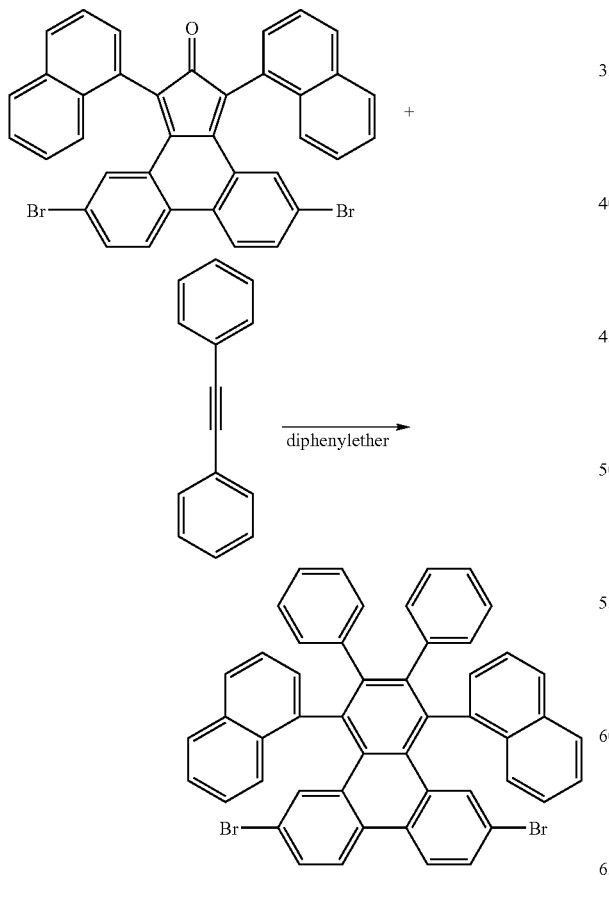

c) The product is prepared according to example 4d (melting point: 302-308° C.).

Application Example 2

An organic luminescence device having a single organic layer is prepared in the following manner: On a glass substrate, a 100 nm thick ITO film is formed by sputtering and subsequently patterned. Onto oxygen-plasma treated ITO film a 80 nm thick hole-injection layer using PEDOT:PSS (Baytron P, Al4083, HC Starck) is formed by spin-coating followed by heating at 200° C. (5 minutes). A solution of 66 mg of the polymer of example 3 and 33 mg of 2-(4-biphenylyl)-5-(4-tert-butylphenyl)-1,3,4-oxadiazole (PBD) in 10 g of toluene are applied by spin coating (2500 rpm; 10 sec) to obtain a thickness of 80 nm. Afterwards the substrate is set in a vacuum deposition chamber, a cathode having a two-layer electrode structure is formed by depositing 50 nm barium followed by 100 nm aluminium. When the device is driven at a current density of 10 mA/cm² the resulting current efficiency was 1.07 cd/A at CIE of 0.21, 0.20.

Application Example 3

The device is prepared and evaluated in the same manner as described in application example 2, except for using the polymer of example 4e in a blend of 2/3 the emitter polymer and 1/3 of a well known hole transporting molecule N,N'-diphenyl-N,N'-(bis(3-methylphenyl)-[1,1-bi-phenyl]-4,4'-diamine (TPD). The current efficiency was 0.18 cd/A at 6V with the color coordinates x=0.33, y=0.44.

Example 6

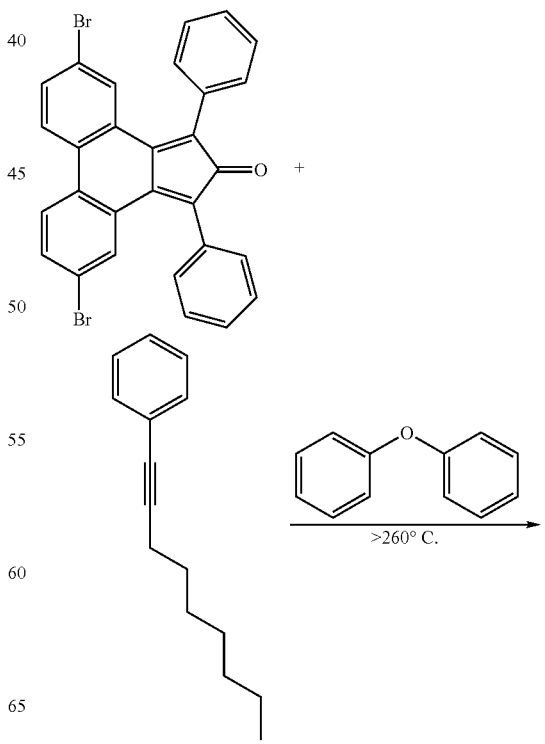

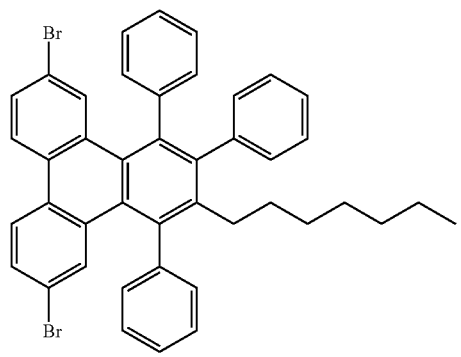

The Diels-Alder reaction between product of example 1a (378 mg, 0.7 mmol) and 1 equivalent of 1-phenyl-1-nonyne (140 mg, 0.7 mmol) using diphenylether as a solvent at >259° C. affords the desired monomer 6,11-dibromo-2-heptyl-1,3,4-triphenyl-triphenylene. The biphenyl is destilled off and the product is separated on silica gel column with hexane yielding 250 mg (50% yield).

Example 7

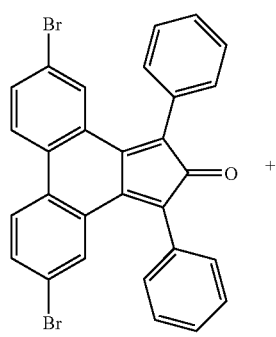 +

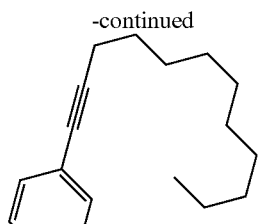

1-(dodec-1-ynyl)-4-octylbenzene is obtained via Sonogashira coupling reaction between 1-dodecyne and 0.8 equivalent of 1-bromo-4-octyl-benzene in the presence of the catalyst Pd(PPh$_3$)$_4$/CuI and the base piperidine at 50° C. gave 1-(dodec-1-ynyl)-4-octylbenzene in 70% yield. Subsequent Diels-Alder reaction between 990 mg (1.85 mmol) of product of example 1a and 656 mg (1.85 mmol) of 1-(dodec-1-ynyl)-4-octylbenzene using diphenylether as solvent at >259° C. affords 880 mg (55% yield) of the product after column chromatography from hexane.

Example 8

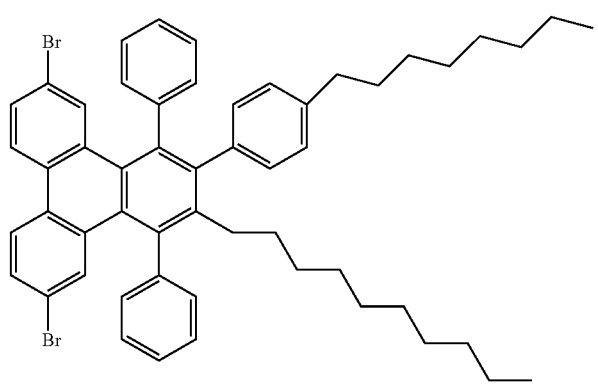

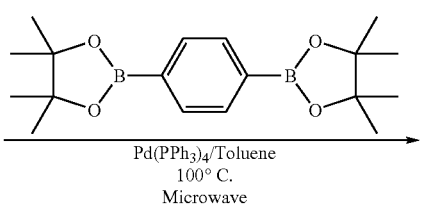

Pd(PPh$_3$)$_4$/Toluene
100° C.
Microwave

-continued

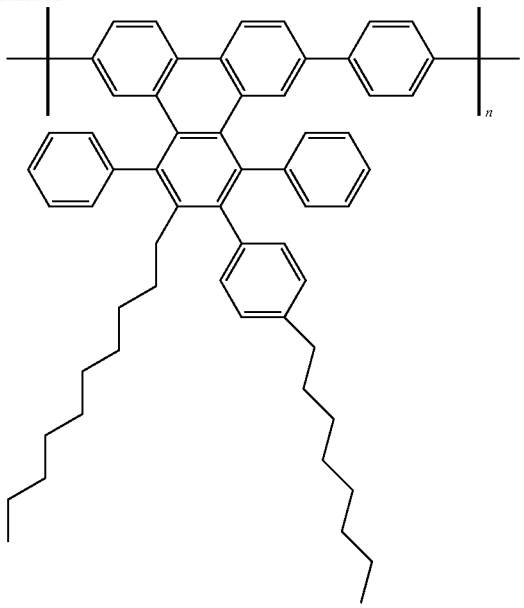

The microwave assisted Suzuki reaction is performed using 229.9 mg (0.265 mmol) monomer from example 7 with 1 equivalent of bis(pinacolato)diboron (0.265 mmol, 87.56 mg) and the catalyst $Pd(PPh_3)_4$ (0.013266 mmol, 15.329 mg) together with 2 ml of $K_2CO_3$ (2M/$H_2O$ solution) in toluene at 100° C. for 1 h (50W & 7 bar) to afford the polymer. GPC analysis for the polymer product after washing with 250 ml methanol/10 ml HCl (37%) and soxhlet extraction in ethylacetate (50% yield) shows $M_n=25*10^3$ g/mol, $M_w=35*10^3$ g/mol, P50% yield D=1.4 (THF, PPP standard).

The invention claimed is:

1. A polymer comprising repeating unit(s) of the following formula

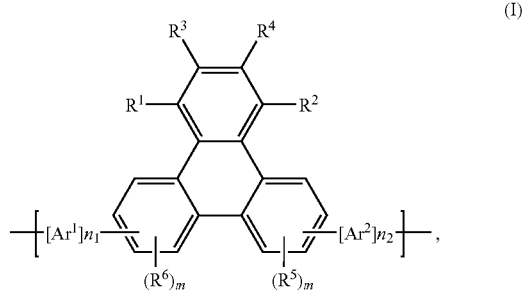

(I)

wherein $R^1$, $R^2$, $R^3$, $R^4$, $R^5$ and $R^6$ are independently of each other hydrogen, F, $SiR^{100}R^{101}R^{102}$, or an organic substituent, or $R^1$ and $R^3$, $R^4$ and $R^2$, $R^3$ and $R^4$, and/or any of the substituents $R^5$ and/or $R^6$, which are adjacent to each other, together form an aromatic, or heteroaromatic ring, or ring system, which can optionally be substituted, with the proviso that at least two of the substituents $R^1$, $R^2$, $R^3$ and $R^4$ are an optionally substituted $C_6$-$C_{24}$aryl or $C_2$-$C_{20}$heteroaryl group, m is 0, or an integer of 1 to 3, n1 and n2 are 0, or an integer 1, or 2, $R^{100}$, $R^{101}$ and $R^{102}$ are independently of each other $C_1$-$C_{18}$alkyl, substituted or unsubstituted $C_6$-$C_{18}$aryl, and $Ar^1$ and $Ar^2$ are each independently of each other a substituted or unsubstituted arylen, or heteroarylen group.

2. The polymer according to claim 1 comprising repeating units of formula I, wherein $R^1$ and $R^2$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G;

$R^3$ and $R^4$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G; wherein at least one of $R^1$, $R^2$, $R^3$ and $R^4$ are different from H, each group $R^5$ and $R^6$ is independently of each other in each occurrence H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, m is 0, or an integer 1 to 3, D is —CO—; —COO—; —S—; —SO—; —$SO_2$—; —O—; —$NR^{25}$—; —$SiR^{30}R^{31}$—; —$POR^{32}$—; —$CR^{23}$=$CR^{24}$—; or —C≡C—; and E is —$OR^{29}$; —$SR^{29}$; —$NR^{25}R^{26}$; —$COR^{28}$; —$COOR^{27}$; —$CONR^{25}R^{26}$; —CN; or halogen, G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{27}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl.

3. The polymer according to claim 2, wherein the polymer contains repeating units of formula

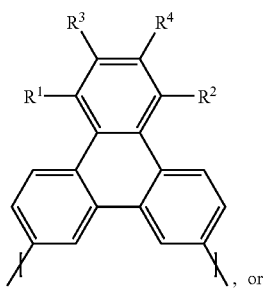
(IIIa)

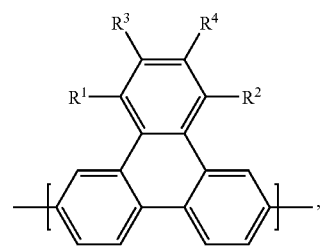
(IIa)

wherein
$R^1$, $R^2$ and $R^3$ are independently of each other $C_6$-$C_{12}$aryl, or $C_2$-$C_{11}$heteroaryl, which may optionally be substituted by one or more groups G, and $R^4$ has the meaning of $R^3$, or is $C_1$-$C_{18}$alkyl.

4. The polymer according to claim 3, wherein the polymer contains repeating units of formula (IIa), wherein $R^1$, $R^2$ and $R^3$ are independently of each other

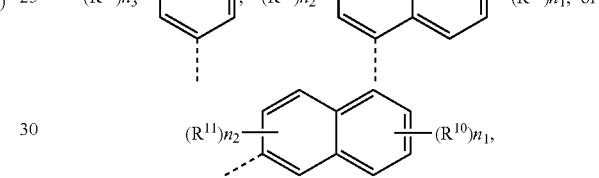

wherein $n_1$ is 0, or an integer 1, 2, 3, or 4, $n_2$ is 0, or an integer 1, 2, or 3, $n_3$ is 0, or an integer 1, 2, 3, 4, or 5, $R^{10}$ and $R^{11}$ are independently of each other $C_1$-$C_{25}$alkyl, or $C_1$-$C_{25}$alkoxy.

5. The polymer according to claim 1 comprising repeating unit(s) of formula

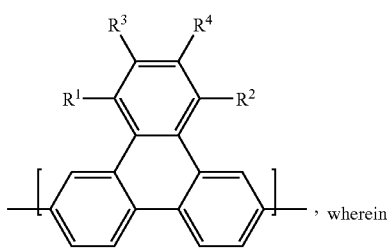
(IIa)
, wherein

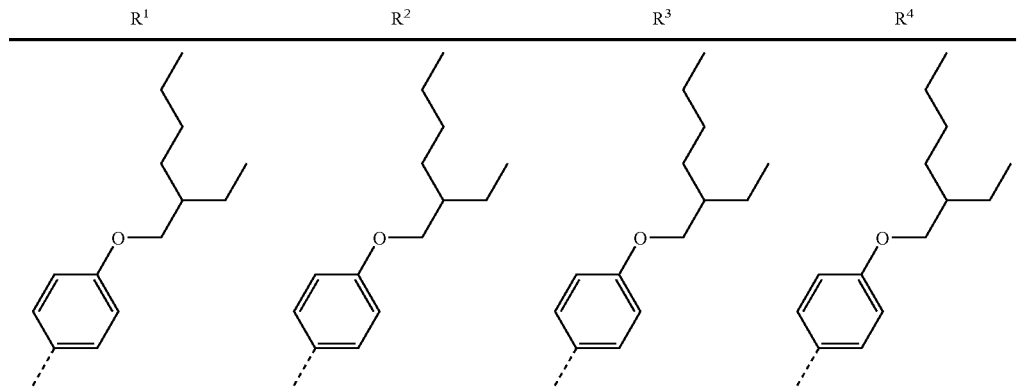

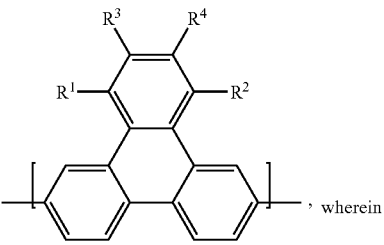

-continued
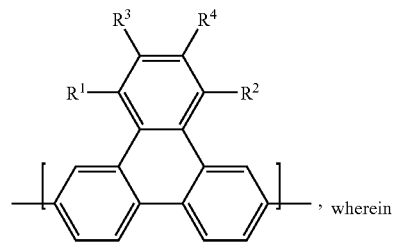, wherein
| R¹ | R² | R³ | R⁴ |
|---|---|---|---|
| 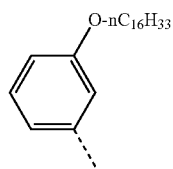 | 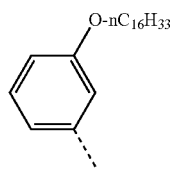 | 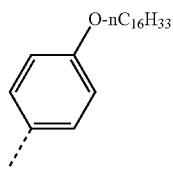 | 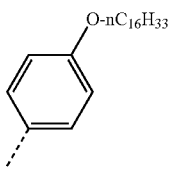 |
| 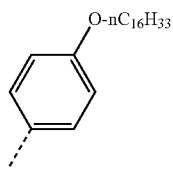 | 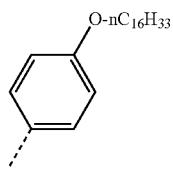 | 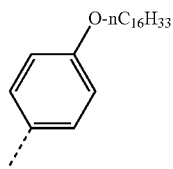 | 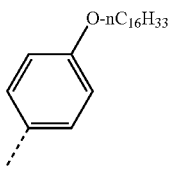 |
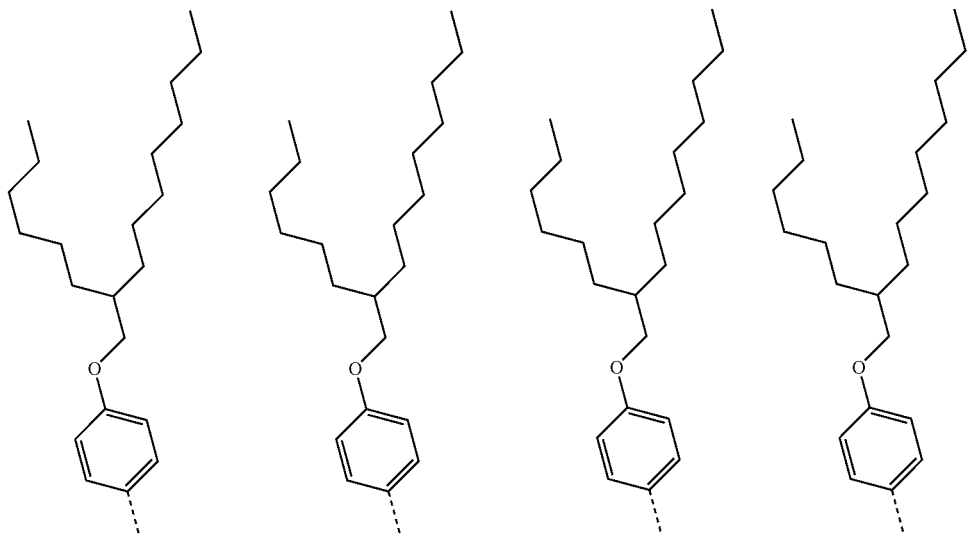

-continued
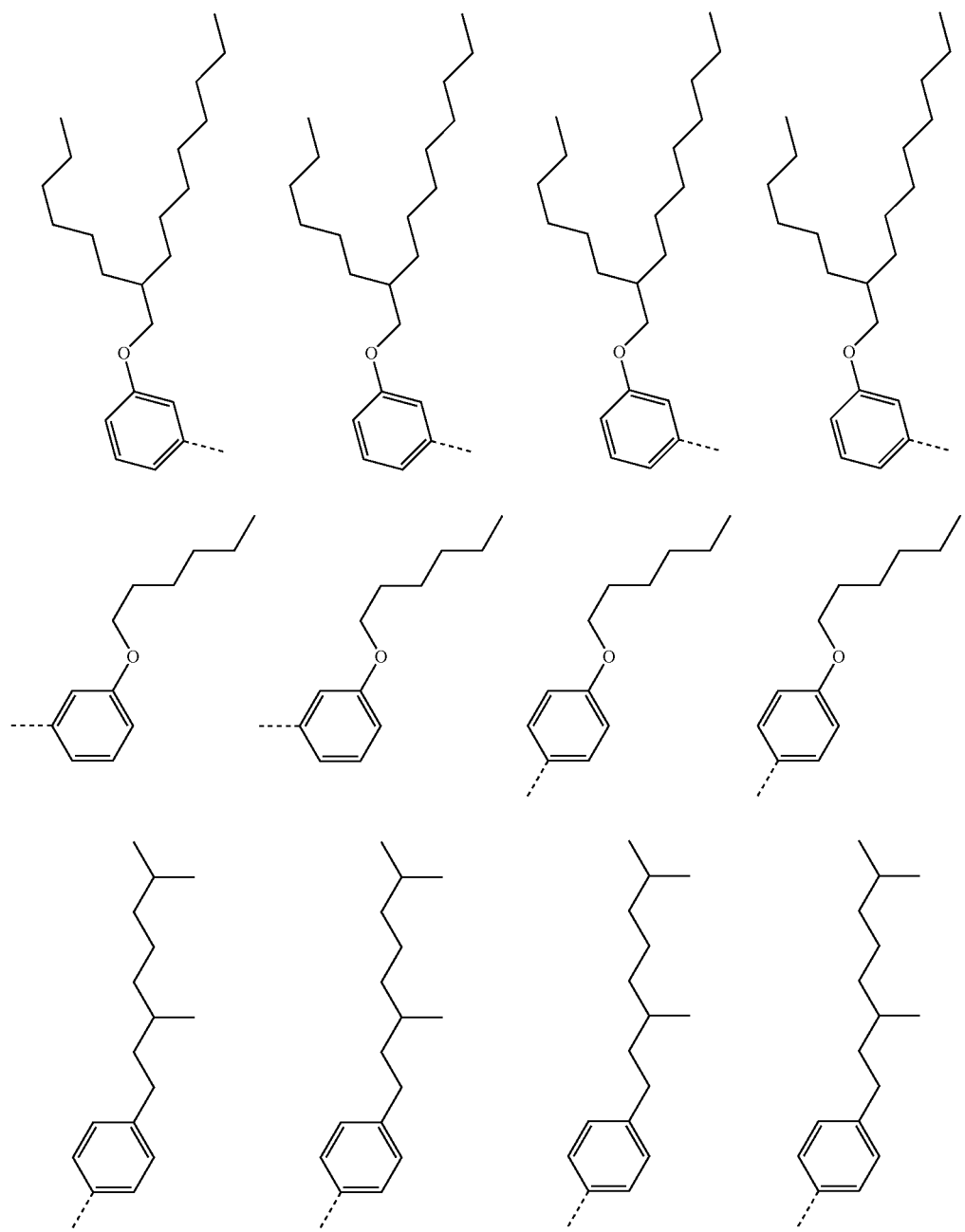

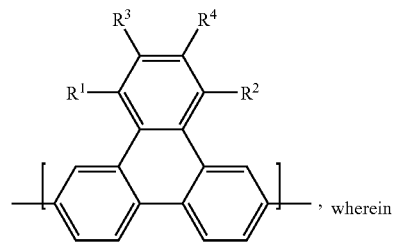

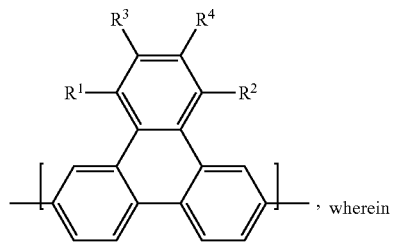

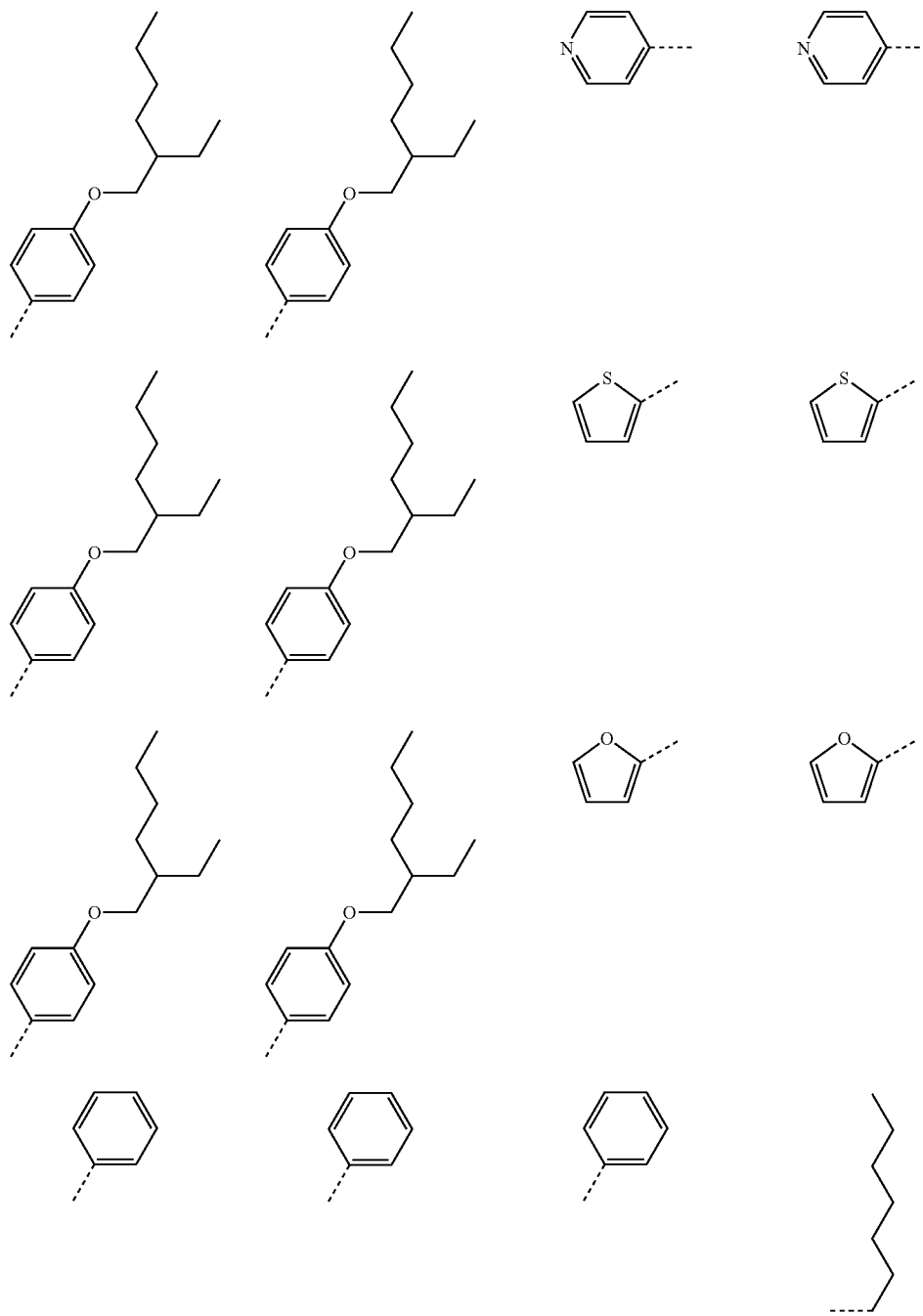

-continued
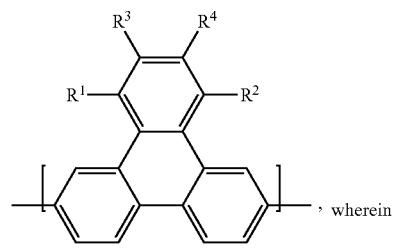
, wherein
| R¹ | R² | R³ | R⁴ |
|---|---|---|---|
| 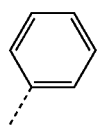 | 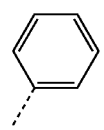 |  | 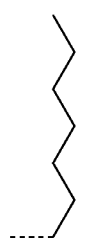 |
| 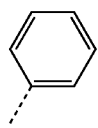 | 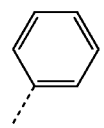 |  | 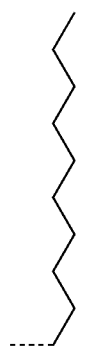 |
| 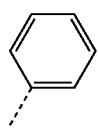 | 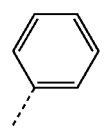 | 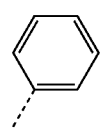 | 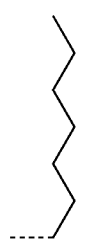 |

-continued

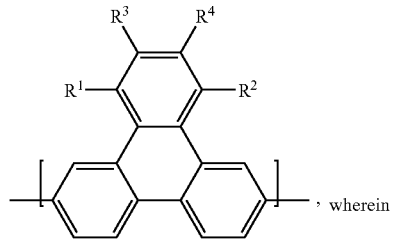

| R¹ | R² | R³ | R⁴ |
|---|---|---|---|
| 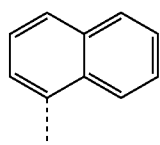 | 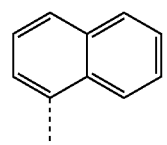 |  | 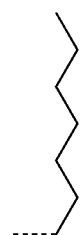 |
| 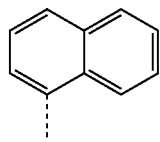 | 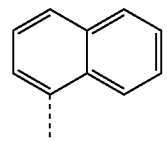 |  |  |

6. An electronic device or a component therefore, comprising the polymer according to claim 1.

7. An electronic device or a component according to claim 6 which is a polymer light emitting diode, organic integrated circuit, organic field effect transistor, organic thin film transistor, organic solar cell, thermoelectric device, electrochromic device, or organic laser diode.

8. Polymer light emitting diodes, comprising one or more of the polymers according to claim 1 as electroluminescent material.

9. A compound of the formula

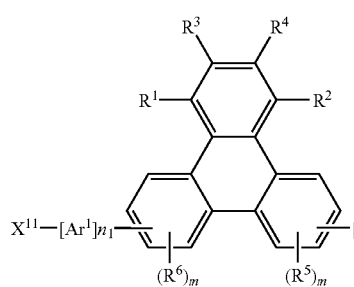

wherein $R^1$, $R^2$, $R^3$, $R^4$, $R^5$ and $R^6$ are independently of each other hydrogen, F, $SiR^{100}R^{101}R^{102}$, or an organic substituent, or $R^1$ and $R^3$, $R^4$ and $R^2$, $R^3$ and $R^4$, and/or any of the substituents $R^5$ and/or $R^6$, which are adjacent to each other, together form an aromatic, or heteroaromatic ring, or ring system, which can optionally be substituted, with the proviso that at least two of the substituents $R^1$, $R^2$, $R^3$ and $R^4$ are an optionally substituted $C_6$-$C_{24}$aryl or $C_2$-$C_{20}$heteroaryl group, m is 0, or an integer of 1 to 3, n1 and n2 are 0, or an integer 1, or 2, $R^{100}$, $R^{101}$ and $R^{102}$ are independently of each other $C_1$-$C_{18}$alkyl, substituted or unsubstituted $C_6$-$C_{18}$aryl, and $Ar^1$ and $Ar^2$ are each independently of each other a substituted or unsubstituted arylen, or heteroarylen group, $X^{11}$ is independently in each occurrence a halogen atom, —$ZnX^{12}$, —$SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, or —$OS(O)_2CF_3$, —$OS(O)_2$-aryl, —$OS(O)_2CH_3$, —$B(OH)_2$, —$B(OY^{11})_2$,

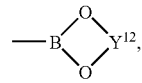

—$BF_4Na$, or —$BF_4K$, wherein $Y^{11}$ is independently in each occurrence a $C_1$-$C_{10}$alkyl group and $Y^{12}$ is independently in each occurrence —$CY^{13}Y^{14}$—$CY^{15}Y^{16}$—, or —$CY^{17}Y^{18}$—$CY^{19}Y^{20}$—$CY^{21}Y^{22}$—, wherein $Y^{13}$, $Y^{14}$, $Y^{15}$, $Y^{16}$, $Y^{17}$, $Y^{18}$, $Y^{19}$, $Y^{20}$, $Y^{21}$ and $Y^{22}$ are independently of each other hydrogen, or a $C_1$-$C_{10}$alkyl group, with the proviso that the following compounds are excluded:

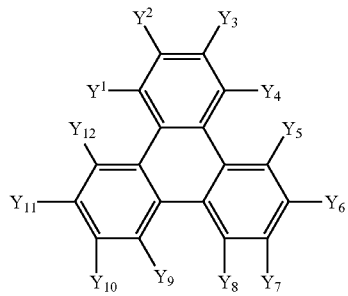

| $Y^2$ | $Y^3$ | $Y^5$ | $Y^6$ | $Y^7$ | $Y^8$ | $Y^9$ | $Y^{10}$ | $Y^{11}$ | $Y^{12}$ |
|---|---|---|---|---|---|---|---|---|---|
| $(CH_2)_5Me$ | $(CH_2)_5Me$ | H | H | Br | H | H | Br | H | H |
| OMe | OMe | OAc | H | Cl | OAc | OAc | Cl | H | OAc |
| 1) | 1) | H | 1) | Br | H | H | Br | 1) | H |
| 1) | 1) | H | Br | 1) | H | H | 1) | Br | H |
| 1) | 1) | H | H | Cl | H | H | Cl | H | H |
| H | H | H | H | Cl | H | H | Cl | H | H |
| 1) | 1) | H | H | Br | H | H | Br | H | H |
| H | H | H | Br | H | H | H | H | Br | H |
| OMe | OMe | OAc | H | Cl | OAc | OAc | H | Cl | OAc |
| H | H | H | Br | H | H | H | H | Br | H |

$^{1)}O(CH_2)_5Me$, or

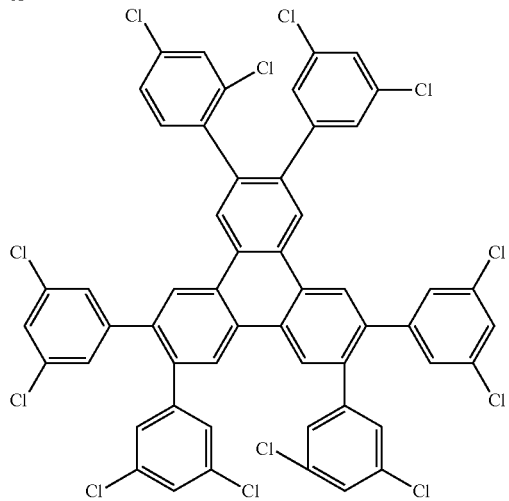

or

-continued

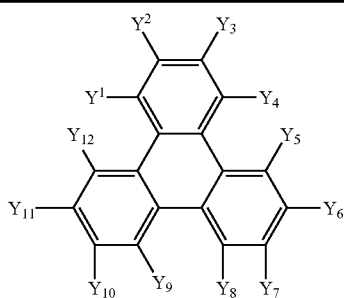

| $Y^2$ | $Y^3$ | $Y^5$ | $Y^6$ | $Y^7$ | $Y^8$ | $Y^9$ | $Y^{10}$ | $Y^{11}$ | $Y^{12}$ |
|---|---|---|---|---|---|---|---|---|---|

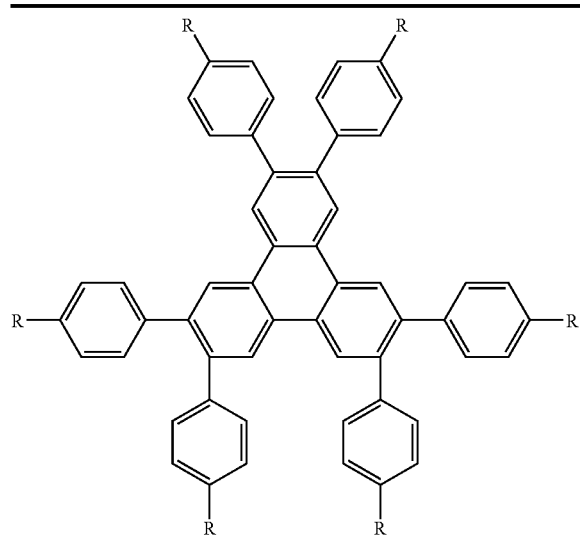

wherein R = Cl, Br, or F.

10. A compound of the formula

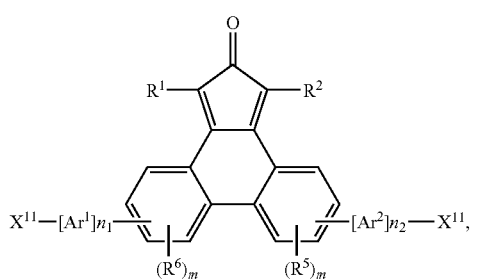

(XIV)

wherein $R^1$, $R^2$, $R^5$ and $R^6$ are independently of each other hydrogen, F, $SiR^{100}R^{101}R^{102}$, or an organic substituent, or any of the substituents $R^5$ and/or $R^6$, which are adjacent to each other, together form an aromatic, or heteroaromatic ring, or ring system, which can optionally be substituted, m is 0, or an integer of 1 to 3, n1 and n2 are 0, or an integer 1, or 2, $R^{100}$, $R^{101}$ and $R^{102}$ are independently of each other $C_1$-$C_{18}$alkyl, substituted or unsubstituted $C_6$-$C_{18}$aryl, and $Ar^1$ and $Ar^2$ are each independently of each other a substituted or unsubstituted arylen, or heteroarylen group, $X^{11}$ is independently in each occurrence a halogen atom, —$ZnX^{12}$, —$SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, or —$OS(O)_2CF_3$, —$OS(O)_2$-aryl, —$OS(O)_2CH_3$, —$B(OH)_2$, —$B(OY^{11})_2$,

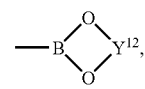

—$BF_4Na$, or —$BF_4K$, wherein $Y^{11}$ is independently in each occurrence a $C_1$-$C_{10}$alkyl group and $Y^{12}$ is independently in each occurrence —$CY^{13}Y^{14}$—$CY^{15}Y^{16}$—, or —$CY^{17}Y^{18}$—$CY^{19}Y^{20}$—$CY^{21}Y^{22}$—, wherein $Y^{13}$, $Y^{14}$, $Y^{15}$, $Y^{16}$, $Y^{17}$, $Y^{18}$, $Y^{19}$, $Y^{20}$, $Y^{21}$, and $Y^{22}$ are independently of each other hydrogen, or a $C_1$-$C_{10}$alkyl group, with the proviso that the following compound is excluded:

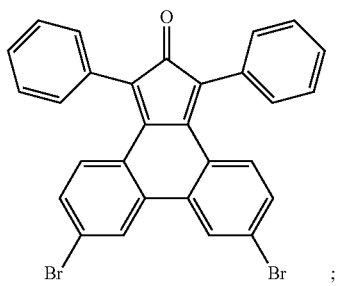

and with the further proviso that compounds of formula XIV are excluded, wherein $R^1$ and $R^2$ are a group of formula

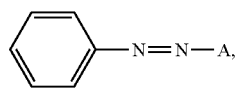

wherein A is a coupling residue having phenolic OH, $X^{11}$ is halogen, $n_1$, $n_2$ and m are 0.

11. A polymer according to claim 1 wherein $Ar^1$ and $Ar^2$ are each independently of each other a substituted or unsubstituted phenylene, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group.

12. A compound according to claim 9 wherein $Ar^1$ and $Ar^2$ are each independently of each other a substituted or unsubstituted phenylene, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group.

13. A compound according to claim 10 wherein $Ar^1$ and $Ar^2$ are each independently of each other a substituted or unsubstituted phenylene, a substituted or unsubstituted naphthalene group, a substituted or unsubstituted anthracene group, a substituted or unsubstituted diphenylanthracene group, a substituted or unsubstituted phenanthrene group, a substituted or unsubstituted acenaphthene group, a substituted or unsubstituted biphenylene group, a substituted or unsubstituted fluorene group, a substituted or unsubstituted carbazolyl group, a substituted or unsubstituted thiophene group, a substituted or unsubstituted triazole group or a substituted or unsubstituted thiadiazole group.

14. The polymer according to claim 1, wherein the polymer has a weight average molecular weight of 2000 Daltons or greater.

15. The polymer according to claim 2, wherein the polymer is a polymer of formula (VII)

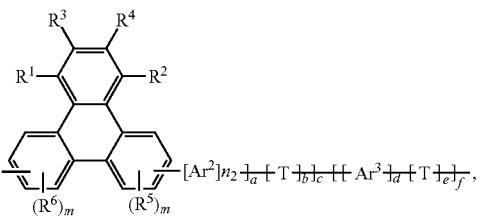

wherein
$Ar^1$, $n_1$, $Ar^2$, $n_2$, $R^1$, $R^2$, $R^3$, $R^4$, $R^5$, $R^6$ and m are as defined in claim 2,
a is 1,
b is 0, or 1,
c is 0.005 to 1,
d is 0, or 1,
e is 0, or 1, wherein e is not 1, if d is 0,
f is 0.995 to 0, wherein the sum of c and f is 1,
$Ar^3$ is selected from repeating units of formula:

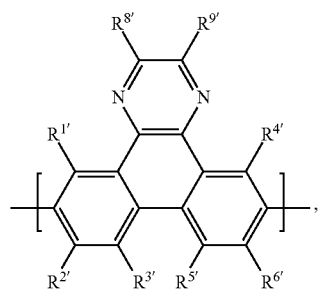

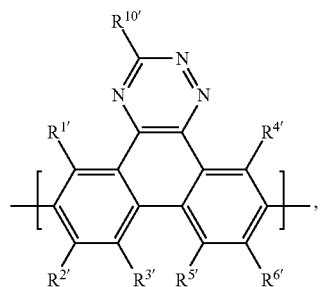

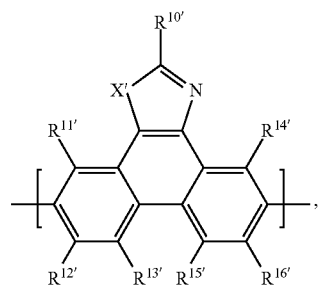

-continued

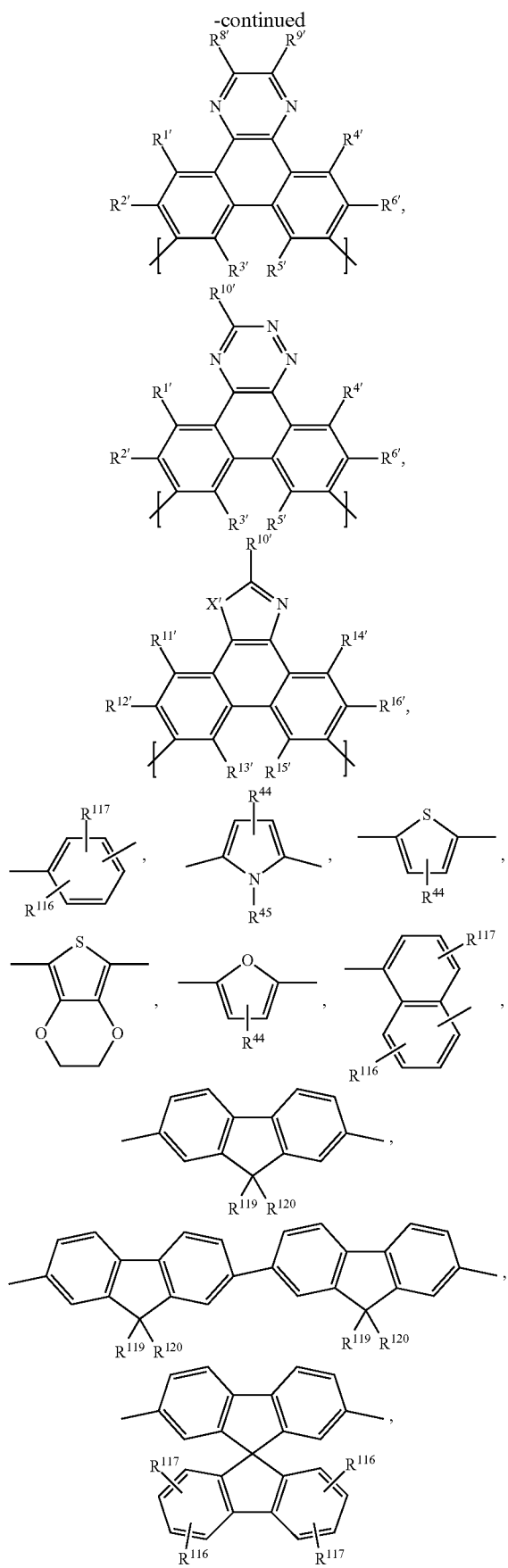

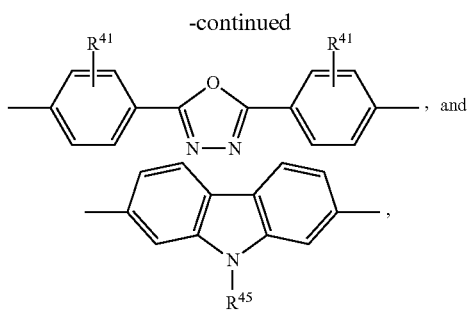

wherein $R^{1'}$ and $R^{4'}$ are hydrogen,
$R^{2'}$, $R^{3'}$, $R^{5'}$ and $R^{6'}$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, $C_7$-$C_{25}$aralkyl, or a group —$X^2$—$R^{18'}$,
$R^{8'}$ and $R^{9'}$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or a group —$X^2$—$R^{18'}$, or two substituents $R^{2'}$ and $R^{3'}$ and/or $R^{5'}$ and $R^{6'}$, which are adjacent to each other, together form a group

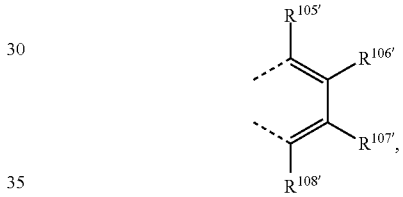

or two substituents $R^{5'}$ and $R^{3'}$, which are adjacent to each other, together form a group

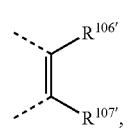

or
$R^8$ and $R^9$ together form a group

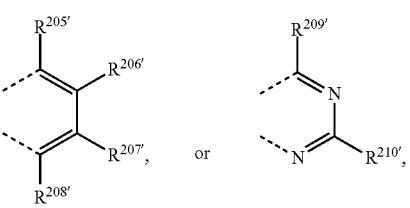

wherein $R^{205'}$, $R^{206'}$, $R^{207'}$, $R^{208'}$, $R^{209'}$ and $R^{210'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl,
$R^{10'}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$—$R^{18'}$, wherein $X^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18'}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25'}R^{26'}$;

$X'$ is O, S, or $NR^{17'}$, $R^{11'}$ and $R^{14'}$ are hydrogen, $R^{12'}$, $R^{13'}$, $R^{15'}$ and $R^{16'}$ are hydrogen, $R^{17'}$ is $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—; or two substituents $R^{11'}$ and $R^{12'}$, and/or $R^{14'}$ and $R^{16'}$, $R^{12'}$ and $R^{13'}$, and/or $R^{15'}$ and $R^{16'}$, which are adjacent to each other, together form a group

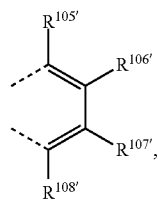

or two substituents $R^{15'}$ and $R^{13'}$,
which are adjacent to each other, together form a group

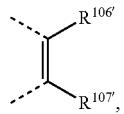

wherein $R^{105'}$, $R^{106'}$, $R^{107'}$ and $R^{108'}$ are independently of each other H, or $C_1$-$C_8$alkyl, $R^{44}$ and $R^{41}$ are hydrogen, $C_1$-$C_{18}$alkyl, or $C_1$-$C_{18}$alkoxy, and $R^{45}$ is H, $C_1$-$C_{18}$alkyl, or $C_1$-$C_{18}$alkyl which is substituted by E and/or interrupted by D, especially $C_1$-$C_{18}$alkyl which is interrupted by —O—, $R^{116}$ and $R^{117}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, $R^{119}$ and $R^{120}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =C$R^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, wherein G, D and E are as defined in claim 2, and T is selected from

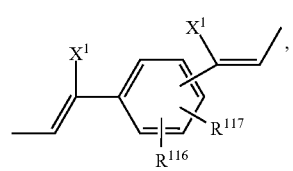 (VIa)

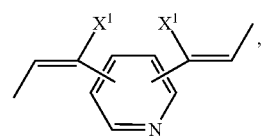 (VIb)

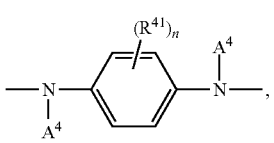 (VIc)

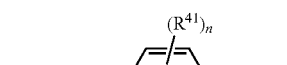 (VId)

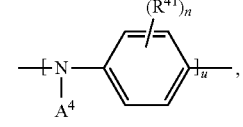 (VIe)

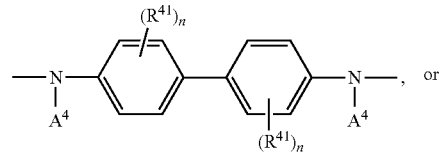

 (VIf)

wherein $X^1$ is a hydrogen atom, or a cyano group, $R^{116}$ and $R^{117}$ are as defined above, $R^{41}$ can be the same or different at each occurence and is Cl, F, CN, N($R^{45}$)$_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —NR$^{45}$—, —O—, —S—, —C(=O)—O—, or —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or two or more groups R$^{41}$ form a ring system;

R$^{45}$ is H, a C$_1$-C$_{25}$alkyl group, a C$_4$-C$_{18}$cycloalkyl group, in which one or more carbon atoms which are not in neighbourhood to each other could be replaced by —NR$^{45'}$—, —O—, —S—, —C(=O)—O—, or, —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced O, S, or N, and/or which can be substituted by one or more non-aromatic groups R$^{41}$, R$^{45'}$ is H, a C$_1$-C$_{25}$alkyl group, or a C$_4$-C$_{18}$cycloalkyl group, n can be the same or different at each occurrence and is 0, 1, 2, or 3, especially 0,1, or 2, very especially 0 or 1, and u is 1, 2, 3, or 4;

A$^4$ is a C$_6$-C$_{24}$aryl group, a C$_2$-C$_{30}$heteroaryl group, especially phenyl, naphthyl, anthryl, biphenylyl, 2-fluorenyl, phenanthryl, or perylenyl, which can be substituted by one or more non-aromatic groups R$^{41}$.

16. The polymer according to claim 15, wherein the polymer is copolymer of formula

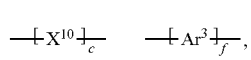
(VIIb)

wherein X$^{10}$ is a repeating unit of formula I, c, f and Ar$^3$ are as defined in claim 15.

17. The polymer according to claim 15, wherein the polymer is a homopolymer of formula

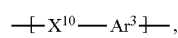
(VIIc)

wherein X$^{10}$ and Ar$^3$ are as defined in claim 15.

18. The polymer according to claim 15, wherein the polymer is a polymer of formula

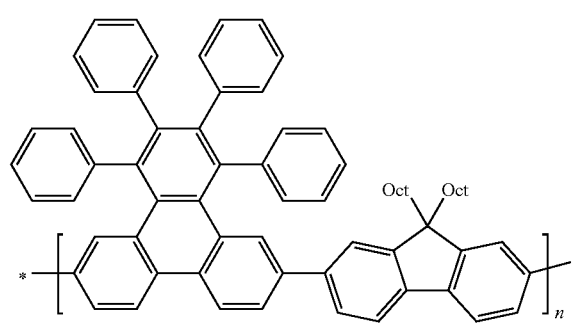

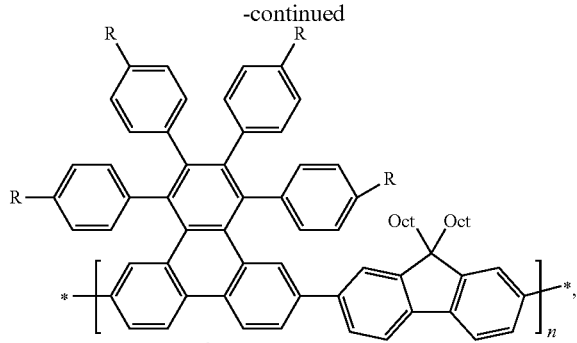

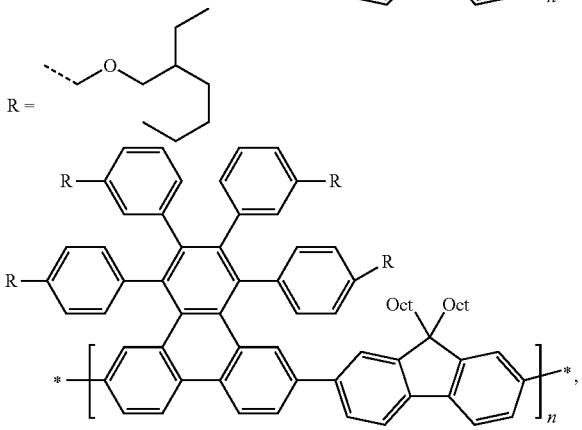

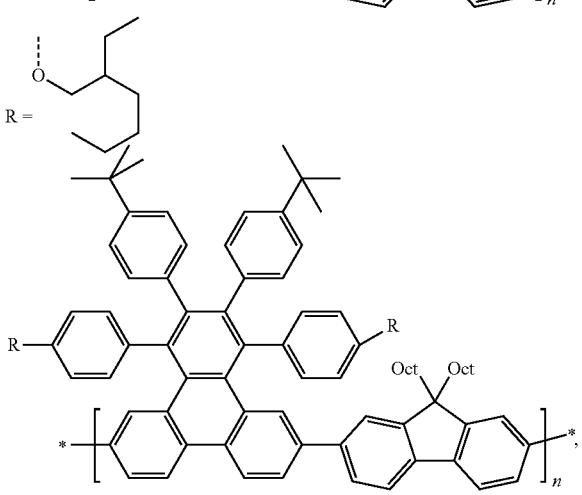

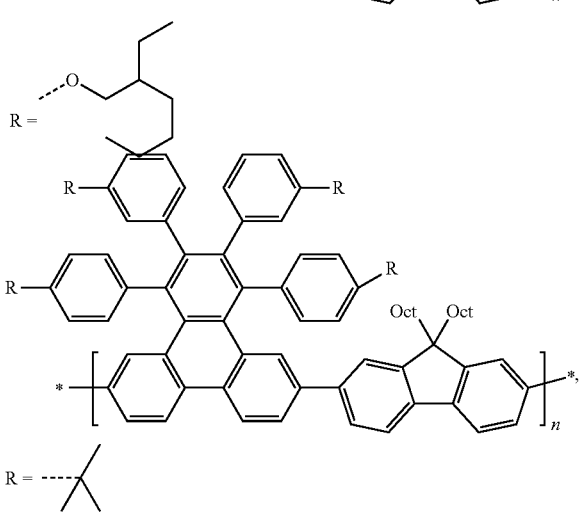

105
-continued
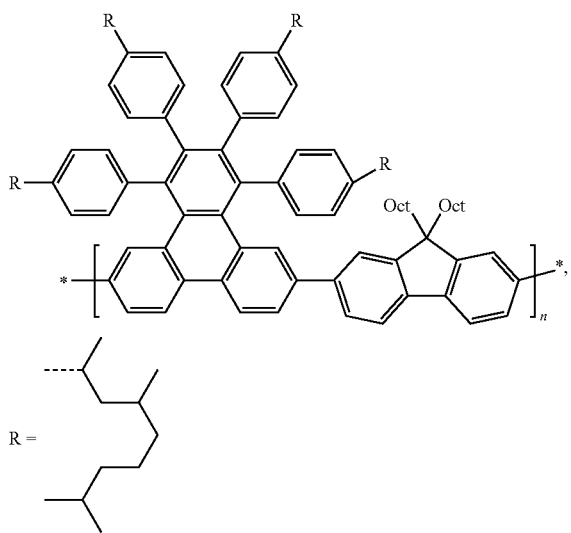
106
-continued
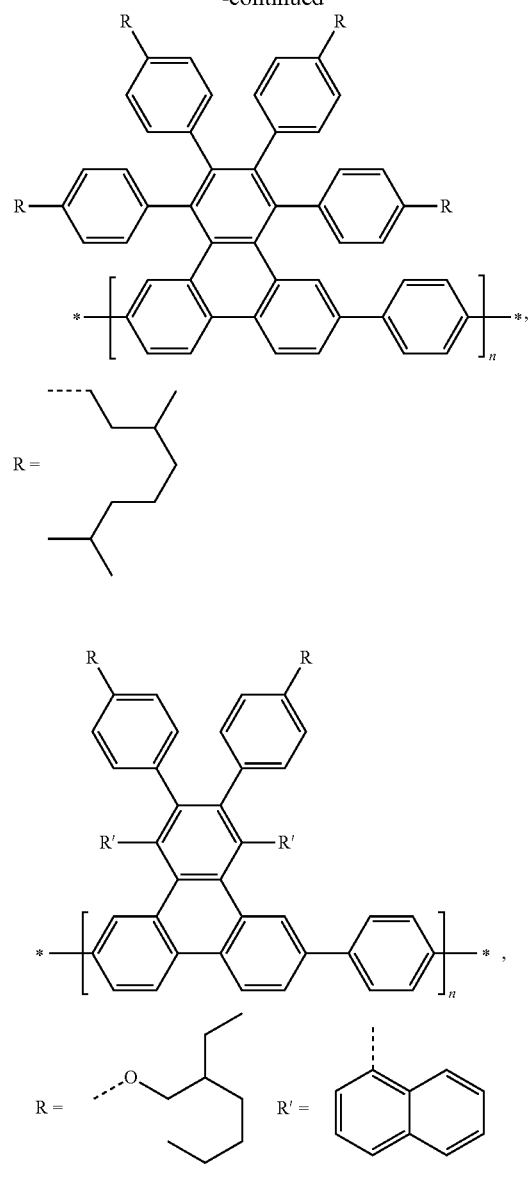
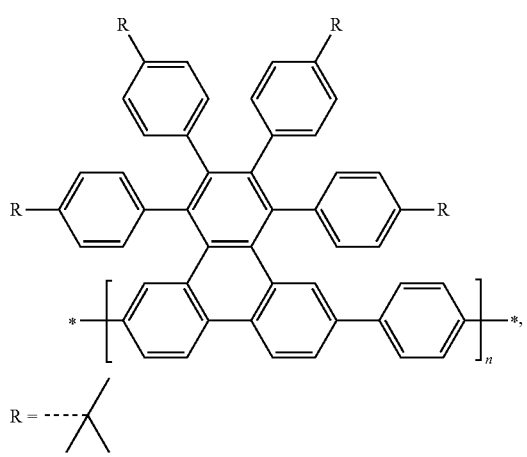
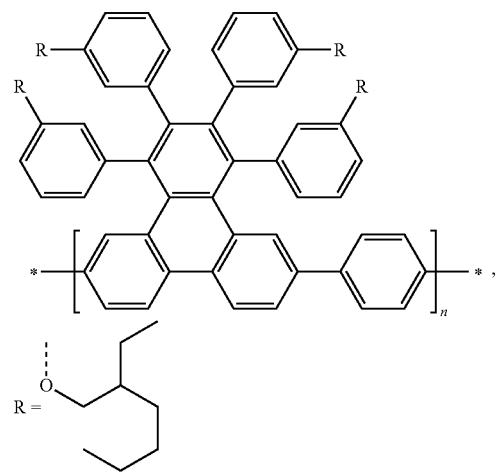

107
-continued
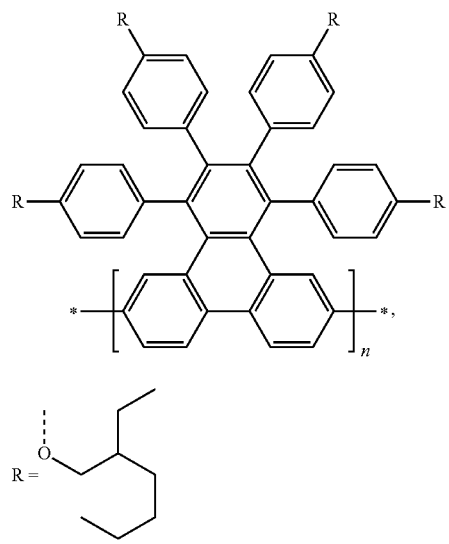
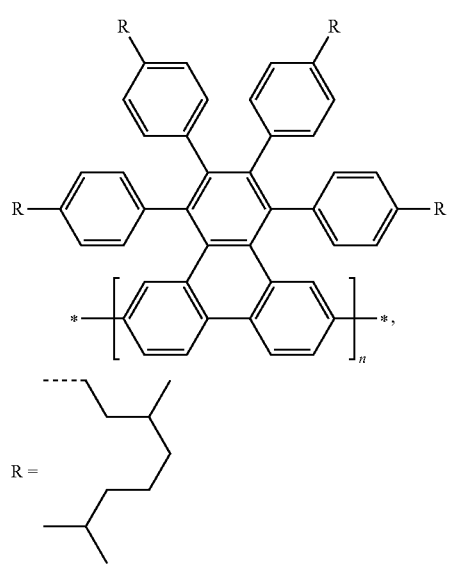
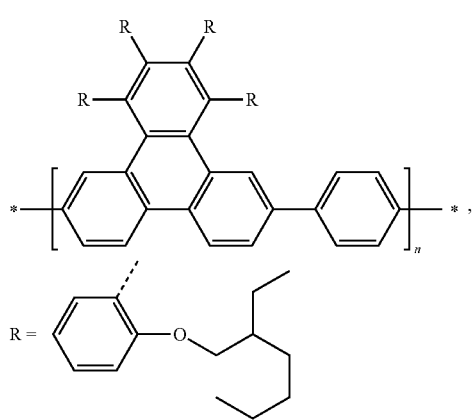
108
-continued
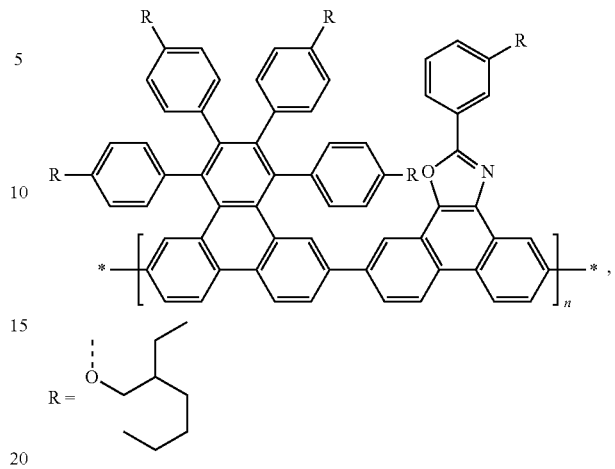
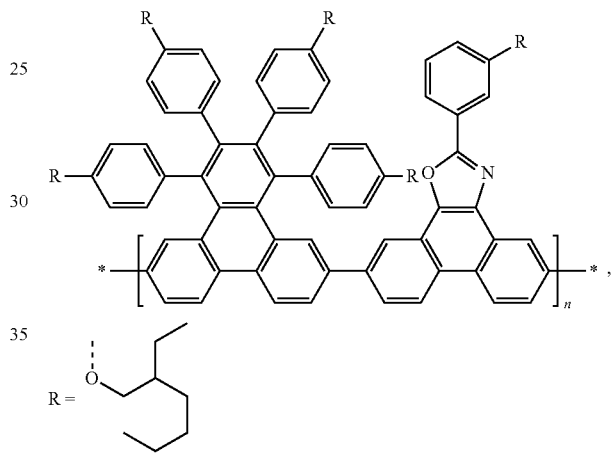
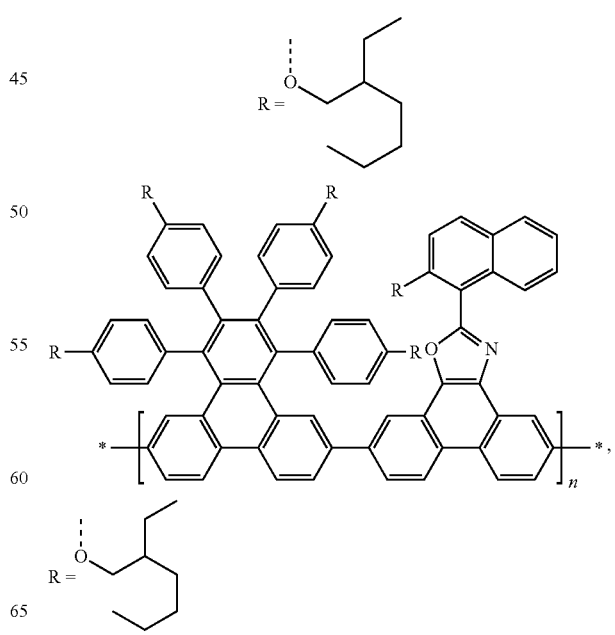

109
-continued
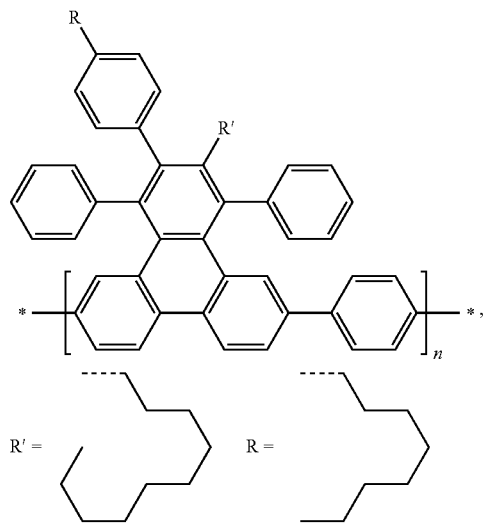
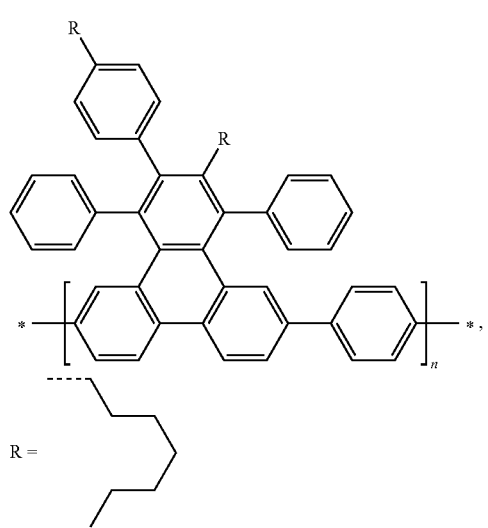
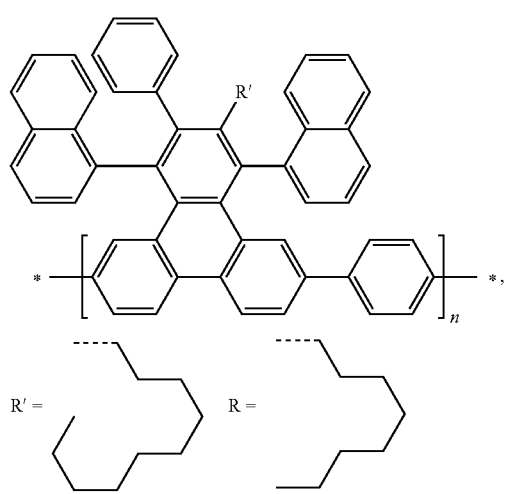
110
-continued
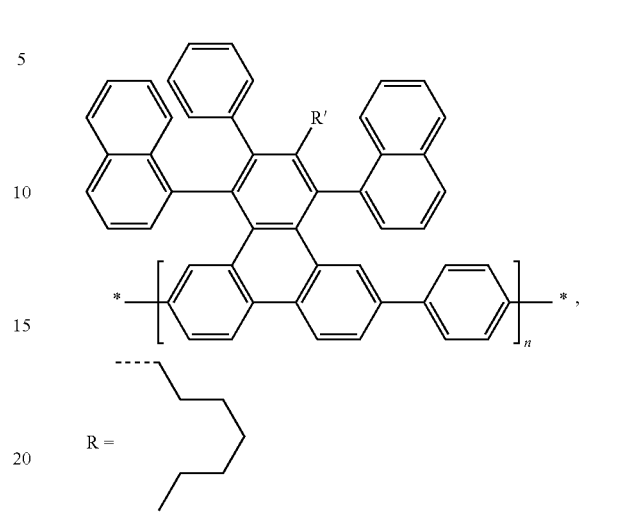
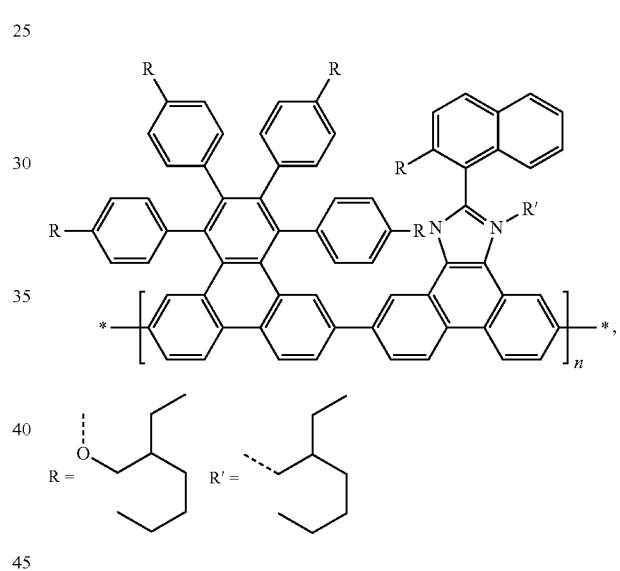
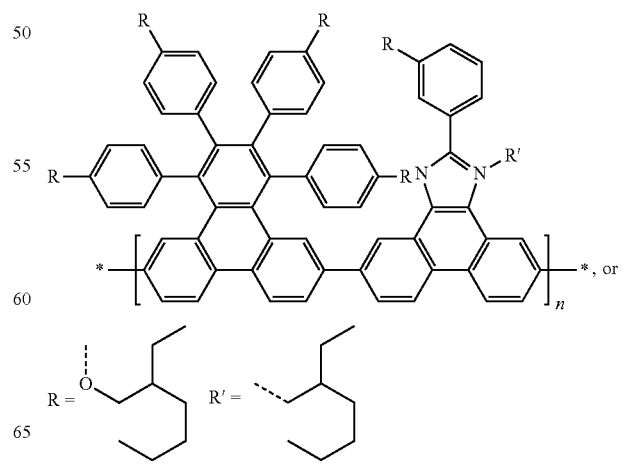, or

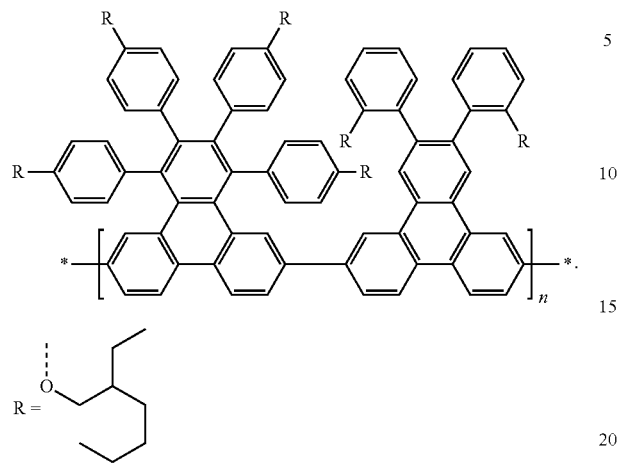
* * * * *